US011185286B2

(12) United States Patent
Wang et al.

(10) Patent No.: US 11,185,286 B2
(45) Date of Patent: Nov. 30, 2021

(54) WEARABLE ELECTROCHEMICAL SENSORS

(71) Applicant: The Regents of the University of California, Oakland, CA (US)

(72) Inventors: Joseph Wang, San Diego, CA (US); Joshua Ray Windmiller, Del Mar, CA (US); Amay Jairaj Bandodkar, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 436 days.

(21) Appl. No.: 15/806,216

(22) Filed: Nov. 7, 2017

(65) Prior Publication Data
US 2018/0220967 A1    Aug. 9, 2018

Related U.S. Application Data

(62) Division of application No. 14/400,242, filed as application No. PCT/US2013/040671 on May 10, 2013, now Pat. No. 9,820,692.
(Continued)

(51) Int. Cl.
*A61B 5/05* (2021.01)
*A61B 5/00* (2006.01)
(Continued)

(52) U.S. Cl.
CPC .......... *A61B 5/6833* (2013.01); *A61B 5/1477* (2013.01); *A61B 5/1486* (2013.01);
(Continued)

(58) Field of Classification Search
CPC ... A61B 5/6833; A61B 5/1864; A61B 5/1477; A61B 5/14539; A61B 5/14517;
(Continued)

(56) References Cited

U.S. PATENT DOCUMENTS 5,422,246 A * 6/1995 Koopal .................. A61L 31/10
                                                    204/403.1
6,120,460 A * 9/2000 Abreu .................. A61B 3/1241
                                                    600/405
(Continued)

FOREIGN PATENT DOCUMENTS

EP        1372602      4/2007
WO   2010045247 A1    4/2010
WO   2011156095 A2   12/2011

OTHER PUBLICATIONS

Bandodkar, A. et al., "Tattoo-Based Noninvasive Glucose Monitoring: A Proof-Of-Concept Study", Anal. Chem. 2015, 787, pp. 394-398.
(Continued)

*Primary Examiner* — Andrey Shostak
(74) *Attorney, Agent, or Firm* — Perkins Coie LLP

(57) ABSTRACT

Methods, structures, devices and systems are disclosed for fabricating and implementing electrochemical biosensors and chemical sensors. In one aspect, a method of producing an epidermal biosensor includes forming an electrode pattern onto a coated surface of a paper-based substrate to form an electrochemical sensor, the electrode pattern including an electrically conductive material and an electrically insulative material configured in a particular design layout, and attaching an adhesive sheet on a surface of the electrochemical sensor having the electrode pattern, the adhesive sheet capable of adhering to skin or a wearable item, in which the electrochemical sensor, when attached to the skin or the wearable item, is operable to detect chemical analytes within an external environment.

13 Claims, 23 Drawing Sheets

Related U.S. Application Data

(60) Provisional application No. 61/645,576, filed on May 10, 2012.

(51) Int. Cl.

| | | |
|---|---|---|
| *A61B 5/145* | (2006.01) | |
| *A61B 5/1477* | (2006.01) | |
| *A61B 5/1486* | (2006.01) | |
| *B32B 37/12* | (2006.01) | |
| *B32B 38/10* | (2006.01) | |
| *B32B 38/00* | (2006.01) | |

(52) U.S. Cl.
CPC ...... *A61B 5/14517* (2013.01); *A61B 5/14539* (2013.01); *B32B 37/1284* (2013.01); *B32B 38/10* (2013.01); *B32B 38/145* (2013.01); *B32B 2255/12* (2013.01); *B32B 2307/202* (2013.01); *B32B 2307/206* (2013.01); *B32B 2311/02* (2013.01); *B32B 2323/04* (2013.01); *B32B 2367/00* (2013.01); *B32B 2383/00* (2013.01); *B32B 2405/00* (2013.01); *B32B 2556/00* (2013.01); *Y10T 156/10* (2015.01)

(58) Field of Classification Search
CPC ... B32B 38/145; B32B 38/10; B32B 37/1284; B32B 2556/00; B32B 2405/00; B32B 2383/00; B32B 2367/00; B32B 2323/04; B32B 2311/02; B32B 2307/206; B32B 2307/202; B32B 2255/12; Y10T 156/10
See application file for complete search history.

(56) References Cited

U.S. PATENT DOCUMENTS

| | | | |
|---|---|---|---|
| 6,465,091 B1 | 10/2002 | Ou-Yang | |
| 6,546,268 B1* | 4/2003 | Ishikawa | A61B 5/0031 204/403.01 |
| 2002/0004640 A1 | 1/2002 | Conn et al. | |
| 2002/0072784 A1 | 6/2002 | Sheppard, Jr. et al. | |
| 2002/0105080 A1 | 8/2002 | Speakman | |
| 2002/0121438 A1* | 9/2002 | Saffell | G01N 27/4045 204/415 |
| 2004/0262582 A1* | 12/2004 | Kirkor | B82Y 10/00 252/500 |
| 2006/0127964 A1* | 6/2006 | Ford | A61B 5/14532 435/14 |
| 2008/0114220 A1* | 5/2008 | Banet | A61B 5/021 600/301 |
| 2008/0275327 A1* | 11/2008 | Faarbaek | A61B 5/411 600/382 |
| 2008/0277291 A1* | 11/2008 | Heller | A61B 5/14532 205/777.5 |
| 2009/0047550 A1* | 2/2009 | Kakuta | H01M 8/16 429/401 |
| 2009/0084678 A1* | 4/2009 | Joshi | A61B 5/14532 204/403.14 |
| 2009/0101498 A1* | 4/2009 | Papadimitrakopoulos | C01B 13/0259 204/403.11 |
| 2009/0191616 A1 | 7/2009 | Lu et al. | |
| 2009/0242429 A1* | 10/2009 | Sitdikov | B82Y 5/00 205/792 |
| 2010/0158788 A1* | 6/2010 | Kim | B01J 23/74 423/447.2 |
| 2011/0140703 A1 | 6/2011 | Chiao et al. | |
| 2011/0288388 A1* | 11/2011 | Shah | A61N 1/05 600/347 |
| 2011/0293894 A1* | 12/2011 | Sato | H01G 4/005 428/189 |
| 2011/0319787 A1 | 12/2011 | Lamoise et al. | |
| 2012/0228137 A1* | 9/2012 | Cho | A61B 5/14539 204/409 |
| 2013/0041235 A1* | 2/2013 | Rogers | A61B 5/1107 600/306 |
| 2015/0126834 A1 | 5/2015 | Wang et al. | |

OTHER PUBLICATIONS

Cheng, H. et al., "An analytical model of strain isolation for stretchable and flexible electronics", Appl. Phys. Lett. 98, 061902 (2011), 4 pages.

Chuang, M.C. et al., "Flexible thick-film glucose bionsensor: Influence of mechanical bending on the performance", Talanta, 2010, 81, pp. 15-19.

Coyle, S. et al., "Smart nanotextiles: A review of materials and applications", MRS Bull. 32, May 2007, pp. 434-442.

Diamond, D. et al., "Wireless sensor networks and chemo-/biosensing", Chem. Rev. 108,2008, pp. 652-679.

Gutowski, T. G. et al., "The elastic deformation of lubricated carbon fiber bundles: Comparison of theory and experiments", J. Compos. Mater. vol. 26, No. 16, 1992, pp. 2330-2347.

Kim, D. H. et al., "Epidermal Electronics", Science 333, 2011, pp. 838-843.

Ma, R. et al., A stretchable electrode array for non-invasive, skin-mounted measurement of electrocardiography (ECG), electromyography (EMG) and electroencephalography (EEG), 2nd Annual International Conference of the IEEE EMBS, 2010, pp. 6405-6408.

Malzahn, K.. et al., "Wearable electrochemical sensors for in situ analysis in marine environments" Analyst 136, 2011, pp. 2912-2917.

Matsuyama, H. et al., "Analysis of solute diffusion in poly(vinyl alcohol) hydrogel membrane",.J. Membrane Sci. 126, 1997, pp. 151-160.

Rogers, J.A. et al., "A curvy, stretchy future for electronics", PNAS, Jul. 7, 2009, vol. 106, No. 27, p. 10875-10876.

Romolo, F. S. et al., "Identification of gunshot residue: A critical review", Forensic Sci. Int.119, 2001, pp. 195-211.

Tubbetts, G. C. et al., "Mechanical properties of vapor-grown carbon fiber composites with thermoplastic matrices", J. Mater. Res. 14, 1999, pp. 2871-2880.

Wang, "Electrochemical Glucose Biosensors", Chem. Rev., 108:2008, pp. 814-825.

Wang, J. et al. "Screen-printed electrochemical hybridization biosensor for the detection of DNA sequences from the *Escherichia coli* pathogen", Electroanal., 1996, 9, pp. 395-398.

Wang, J. et al., "Bismuth-coated carbon electrodes for anodic stripping voltammetry" Anal.Chem. 72, 2000, pp. 3218-3222.

Wang, J. et al., "Miniaturized glucose sensors based on electrochemical codeposition of rhodium and glucose oxidase onto carbon-fiber electrodes", Anal.Chem. 64, 1992, pp. 456-459.

Wang, J. et al. "Thick-film electrochemical immunosensor based on stripping stripping potentiometric detection of a metal ion label", Anal. Chem., 1998, 70, pp. 1682-1685.

Wang, J., "Sol-gel materials for electrochemical biosensors", Anal. Chim. Acta, 399, 1999, pp. 21-27.

Windmiller, J.R. et al., "Bioelectronic system for the control and readout of enzyme logic gates", Sensor. Actuat. B 155, 2011, pp. 206-213.

Yang, Y. L. et al., "Thick-film textile-based amperometric sensors and biosensors" Analyst 135, 2010, pp. 1230-1234.

International Search Report and Written Opinion for PCT Application No. PCT/US2013/040671, dated Mar. 7, 2014, 11 pages.

Extended European Search Report for European Patent Application 13827958.3; dated Dec. 18, 2015; 9 pages.

Chuang, M. C. et al. "Textile-based electrochemical sensing: effect of fabric substrate and detection of nitroaromatic explosives", Electroanal. 22, 2010, pp. 2511-2518.

\* cited by examiner

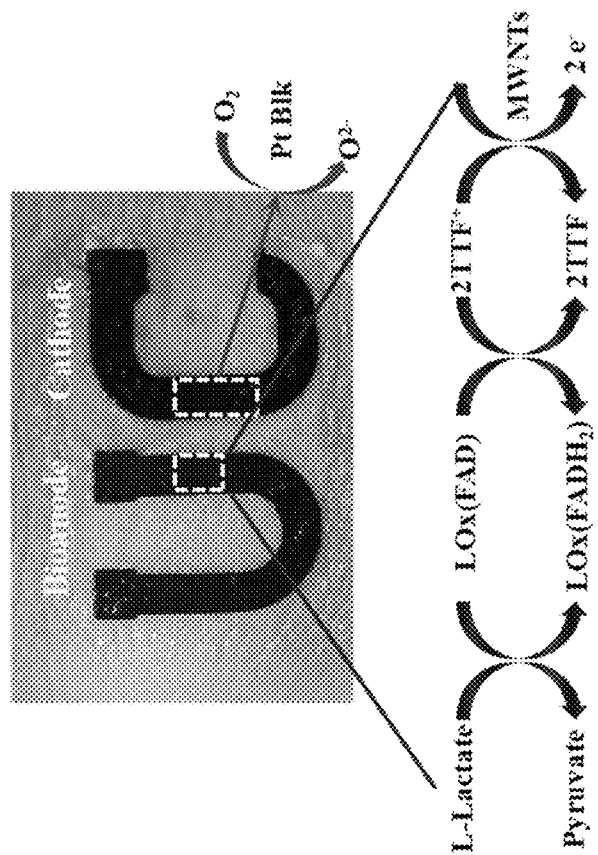
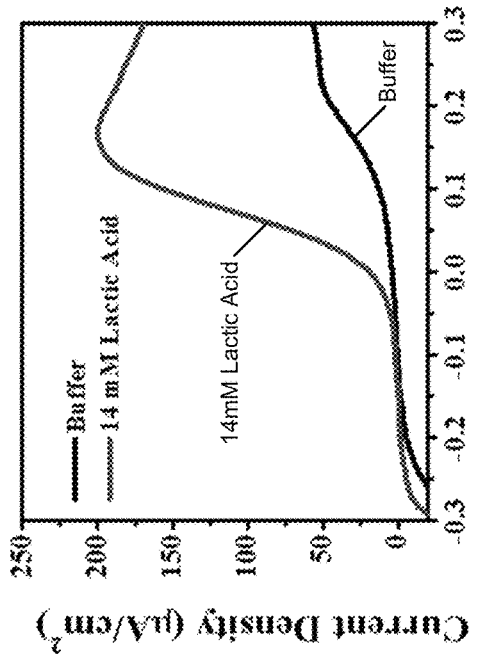
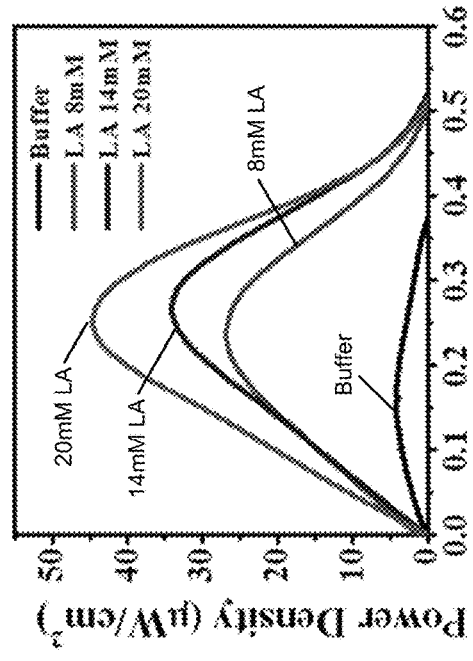
FIG. 18A
FIG. 18B
FIG. 18C

WEARABLE ELECTROCHEMICAL SENSORS

CROSS REFERENCE TO RELATED APPLICATIONS

This patent document is a divisional application of U.S. patent application Ser. No. 14/400,242, entitled "WEARABLE ELECTROCHEMICAL SENSORS", filed on Nov. 10, 2014, which is a 35 U.S.C. § 371 National Stage application of International Application No. PCT/US2013/040671, entitled "WEARABLE ELECTROCHEMICAL SENSORS", filed on May 10, 2013, which claims the benefit of priority of U.S. Provisional Patent Application No. 61/645,576, entitled "FLEXIBLE ELECTROCHEMICAL BIOSENSORS FOR DIRECT EPIDERMAL INTEGRATION," filed on May 10, 2012. The entire contents of the before-mentioned patent applications are incorporated by reference as part of the disclosure of this application.

STATEMENT REGARDING FEDERALLY SPONSORED RESEARCH OR DEVELOPMENT

The invention in this patent document was made with government support under contract no. N00014-08-1-1202 awarded by Office of Naval Research. The government has certain rights in the invention.

TECHNICAL FIELD

This patent document relates electrochemical sensor devices for sensing biological substances, chemical substances and other substances.

BACKGROUND

Sensors based on electrochemical processes can be used to detect a chemical, substance, a biological substance (e.g., an organism) by using a transducing element to convert a detection event into a signal for processing and/or display. Biosensors can use biological materials as the biologically sensitive component, e.g., such as biomolecules including enzymes, antibodies, nucleic acids, etc., as well as living cells. For example, molecular biosensors can be configured to use specific chemical properties or molecular recognition mechanisms to identify target agents. Biosensors can use the transducer element to transform a signal resulting from the detection of an analyte by the biologically sensitive component into a different signal that can be addressed by optical, electronic or other means. For example, the transduction mechanisms can include physicochemical, electrochemical, optical, piezoelectric, as well as other transduction means.

SUMMARY

Techniques, systems, and devices are described for fabricating and implementing electrochemical biosensors and chemical sensors that are wearable on skin or a wearable item, e.g., by a procedure analogous to the transfer of a temporary tattoo.

In one aspect of the disclosed technology, a method of producing an epidermal biosensor includes forming an electrode pattern onto a coated surface of a paper-based substrate to form an electrochemical sensor, the electrode pattern including an electrically conductive material and an electrically insulative material configured in a particular design layout, and attaching an adhesive sheet on a surface of the electrochemical sensor having the electrode pattern, the adhesive sheet capable of adhering to skin or a wearable item, in which the electrochemical sensor, when attached to the skin or the wearable item, is operable to detect chemical analytes within an external environment.

Implementations of the method can optionally include one or more of the following features. For example, in some implementations of the method, the adhesive sheet can include an outer coating layer on an external surface of the adhesive sheet not in contact with the electrode pattern. For example, the outer coating layer can include polyvinyl alcohol (PVA). In some implementations, for example, the method can further include removing the outer coating layer from the adhesive sheet to enable adhesion of the electrochemical sensor to the skin or the wearable item via the adhesive sheet. Also for example, the method can further include removing the paper-based substrate from the electrochemical sensor to expose the electrode pattern to the external environment. For example, the coated surface can include a release agent material including cellulose acetate. For example, the adhesive sheet can include polydimethylsiloxane (PDMS). In some implementations of the method, the forming can include performing screen printing, aerosol deposition, or inkjet printing the electrode pattern onto the coated surface of the paper-based substrate. For example, the electrically conductive material can include a conductive ink, e.g., including, but not limited to, gold, platinum, nickel, copper, silver, and/or silver chloride. For example, the electrically insulative material can include a nonconductive ink, e.g., including, but not limited to, polyethylene terephthalate (PET), polystyrene (PS), polyester (PE), and/or polytetrafluoroethylene (PTFE). In some examples, the electrode pattern can further include an electrically semi-conductive material. For example, the electrically semi-conductive material can include a semi-conductive ink, e.g., including, but not limited to, amorphous carbon, carbon black, graphite, carbon nanotubes, and/or graphene. In some implementations of the method, for example, the electrode pattern further can include carbon fiber segments dispersed within the electrically conductive or electrically semi-conductive material.

In another aspect, a method of producing an epidermal biosensor includes forming an electrode pattern onto a coated surface of a paper-based substrate to form an electrochemical sensor, the electrode pattern including an electrically conductive material and an electrically insulative material configured in a particular design layout, attaching an adhesive sheet on a surface of the electrochemical sensor having the electrode pattern, the adhesive sheet capable of adhering to skin or a wearable item and structured to include a coating layer on an external surface of the adhesive sheet, and removing the paper-based substrate from the electrochemical sensor to expose the electrode pattern, in which the electrochemical sensor, when attached to the skin or the wearable item, is operable to detect a substance present within a fluid that contact the electrode pattern coupled to the skin or the wearable item.

Implementations of the method can optionally include one or more of the following features. For example, in some implementations of the method, the electrochemical sensor can be operable to detect physiological, biological, or chemical signals from the skin. In some implementations, for example, the method can further include, when attached to the skin or the wearable item, removing the coating layer from the adhesive sheet exposing a non-adhesive surface of the adhesive sheet. For example, the coating layer can include PVA. For example, the coated surface of the paper-based substrate can include a release agent material including cellulose acetate. For example, the adhesive sheet can include PDMS. In some implementations of the method, the forming can include performing screen printing, aerosol deposition, or inkjet printing the electrode pattern onto the coated surface of the paper-based substrate. For example, the electrically conductive material can include a conductive ink, e.g., including, but not limited to, gold, platinum, nickel, copper, silver, and/or silver chloride. For example, the electrically insulative material can include a nonconductive ink, e.g., including, but not limited to, PET, PS, PE, and/or PTFE. In some examples, the electrode pattern can further include an electrically semi-conductive material. For example, the electrically semi-conductive material can include a semi-conductive ink, e.g., including, but not limited to, amorphous carbon, carbon black, graphite, carbon nanotubes, and/or graphene. In some implementations of the method, for example, the electrode pattern further can include carbon fiber segments dispersed within the electrically conductive or electrically semi-conductive material.

In another aspect, an epidermal electrochemical sensor device includes a substrate formed of a flexible electrically insulative material structured to adhere to skin or a wearable item, a first electrode formed on the substrate of an electrically conductive material, a second electrode configured on the substrate of a material that is electrically conductive and separated from the first electrode by a spacing region, the first and second electrodes capable of sustaining a redox reaction to produce an electrical signal, and a first electrode interface component and second electrode interface component formed on the substrate and electrically coupled to the first electrode and the second electrode, respectively, via electrically conductive conduit, in which, when attached to the skin or the wearable item and electrically coupled via the first and second electrode interface components to one or more electrical circuits, the device is operable to detect a substance in a local environment of the skin or the wearable item.

Implementations of the device can optionally include one or more of the following features. For example, in some implementations of the device, at least one of the first electrode or the second electrode can include an enzyme catalyst and an electroactive redox mediator, the electroactive redox mediator facilitating the transfer of electrons between the electrode and the active site of the enzyme catalyst configured to sustain a redox reaction. In some implementations, for example, the device can further include an electrically conductive underlayer on the substrate and underneath each of the first electrode and the second electrode, respectively, the underlayer providing separation of the first electrode and the second electrode.

In another aspect, a method to fabricate an epidermal electrochemical sensor device includes depositing an electrically conductive ink on an electrically insulative substrate to form two or more electrodes adjacent to and separated from one another and conduit wires connecting to each of the electrodes, the depositing including printing the ink on a first stencil placed over the substrate, the first stencil including a patterned region configured in a design of the two or more electrodes and the conduit wires to allow transfer of the ink on the substrate, and the first stencil inhibiting transfer of the ink in areas outside the patterned region; curing the electrically conductive ink; depositing an electrically insulative ink on the substrate to form an insulative layer that exposes the two or more electrodes, the depositing including printing the electrically insulative ink on a second stencil placed over the substrate, the second stencil including a printing region configured in a second design to allow transfer of the ink on the substrate, the second stencil inhibiting transfer of the ink in areas outside the printing region; and curing the electrically insulative ink.

Implementations of the method can optionally include one or more of the following features. For example, in some implementations, the method can further include depositing an adhesive layer on the insulative layer that exposes the two or more electrodes, the adhesive substrate formed of a flexible electrically insulative material structured to adhere to skin or a wearable item of a user. In some implementations, for example, the substrate can include a paper substrate. For example, the paper substrate can include an upper layer and a base paper layer, the upper layer comprising a release agent coated on the base paper layer and structured to peel off to remove the paper substrate. For example, the curing can include implementing at least one of applying heat or ultraviolet radiation to the deposited ink on the substrate. In some implementations, for example, the method can further include forming an electrically semi-conductive layer over at least one of the two or more electrodes by printing an ink of an electrically semi-conductive material on a third stencil placed over the substrate, the third stencil including a printing region configured in a first design of the at least one of the two or more electrodes, the printing region allowing transfer of the ink on the paper substrate, and the third stencil inhibiting transfer of the ink in areas outside the printing region; and curing the electrically semi-conductive ink. In some implementations, for example, the method can further include dispersing carbon fibers in the electrically conductive ink. In some implementations, for example, the method can further include depositing an ion-selective membrane to the surface of at least one of the electrodes, in which the depositing includes performing at least one of: (i) drop-casting the ion-selective membrane on the anterior surface of the electrode, (ii) screen printing the ion-selective membrane on the anterior surface of the electrode, (iii) inkjet printing the ion-selective membrane on the anterior surface of the electrode, and/or (iv) aerosol deposition of the ion-selective membrane on the anterior surface of the electrode. In some implementations, for example, the method can further include depositing a catalyst to the surface of at least one of the electrodes, in which the depositing includes performing at least one of: (i) encasing the catalyst in a porous scaffold structure formed of a conducting polymer on the surface of the electrode, (ii) covalently binding the catalyst to the surface of the electrode, (iii) entrapping the catalyst in a selectively permeable membrane coupled to the surface of the electrode, and/or (iv) electrostatically binding the catalyst to the surface of the electrode. In some implementations, for example, the method can further include depositing an electroactive redox mediator to the surface of the at least one of the electrodes including the catalyst to form an electrochemical sensing layer, in which the electroactive redox mediator facilitates the transfer of electrons between the electrode and the active site of the catalyst. In some implementations, for example, the method can further include depositing multi-walled carbon nanotubes on the surface of at least one of the two or more electrodes.

The subject matter described in this patent document can be implemented in specific ways that provide one or more of the following features. For example, the disclosed technology has wide-ranging implications in the healthcare, fitness, sport and athletics performance monitoring, beauty/skin care, dermatology, environmental, and general sensing domains. For example, the disclosed technology can be easily adapted for use in the generalized healthcare, fitness, sport, remote monitoring, wireless healthcare, personalized medicine, performance monitoring, and war-fighter monitoring domains. Also, for example, the disclosed technology can involve the substitution of test strips for metabolite and electrolyte monitoring in the perspiration, and may replace conventional screen printed electrochemical test strips in other diagnostics and environmental monitoring applications.

These and other aspects and their implementations and applications are described in greater detail in the drawings, the description and the claims.

BRIEF DESCRIPTION OF THE DRAWINGS

FIG. 18A shows an image of an exemplary tattoo biofuel cell device attached to a human wrist.

FIG. 18B shows a data plot of polarization curves of a functionalized anode of an exemplary tattoo biofuel cell device.

FIG. 18C shows a data plot of the power density of an exemplary tattoo biofuel cell device.

Like reference symbols and designations in the various drawings indicate like elements.

DETAILED DESCRIPTION

Figure 1A:
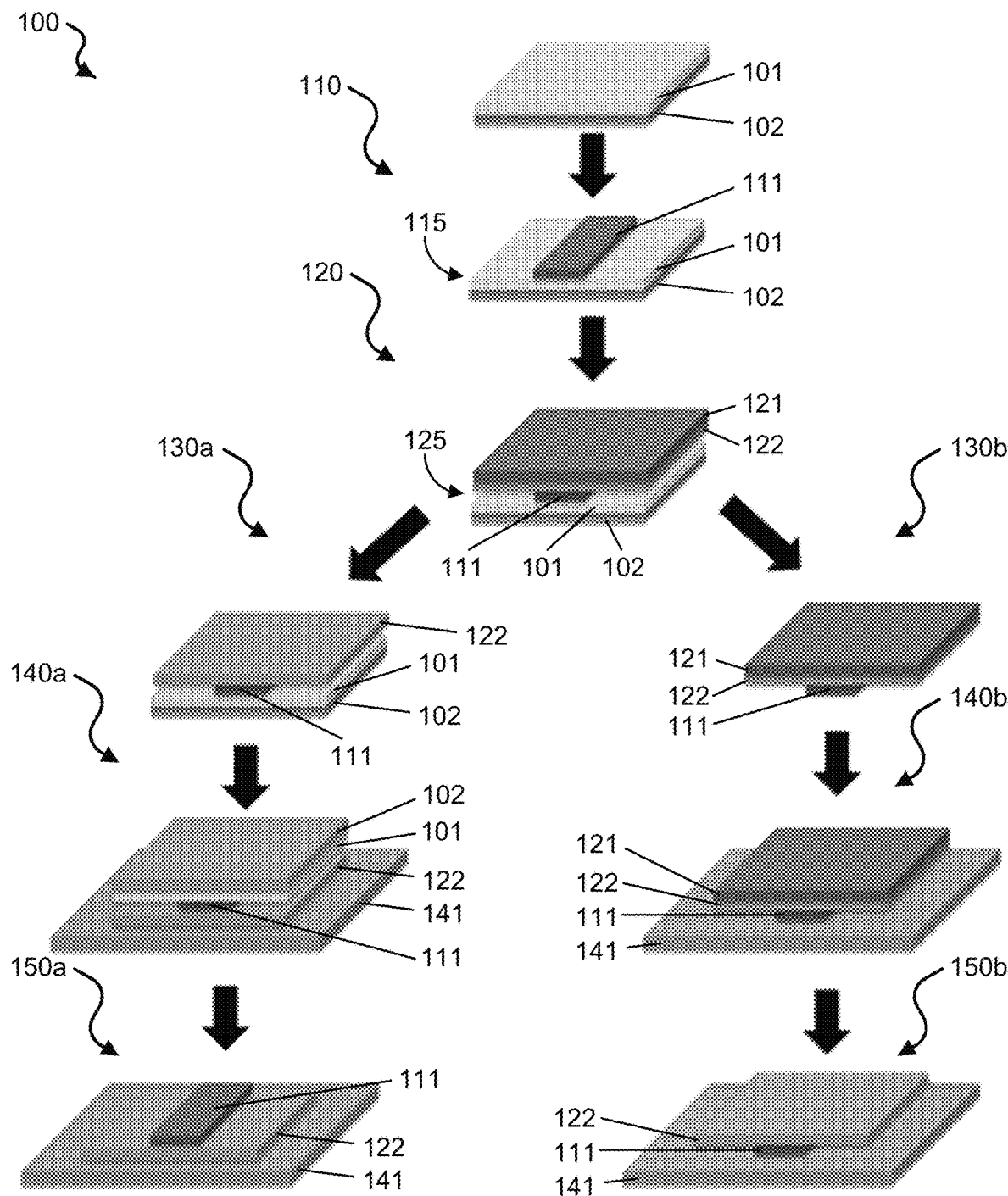
FIG. 1A shows a process diagram illustrating an exemplary fabrication protocol to produce epidermal electrochemical sensors of the disclosed technology.

Advances in material and device fabrication techniques can be used body-worn electronic devices that are mated directly with the skin for the measurement of physiological parameters of the individual wearer. The disclosed technology here can enable body-worn devices to provide analysis of chemical constituents residing on the surface of the skin. This analysis can provide useful insight into the overall health and physical activities of an individual and possible exposure to chemical or biological agents and certain hazardous substances. For successful implementation of direct epidermal electrochemical devices attached to the body of a user, the devices must exhibit compatible elasticity between the device substrate and the skin.

Techniques, systems, and devices are described for fabricating and implementing electrochemical biosensors and chemical sensors that can be transferred onto the skin or wearable item, e.g., by a procedure analogous to the transfer of a temporary tattoo.

The disclosed technology can include biosensors and chemical sensors that use detection methodologies including amperometry, voltammetry, potentiometry, and/or electrochemical impedance spectroscopy for epidermal monitoring of a wearer's bodily substances such as fluids or gases or the wearer's exposure to one or more substances in the surrounding environment. The disclosed biosensors and chemical sensors can include temporary transfer electrochemical biosensors and chemical sensors that can be applied for limited or long term use on the user's skin for direct physiological and security monitoring of chemical constituents. The exemplary temporary transfer electrochemical biosensors and chemical sensors can be produced in the form of aesthetic designs similar as a skin tattoo, referred to herein as epidermal temporary transfer tattoo (T3) sensors. In some implementations, the disclosed sensors can include electrode patterns forming a complete electrochemical system, as well as include the selection of the appropriate layering and ink formulation to facilitate the required electrochemical response. Exemplary sensors of the disclosed technology can be implemented in epidermal monitoring of the wearer's environment and physiological fluids residing on the surface of the epidermis, e.g., such as perspiration. For example, the exemplary sensors can be used to measure one or more physiological parameters, e.g., including but not limited to measurements of chemical or biological substances in body fluids and provide useful insight into the real-time physical conditions or overall health of the individual wearer as well as their exposure to chemical or biological agents/hazards residing in their local environment by analyzing of the detected chemical constituents residing on the surface of the skin. For example, the exemplary sensors can be used in noninvasive on-body continuous-monitoring in healthcare, fitness, remote monitoring, and other applications.

The disclosed technology includes fabrication processes to produce the exemplary temporary transfer electrochemical biosensors and chemical sensors. For example, in some implementations, the disclosed fabrication processes includes a method to produce the exemplary T3 sensors that is compatible with the non-planar features and surface irregularities that are characteristic of the human anatomy, e.g., to provide direct chemical sensing on the skin. Exemplary approaches of this method can include the adhesion of printable, high-resolution electrode patterns onto the epidermis using T3 substrates. The exemplary T3 chemosensors are compatible with the skin and can be mated with and conform to the contours of the body. In some implementations, for example, carbon fiber-reinforced tattoo inks can be employed in the exemplary T3 sensors to provide the durability required to withstand the mechanical stresses relevant to epidermal wear. In some examples of the disclosed T3 sensors, customized artistic electrode patterns can be produced that conceal their electrochemical functionality. The sensing paradigm of the exemplary T3 sensors can be suitable for a plethora of diverse body-worn chemosensing applications where true bionic integration is a core requirement for developing 'electronic skin'.

In some implementations, the disclosed electrochemical sensors and biosensors can be printed on paper, plastic, or ceramic substrates that are either inserted into or included on the surface of a wearable item, e.g., including, but not limited to, a wristwatch, armband, chest-strap, belt, or headband for direct epidermal contact and sensing.

In one aspect, a method of producing an epidermal biosensor includes forming an electrode pattern onto a coated surface of a paper-based substrate to form an electrochemical sensor, the electrode pattern including an electrically conductive material and an electrically insulative material configured in a particular design layout, and attaching an adhesive sheet on a surface of the electrochemical sensor having the electrode pattern, the adhesive sheet capable of adhering to skin or a wearable item, in which the electrochemical sensor, when attached to the skin or the wearable item, is operable to detect chemical analytes within an external environment.

In another aspect, a method of producing an epidermal biosensor includes forming an electrode pattern onto a coated surface of a paper-based substrate to form an electrochemical sensor, the electrode pattern including an electrically conductive material and an electrically insulative material configured in a particular design layout, attaching an adhesive sheet on a surface of the electrochemical sensor having the electrode pattern, the adhesive sheet capable of adhering to skin or a wearable item and structured to include a coating layer on an external surface of the adhesive sheet, and removing the paper-based substrate from the electrochemical sensor to expose the electrode pattern, in which the electrochemical sensor, when attached to the skin or the wearable item, is operable to detect a substance present within a fluid that contact the electrode pattern coupled to the skin or the wearable item.

For example, the disclosed technology can be used to construct a body-worn sensor device that is either directly attached to the skin or is included as part of a body-worn article, e.g., such as clothing, a wrist band, a wrist watch, a piece of footwear, or a monitoring device. Such a body-worn sensor device can include a multi-layer material structure that has an electrochemical sensing material layer interacting with a substance to be detected, an electrode layer formed on and in electrical contact with the electrochemical sensing material layer with a printed electrode pattern to receive one or more applied electrical signals and to output one or more electrical output signals from the electrochemical sensing material layer indicating a reaction with the substance to be detected, and a base layer to provide the support to the electrochemical sensing material layer and the electrode layer. A sensor circuit may be integrated onto the base layer in some sensor designs, or may be located outside the base layer, but is electrically coupled to the electrode layer. The multi-layer material structure may be a flexible structure for attaching to skin or a body-worn object. For skin-attached applications where such a sensor is an epidermal electrochemical sensor device, the multi-layer material structure may include a removable substrate layer such as a paper substrate and a releasing agent layer over the base layer so that device can be attached to skin after removing the removable layer. Such an epidermal electrochemical sensor device can use cellulose acetate, for example, over the removable paper substrate, and an insulator layer as the base layer which can be, e.g., a silicone material such as PDMS to provide an electrically insulating component of the overall electrode pattern of the sensor device.

Examples of sensor structures, materials and fabrication of the above and other sensor devices are provided below to illustrate various aspects of the disclosed technology.

FIG. 1A shows a process diagram illustrating an exemplary fabrication method 100 to produce epidermal electrochemical sensors of the disclosed technology, e.g., such as the exemplary T3 electrochemical sensors. The method 100 includes a process 110 to form electrode structures 111 on a release agent 101 coated on a paper-based substrate 102 to form an electrochemical sensor component 115. For example, the electrode structures 111 can be patterned on the release agent 101-coated paper substrate 102, in which the electrode pattern includes an electrically conductive material and an electrically insulative material, and in some examples an electrically semi-conductive material, configured in a particular design layout. In some examples, the process 110 can include screen printing the electrically conductive material (e.g., electrically conductive ink) and the electrically insulative material (e.g., electrically insulative ink), and in some examples an electrically semi-conducting ink, in the patterned design to form the electrode structures 111.

The method 100 includes a process 120 to apply an adhesive sheet 122 with a protective coating 121 to the electrochemical sensor component 115 to form an electrochemical sensor device 125 capable of attaching to skin (or a wearable item) for one of sensing analytes in the external environment of the skin or fluids present on the skin.

The exemplary inks employed can include a wide variety of materials (e.g., such as graphite, gold, platinum, nickel, silver, silver chloride, polyethylene terephthalate (PET), polytetrafluoroethylene (PTFE), etc.), and their viscosity can be modified (e.g., using either binders or solvents) as needed to yield optimal results. For example, the ink can be prepared with various chemical modifications in order to impart selectivity, increase sensitivity, reduce response time, and/or further extend the stability of the amperometric, voltammetric, or potentiometric response of the electrochemical sensor device. This can include the incorporation of chemical moieties into the ink suspension (e.g., catalysts, biocatalysts, enzymes, proteins, nanoparticles, reagents, mediators, binding agents, and/or cofactors), as well as the patterning of perm-selective or ion-selective coatings/membranes to the surface of the exemplary sensor. For example, the electrically conductive ink can include, but is not limited to, gold, platinum, nickel, silver, and silver chloride inks. For example, the electrically insulative ink can include, but is not limited to, PET and PTFE inks. In some examples, the electrode structures 111 can also include electrically semi-conductive materials including semi-conductive ink, e.g., including, but not limited to, amorphous carbon, carbon black, or graphite.

In some implementations of the method 100, as shown in FIG. 1A, the fabricated electrochemical sensor device 125 is prepared for epidermal monitoring of a wearer's surrounding environment. For example, the electrochemical sensor device 125 could be used to detect volatile organic compounds, explosive remnants, and pollutants present in the air surrounding the device 125 on the user's skin. In such cases, the method 100 can further include a process 130a to remove the protective coating 121 from the adhesive sheet 122 of the electrochemical sensor device 125. Subsequently, the method 100 then includes implementing a process 140a to flip the electrochemical sensor device 125 to be applied to skin 141, in which the adhesive sheet 122 is attached to the skin 141 such that the paper based substrate 102 is positioned away from the skin 141. The method 100 can then include implementing a process 150a to remove the paper based substrate 102, thereby exposing the adhered electrode structures 111 (e.g., electrode sensor pattern) to the wearer's external environment for remote sensing. For example, the process 150a can include applying water to the releasing agent 101 to allow smooth release of the paper based substrate 102 from the electrode structures 111.

In some implementations of the method 100, as shown in FIG. 1A, the fabricated electrochemical sensor device 125 is prepared for epidermal physiological monitoring, e.g., of fluids containing biochemical analytes present on the skin. In such cases, the method 100 can further include a process 130b to remove the paper based substrate 102 from the electrochemical sensor device 125. For example, the process 130b can include applying water to the releasing agent 101 to allow smooth release of the paper based substrate 102 from the electrode structures 111. Subsequently, the method 100 then includes implementing a process 140b to apply the electrochemical sensor device 125 to the skin 141 via the attachment of the adhesive sheet 122 to the skin 141 such that the external surface of the electrode structures 111 are in contact with the surface of the skin 141. In some implementations, the method 100 can then include implementing a process 150b to remove the protective coating 121 from the adhesive sheet 122 of the electrochemical sensor device 125.

Figure 1B:
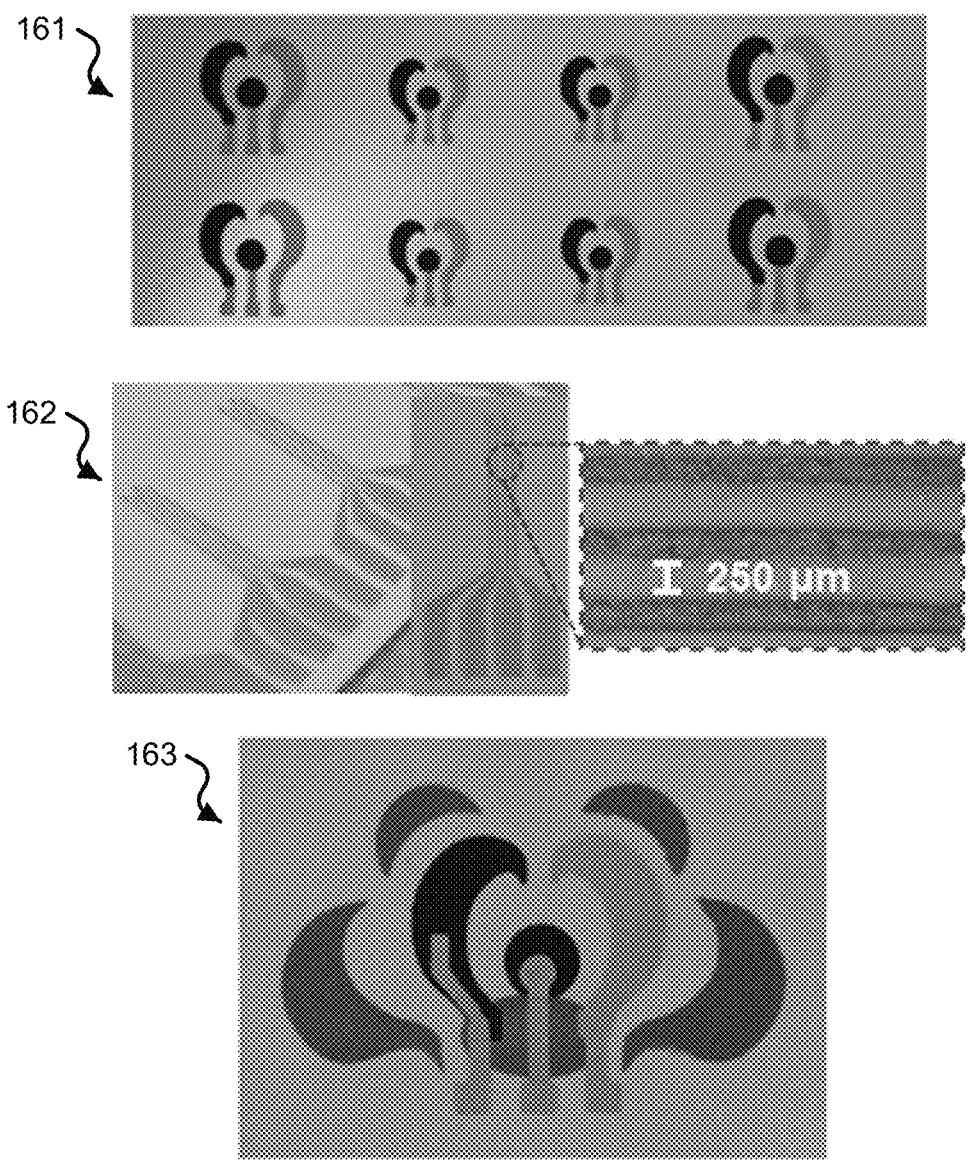
FIGS. 1B and 1C show images of exemplary epidermal electrochemical sensors.

FIG. 1B shows images 161, 162, and 163 of exemplary T3 electrochemical sensors showing several exemplary printed designs. The image 161 illustrates a high-quality array of three-electrode artistic electrochemical sensors possessing two varying sizes. The image 162 illustrates an array of microelectrodes that can be used for small-sample bioanalysis, for example. The corresponding inset in the image 162 exemplifies that well-defined patterns possessing micrometer-scale resolution can be produced with the disclosed fabrication method 100. The image 163 shows an exemplary artistically patterned T3 electrochemical sensors that can be employed for environmental sensing of the wearer's local vicinity. The exemplary T3 electrochemical sensor depicted in the image 163 indicates that the implementation of finely-segmented and well-dispersed carbon fibers do not compromise the quality of the thick-film fabrication process. For example, the exemplary T3 electrochemical sensors can be fabricated using the described thick film process without special arrangements to accommodate the T3 paper in the printing process.

Figure 1C:
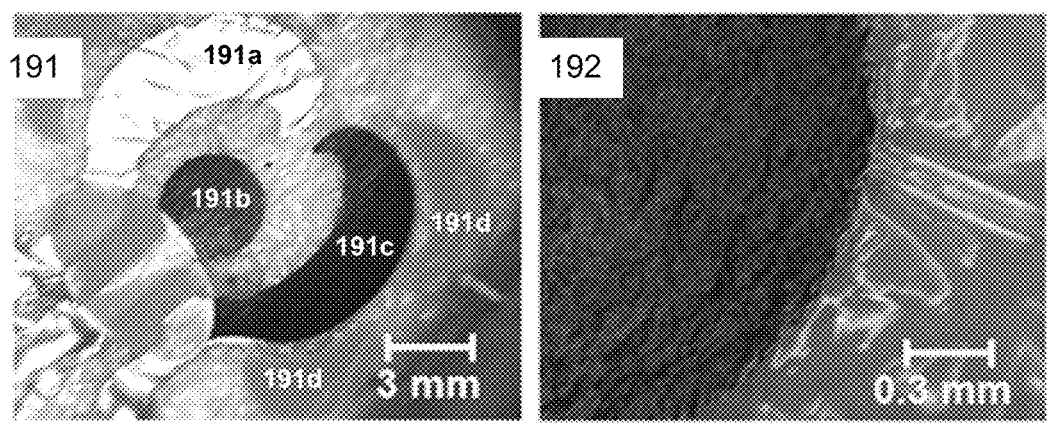

FIG. 1C shows an image 191 of an exemplary three-electrode T3 biosensor applied to porcine skin for physiological monitoring. The image 191 displays exemplary constituents of the sensor that include an Ag/AgCl reference electrode (191a), a carbon working electrode (191b), a carbon counter electrode (191c), and an insulator structure (191d) that circumscribes the electrodes. FIG. 1C also shows an image 192 showing a magnified view of the carbon electrodes 191b displaying well-defined borders and rough morphology.

In one exemplary implementation of the method 100, for example, a sheet of paper can be coated with a thick-film of cellulose acetate to impart rigidity for subsequent processing. After the cellulose acetate layer has dried and solidified, a thick-film of silicone such as polydimethylsiloxane (PDMS) can be deposited and the paper-cellulose acetate-PDMS contingent can be cured at a specific temperature to solidify the PDMS layer. Thereafter, a thick-film of warm polyvinyl alcohol (PVA) can be deposited on the surface and allowed to dry. Subsequently, the ink can be cured, e.g., at a suitable temperature. The exemplary process is then repeated, as needed, for the number of layers required. Each layer can either employ an identical ink formulation as the previous layer or a different one entirely. For example, the described fabrication technique includes integration of printing and tattoo-transfer protocols and thick-film fabrication processes to produce such advanced electrochemical sensors capable of epidermal detection of physiologically-relevant compounds as well as agents of environmental/security relevance. The exemplary technique can produce body-worn electrochemical sensors that are compliant with the skin for the realization of non-invasive extended chemical monitoring. Nearly any artistic tattoo design can be formed in the fabrication of the electrochemical sensors, e.g., allowing the sensors to be concealed in rather inconspicuous tattoo artwork, without compromising the favorable resolution and performance inherent to printable sensors.

Figure 1D:
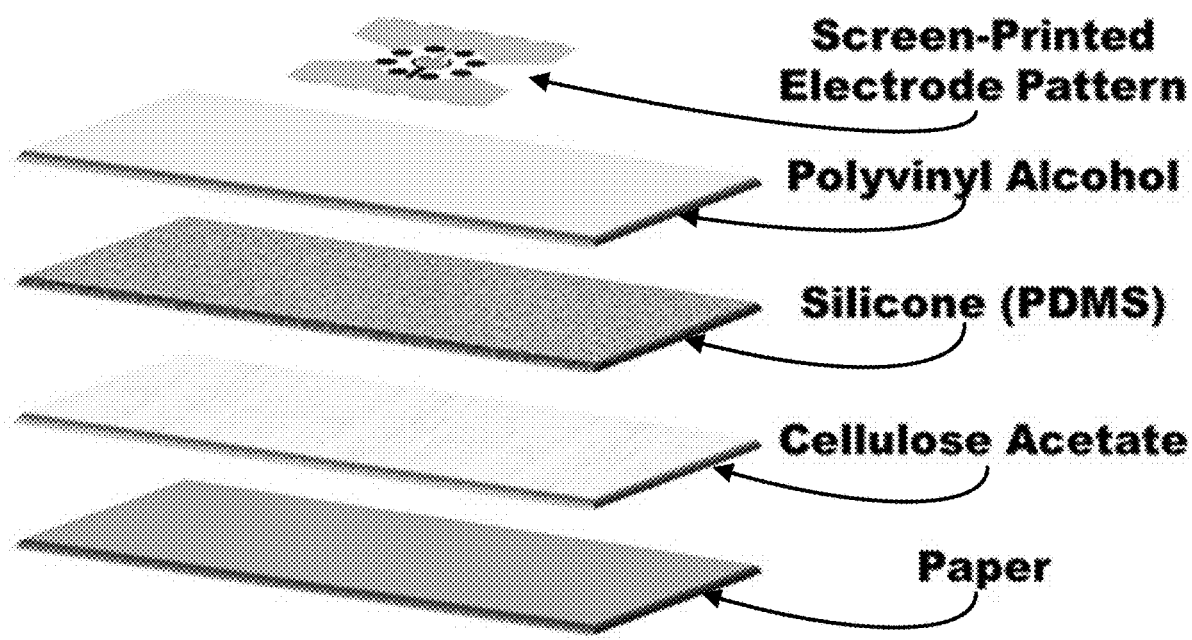
FIG. 1D shows a schematic illustration of exemplary material layers of an exemplary epidermal electrochemical sensor device.

FIG. 1D shows a schematic illustration of exemplary material layers of an exemplary epidermal electrochemical sensor device. In this example, the exemplary device includes a paper substrate and a releasing agent layer, e.g., formed of cellulose acetate, over the paper substrate. The exemplary device also includes an insulator layer, e.g., formed of a silicone material, such as PDMS, that is formed on the releasing agent layer to provide an electrically insulating component of the overall electrode pattern of the sensor device. In this example, an outer coating layer, e.g., polyvinyl alcohol (PVA), is applied on the insulator layer. The exemplary device includes an electrode pattern, e.g., which can be screen printed on the coating layer, including electrically conductive and/or electrically semi-conductive inks to form the electrodes of the sensing device in any desired pattern.

In some implementations of the method 100, for example, carbon fiber (CF) segments can be dispersed within the tattoo ink to augment the electrode's tensile strength and provide the electrode with an interlinked conductive backbone while enhancing the electrochemical behavior, hence reflecting the inherent properties of the fiber constituents. Inclusion of such CFs in the ink materials can counteract cracking and alleviate mechanical degradation associated with routine skin-based wear. By harnessing CF-dispersed inks for mechanical reinforcement, the fabricated electrochemical sensors exhibit substantial resiliency against extreme deformation, e.g., such as repeated pinching, bending, flexing, and twisting. The resulting wearable epidermal sensing devices of the disclosed technology thus couple favorable substrate-skin elasticity along with highly attractive electrochemical performance.

Figure 1E:
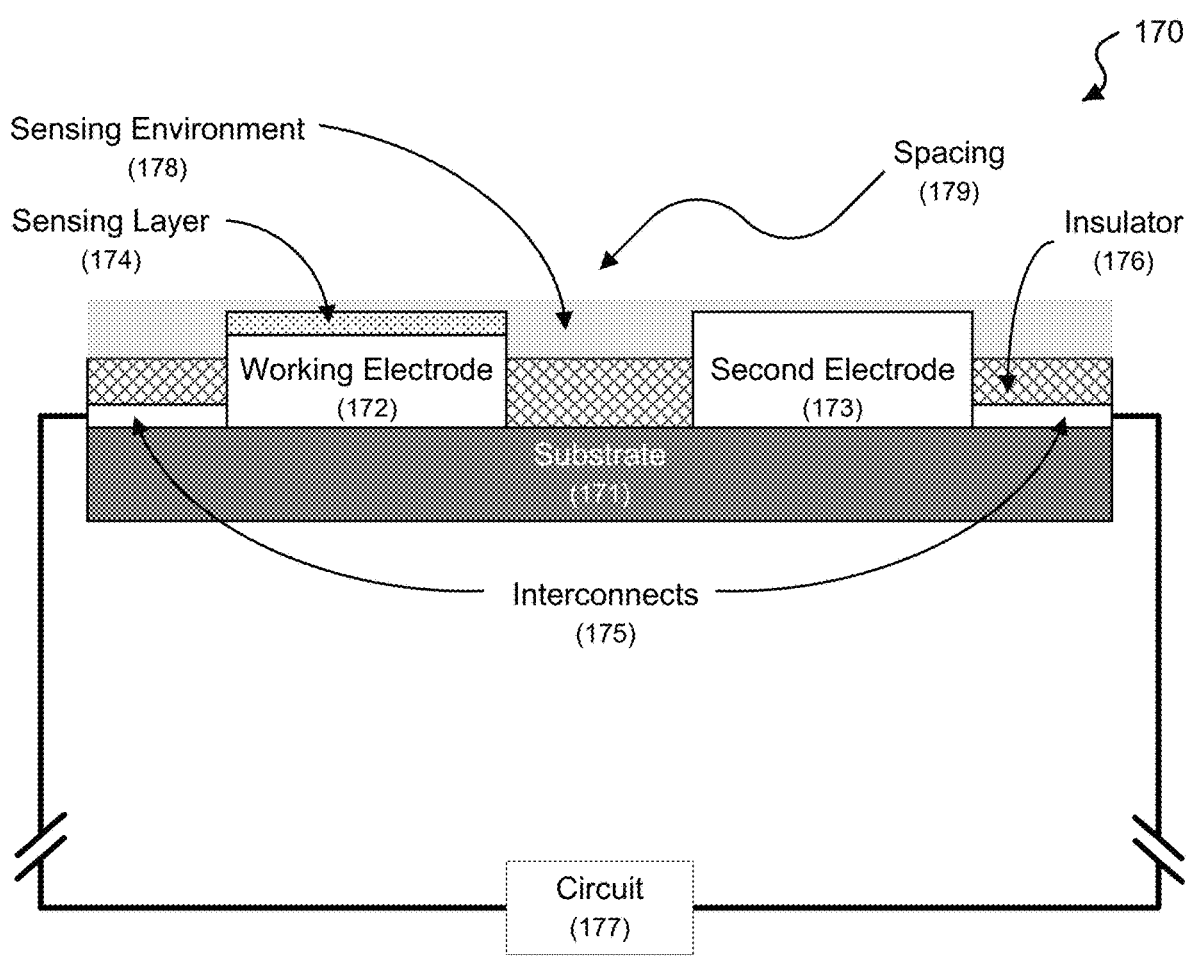
FIG. 1E shows a block diagram of an exemplary epidermal electrochemical sensor device.

FIG. 1E shows a block diagram of an exemplary embodiment of an epidermal electrochemical sensor device 170 capable of being worn on skin or a wearable item. The electrochemical sensor device 170 includes a substrate 171 of an electrically insulative material, which can be configured as a flexible substrate. The electrochemical sensor device 170 includes a working electrode 172 and a second electrode 173 on the substrate 171, in which the working electrode 172 and the second electrode 173 are separated from one another by a spacing region 179. The electrochemical sensor device 170 can include an insulator layer or structure 176, e.g., which can provide further support for the device 170, as well as include various artistic designs like that of a tattoo.

For example, the electrode configuration of the disclosed epidermal electrochemical sensor devices can be designed based on the type of target analyte to be sensed and the type of detection methodology, e.g., amperometry, voltammetry, potentiometry, and/or electrochemical impedance spectroscopy, to be employed. In some examples, the epidermal electrochemical sensor device 170 can be configured to detect charged analytes, e.g., using potentiometry. In some examples, the epidermal electrochemical sensor device 170 can be configured to detect self-oxidizing analytes on a bare working electrode 172, in which the device includes a third electrode (not shown in FIG. 1E) positioned between the working electrode 172 and second electrode 173; and the second electrode 173 and the third electrode can serve as a counter electrode and a reference electrode, respectively. In some embodiments, for example, the electrochemical sensor device 170 includes an array of electrodes, e.g., such as an array of working electrodes, counter electrodes, and/or reference electrodes.

In other examples, as shown in the diagram of FIG. 1E, the working electrode 172 includes an electrochemical sensing layer 174 to sustain a redox reaction to produce a detectable electrical signal that can be detected using, for example, amperometry and/or voltammetry. The electrochemical sensing layer 172 provides a reaction agent (e.g., the catalyst) that can undergo a redox reaction with a target analyte (e.g., such as a particular molecule or substance) that produces charge carriers sensed by the working electrode 172. The electrochemical sensing layer 172 can be structured to include a catalyst and an electroactive redox mediator. In some examples, the target analyte can be oxidized by the catalyst, releasing electrons in the process, which gives rise to an electrical current that can be measured between the working electrode 172 and second electrode 173. For example, the electroactive redox mediator can facilitate the transfer of electrons between the working electrode 172 and the active site of the catalyst. The electrochemical sensing layer 174 can be configured to the working electrode 172 in at least one of the following configurations: (i) the catalyst dispersed within the material of the working electrode 172; (ii) the catalyst coated as a layer on the surface of the working electrode 172; (iii) the catalyst entrapped by an electropolymerized conducting polymer formed on the surface of the working electrode 172; (iv) the catalyst entrapped by a selectively permeable scaffold structure, e.g., such as Nafion or chitosan, formed on the surface of the working electrode 172; (v) the catalyst covalently bonded to the surface of the working electrode 172; or (vi) the catalyst electrostatically anchored to the surface of the working electrode 172. In exemplary implementations including the electroactive redox mediator, for example, the electroactive redox mediator can be configured in the electrochemical sensing layer 174 along with the catalyst by the same exemplary configuration.

As shown in the diagram of FIG. 1E, the electrochemical sensor device 170 includes an electrical sensor circuit 177 electrically coupled to the electrodes via electrical interconnects 175. For example, the sensor circuit 177 can be configured to apply excitation waveforms and/or transduce the electrical signals generated by the electrochemical electrodes of the electrochemical sensor device 170 upon excitation. In some examples, the sensor circuit 177 can include a display or other interface to display the results to the wearer or other user, e.g., such as a coach, trainer, or physician. The sensor circuit 177 can be structured to include, but not limited to, a potentiostat (e.g., to realize amperometric and voltammetric measurements) or a galvanostat (e.g., to realize potentiometric measurements). In some embodiments, for example, the electrochemical sensor device 170 can include electrically conductive contact pads coupled to the interconnects 175 to provide a conductive surface to electrically interface an external circuit (e.g., such as the sensor circuit 177) to the electrodes of the electrochemical sensor device 170.

The electrochemical sensor device 170 can be applied to skin or a wearable item in such a way that a sensing environment 178 can include, for example, fluids in contact with the user's skin or clothing worn by the user, or the external environment in which the user is in, e.g., including air or water. The sensing environment 178 contains the target analyte to come into contact with the electrodes. In some examples, if the sensing environment 178 includes a fluid, e.g., such as a body fluid like perspiration.

Exemplary implementations of the disclosed electrochemical sensor technology were performed, which included the described materials, procedures, and data.

The exemplary implementations described herein included the use of the following materials and equipment. For example, ascorbic acid (AA), uric acid (UA), 2,4-dinitrotoluene (DNT), potassium ferricyanide ($K_3Fe(CN)_6$), 2,4,6-trinitrotoluene (TNT), potassium phosphate monobasic ($KH_2PO_4$), and potassium phosphate dibasic ($K_2HPO_4$) were used without further purification or modification. Chopped carbon fibers (CFs), e.g., including having 8 μm diameter, 6.4 mm length, 93% purity, were processed to reduce the CF length to approximately 0.5 mm. The exemplary reagents were prepared in a 0.1 M phosphate buffer solution (PBS, pH 7.4). Ultrapure water (18.2 MΩ·cm) was used in the exemplary implementations, and the exemplary implementations described were performed at room temperature. For example, Ag/AgCl conductive ink carbon graphite ink and insulator ink were utilized. Laser temporary tattoo paper kits were obtained from HPS Papilio (Rhome, Tex.). For comparison, custom-fabricated carbon screen-printed electrodes (on alumina, 2 mm working electrode diameter) were employed. Cadaveric porcine skin samples were immediately refrigerated upon arrival until temporary transfer tattoos were applied. A CH Instruments (Austin, Tex.) model 660D electrochemical analyzer was employed, for example, for the voltammetric, amperometric, potentiometric, and impedometric experiments. A Keithley (Cleveland, Ohio) model 6514 system electrometer was used to characterize trace resistance, for example. An Olympus optical microscope with an integrated CCD camera was utilized, for example, to investigate the surface morphology of the printed epidermal sensors in greater detail.

Exemplary sensor patterns were designed in AutoCAD (Autodesk, San Rafael, Calif.) and outsourced for fabrication on 75 µm-thick stainless steel stencils. For example, a separate stencil pattern was created for each layer (e.g., Ag/AgCl, carbon, insulator). A semi-automatic screen printer was employed for the fabrication efforts. For example, in order to conduct electrochemical experiments, a tattoo pattern containing a circular working electrode was designed and possessed a 3 mm radius. For example, in order to increase the tensile strength of the printed electrodes and mitigate the cracking observed during typical wear, 100 mg of chopped CFs were dispersed in 30 mL of ink and homogenized thoroughly.

Exemplary fabrication methods of the disclosed technology to manufacture electrochemical biosensors and chemical sensors were employed to produce the exemplary T3 sensors for transfer onto skin (or other wearable items) in a procedure analogous to that employed to transfer of a temporary tattoo. Exemplary techniques described involved the layering of certain materials on a substrate (e.g., paper substrate), on top of which a screen-, aerosol-, or inkjet-printed sensor pattern was defined. The substrate, e.g., containing the thick-film sensor patterns, was reversed and applied to the skin using a damp water-infused cloth or sponge. The backing substrate of the exemplary fabricated sensor device was then peeled away, leaving only the functional printed sensor pattern and a water-soluble synthetic polymer binder.

For example, screen printing can be employed for the formation of thick-film electrodes intended to be used in a wide variety of electrochemical applications. For example, this technique employs an automated system that guides a squeegee across a patterned stencil to extrude a specially-formulated ink in order to transfer an identical electrode pattern onto the substrate. This technique offers an attractive combination of moderate throughput and low cost.

Exemplary implementations were performed to investigate the printing quality of the exemplary ink materials on the T3 paper substrate. The exemplary T3 sensors fabricated using the disclosed methods were applied to the epidermis of various human subjects, and exemplary implementations were performed to evaluate the exemplary T3 sensors.

Figure 2A:
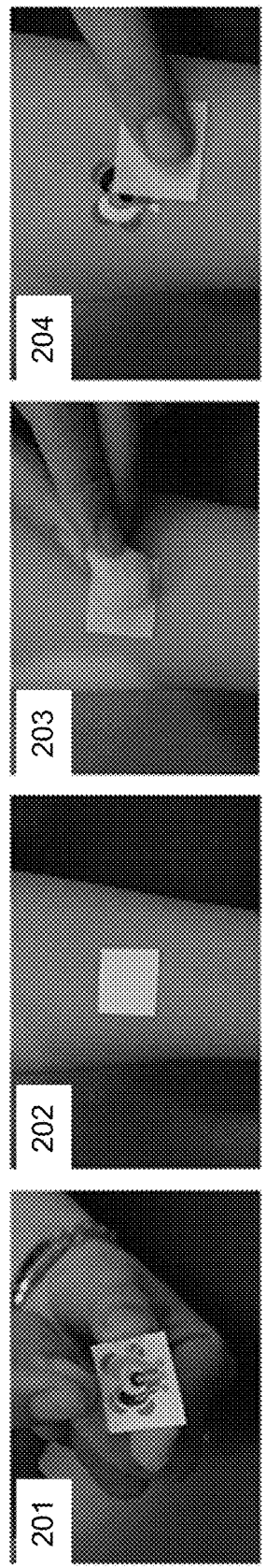
FIGS. 2A-2C show images of exemplary electrochemical sensors placed on a user's skin.

FIG. 2A shows images 201-204 for transferring an exemplary epidermal electrochemical sensor device, e.g., such as the exemplary device shown in the images 163 and 190 of FIGS. 1B and 1C, on a user's skin. The image 201 shows the exemplary electrochemical sensor device attached to the paper substrate, in which the protective film removed and the adhesive layer exposed. The image 202 shows the exemplary electrochemical sensor device with the attached paper substrate applied to the user's skin such that the electrode patterned region is in direct contact with the epidermis. For example, the T3 paper is flipped (e.g., electrode patterned side down) and depressed on the surface of the skin. The image 203 shows the wetting of the releasing agent layer of the exemplary electrochemical sensor device attached to the user's skin. For example, the paper substrate is gently dabbed with water until it becomes saturated. The image 204 shows the removal of the paper substrate, e.g., leaving the printed electrode contingent in direct contact with the epidermis. For example, the paper substrate is removed from the epidermis by gradually sliding it along and off the skin surface.

Figure 2B:
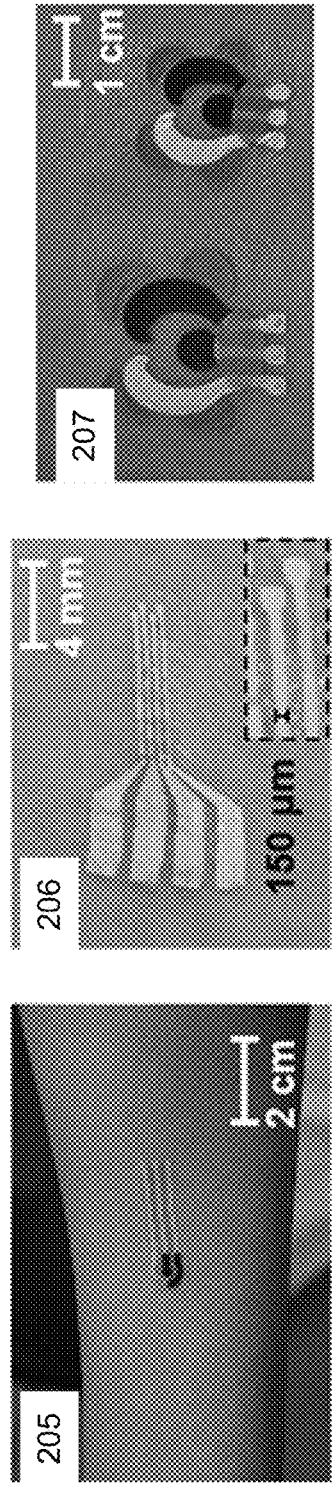

FIG. 2B shows images 205, 206, and 207 of several representative design permutations transferred onto the epidermis. The image 205 shows an exemplary three-electrode electrochemical sensing contingent, and the image 206 shows the transfer of an exemplary high-resolution sensor array onto the skin. For example, the inset image in the image 206 shows well-defined 150 µm-wide electrode features that are easily transferred onto the epidermis, e.g., underscoring the fidelity at which the patterns are printed and transferred. The image 207 displays a pair of exemplary artistically-inspired and fully functional three-electrode sensors possessing two different sizes. The disclosed T3 electrochemical sensors can be configured in nearly any electrode design and can be implemented without compromising the sensor functionality, e.g., such as in cases when an artistic impact is desired.

Figure 2C:
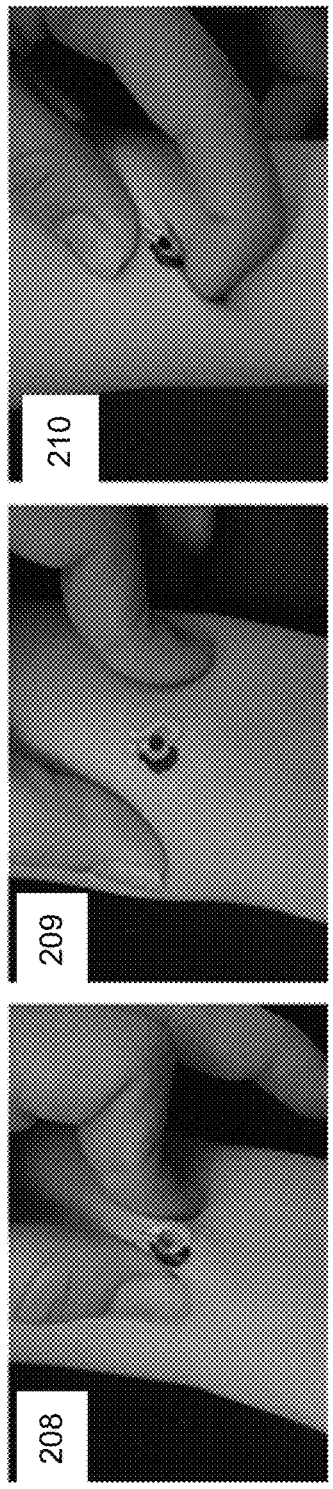

FIG. 2C shows images 208, 209, and 210 that validate the structural resiliency of the exemplary T3 sensors to extreme mechanical deformations, e.g., in which various strain permutations were applied to the sensors. For example, the images 208 and 209 demonstrate deformation of an exemplary tattoo sensor when pinched with the forefingers or upon stretching the skin, respectively. Likewise, for example, the image 210 illustrates a twisting operation on the exemplary sensor. As shown in the images of FIG. 2C, the application of these strain permutations exhibited minimal effect on the appearance and quality of the T3 sensor. Additional exemplary implementations on the impact of such strain permutations upon the electrochemical performance of these printable epidermal sensors were performed.

Exemplary implementations were performed for electrochemical characterization of the T3 sensing methodology aimed at comparing the disclosed sensing paradigm with conventional screen printed electrodes (SPEs) on solid alumina substrates. For example, voltammetric signatures were contrasted between the two systems, and a GORE-TEX fabric was used for the tattoo investigations in order to emulate the viscoelastic properties of the epidermis.

Figure 3A:
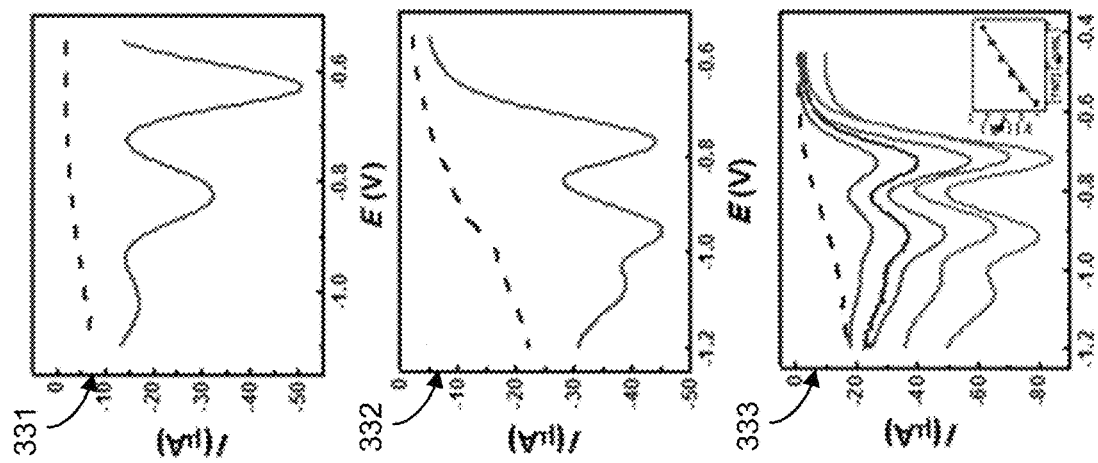
FIGS. 3A-3C show data plots of exemplary electrochemical sensors and screen printed electrodes.

FIG. 3A shows cyclic voltammogram data plots 311, 312, and 313 that were obtained for 2.5 mM ascorbic acid (AA) at an exemplary SPE (shown in the plot 311), at an exemplary T3 sensor on GORE-TEX (shown in the plot 312), and at an exemplary CF-reinforced T3 sensor on GORE-TEX (shown in the plot 313). The exemplary tattoo-based sensor embodied favorable electrochemical properties when compared with the conventional SPE. As an additional benefit, for example, the incorporation of CFs into the ink matrix enhanced the electrochemical response of the tattoo sensor device substantially, leading to better-defined oxidation peaks that emulated the response obtained at the conventional electrode contingent. Moreover, for example, both the unreinforced T3 electrochemical sensors and the CF-reinforced T3 electrochemical sensor exhibited resiliency against thirty repetitive 180° bending iterations, hence maintaining their favorable voltammetric behavior under extreme mechanical strain. As can be inferred from a comparison of the inset plots in the plots 312 and 313, both the unreinforced and CF-reinforced T3 sensors displayed only small (e.g., less than 10%) deviations from the original current response following repetitive bending operations.

Figure 3B:
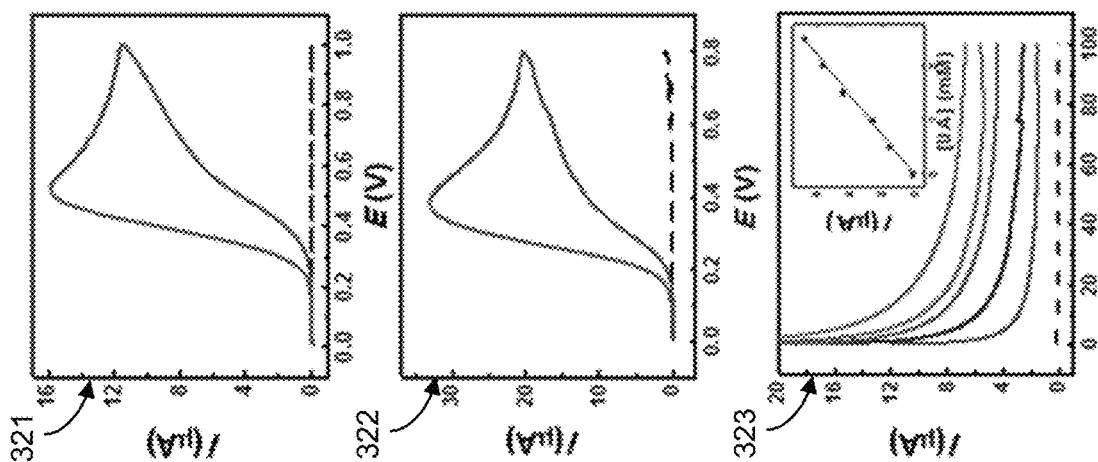

FIG. 3B shows cyclic voltammetric response plots 321 and 322 that were obtained for the detection of 2.5 mM uric acid (UA) at an exemplary SPE (shown in the plot 321) an exemplary CF-reinforced T3 sensor on porcine skin (shown in the plot 322). As represented from these exemplary data, the CF-reinforced tattoo electrode exhibited improved electrochemical performance to that of the SPE. For example, the peak potential and peak current assumed more desirable values when compared with the conventional SPE. FIG. 3B also shows an amperometric response plot 323 generated at the exemplary CF-reinforced T3 electrochemical sensor for increasing UA concentration. For example, a highly linear calibration was recorded at the skin-based electrode, corroborating its use not only as a viable alternative to SPEs but also as an advanced epidermal electrochemical sensor.

Figure 3C:
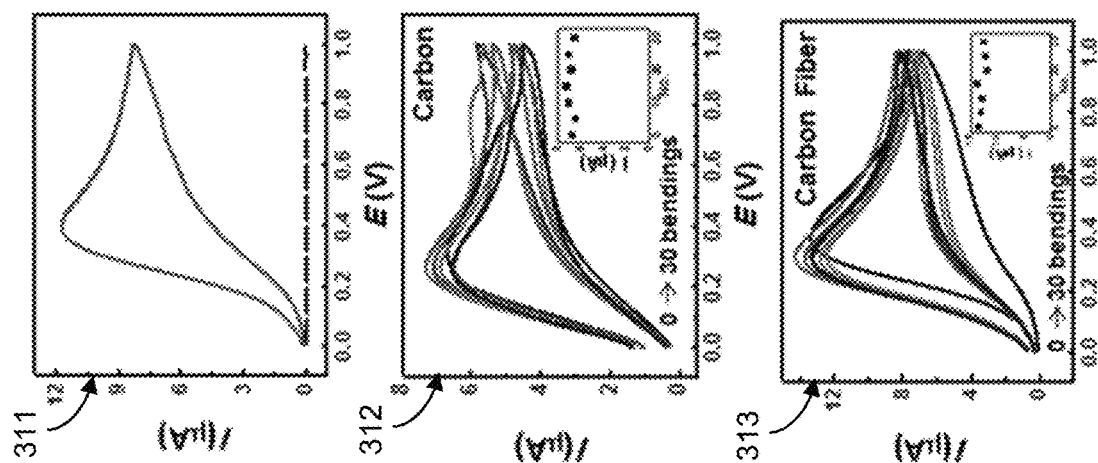

The disclosed tattoo sensing paradigm can also be extended to the identification of environmental substances including hazards and pollutants present in the vicinity of the wearer, e.g., for environmental and security monitoring. For example, the disclosed technology was extended to the detection of the common explosive 2,4,6-trinitrotoluene (TNT), in connection with square wave voltammetry (SWV). FIG. 3C shows SWV plots 331 and 332 that were obtained for the electrochemical detection of 225 µg/mL TNT at an exemplary SPE (shown in the plot 331) an exemplary CF-reinforced T3 sensor on porcine skin (shown in the plot 332). Both the plots 331 and 332 exemplify the well-defined TNT response, which substantiates that the exemplary T3 electrochemical sensors (even when mated with the skin) contend with the performance offered by well-established SPE sensors fabricated on solid supports. FIG. 3C also shows an SWV response plot 333 of the exemplary epidermal sensor for increasing TNT concentrations, which is shown to be well-defined and highly linear (as shown in the inset plot).

Exemplary implementations were performed to investigate the fundamental electrical properties of an exemplary T3 sensor, e.g., which can be considered imperative in order to ascertain its utility as a viable electrochemical device for integration with epidermal electronics. For example, a resistive and complex-valued impedance profile was evaluated under the application of mechanical deformation.

Figure 4A:
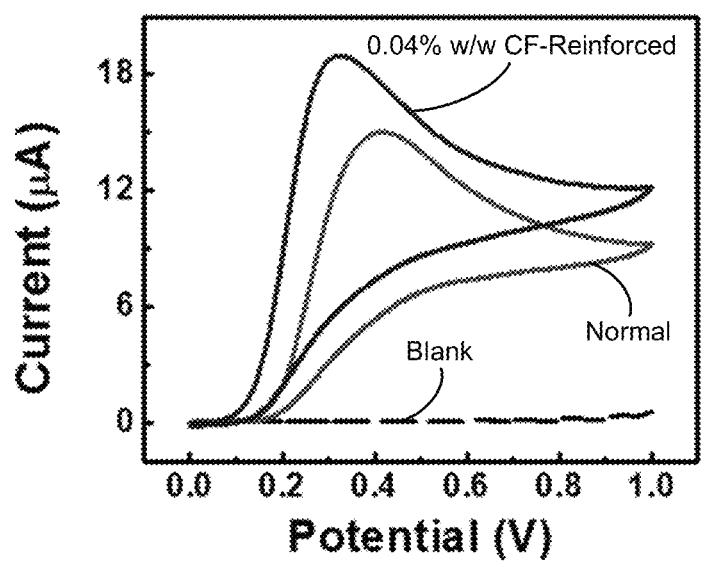
FIGS. 4A-4C show cyclic voltammogram data plots of exemplary electrochemical sensors.
Figure 4B:
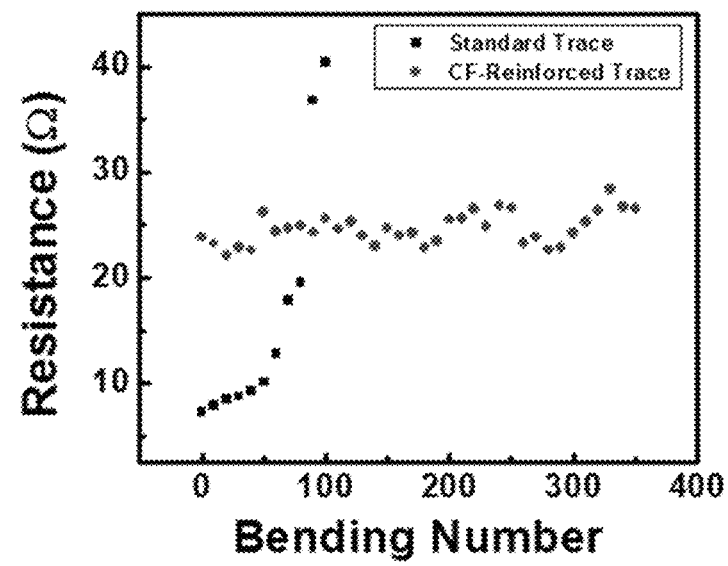
Figure 4C:
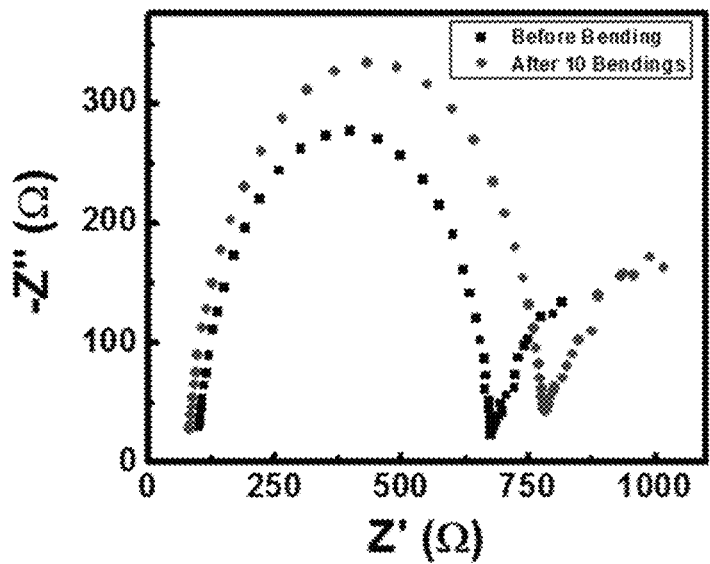

FIG. 4A shows a cyclic voltammogram plot illustrating the enhanced response generated by the dispersion of CF segments into the ink matrix, e.g., in which the scan rate was 10 mV/s. FIG. 4B shows a resistive profile plot of a normal (black squares) and carbon fiber-reinforced (red dots) 1 cm Ag/AgCl tattoo trace on porcine skin. FIG. 4C shows a plot of Nyquist complex-valued impedance curves generated by an exemplary T3 sensor before bending (black squares) and after 10 bending operations (red dots) on porcine skin, e.g., in which potassium ferricyanide ($K_3Fe(CN)_6$) was employed as the redox probe. For example, the impedance spectrogram parameters included a frequency of 0.1 Hz-10 kHz, an applied potential of 0.4 V vs. Ag/AgCl, and an amplitude of 10 $mV_{pp}$.

The implementations included resistance measurements that were recorded via the application of multimeter probes at opposite extremities of a 1 cm Ag/AgCl trace on an exemplary GORE-TEX-based T3 sensor (including both the CF-modified and unmodified embodiments). As previously shown in the insets of the plots 312 and 313, respectively in FIG. 3A, both the exemplary unreinforced and CF-reinforced tattoo sensors exhibited repeatable electrochemical performance following several dozen bending iterations. However, in this example, the unreinforced/standard electrode trace increased in its intrinsic resistance until catastrophic failure occurred at the $100^{th}$ bending iteration, e.g., represented by a completely severed trace, R=∞, as shown in FIG. 4B. Conversely, for example, in this exemplary implementation, the exemplary CF-reinforced electrode, although possessing slightly elevated intrinsic resistance at the commencement of the implementation (e.g., ~25Ω), maintained its conductivity even following over 350 bending repetitions, and hence substantiating its ability to withstand highly-repetitive mechanical deformation and underscores its suitability for epidermal integration.

The exemplary implementations included an electrochemical impedance spectroscopy performed at the exemplary CF-reinforced T3 sensor (on GORE-TEX), e.g., to ascertain the frequency at which the complex impedance indicates a transition from a reaction that is controlled via mass-transfer to one that is governed by kinetics. As exemplified in FIG. 4C, this transition occurred at approximately 4 Hz and 8 Hz for this exemplary CF-reinforced T3 sensor prior to and immediately following ten bending iterations, respectively. As shown in FIG. 4C, for example, the change in the impedance profile following stretching was shown to be minimal. In accordance with the Randles-Ershler formalism, a solution resistance, $R_Ω$, of ~100Ω, charge transfer resistance, $R_{ct}$, of ~580Ω, and a double-layer capacitance, $C_{dl}$, of 3.6 µF, can be interpolated from the plot.

The increased tolerance of the CF-dispersed electrodes against severe mechanical deformation should not compromise the electroanalytical performance offered by the disclosed devices. This is shown in FIG. 4A. For example, an exemplary unreinforced T3 biosensor was evaluated alongside an exemplary CF-reinforced T3 biosensor possessing a 0.04% (w/w) CF loading level in an exemplary implementation to provide the cyclic voltammetric response. As shown FIG. 4A, the electrochemical figures of merit differed slightly between the unreinforced (e.g., $E_p$=0.42 V, $i_p$=15.0 µA, and $k_s$=8.8E$^{-4}$ cm/s) and the 0.04% CF-reinforced sensor (e.g., $E_p$=0.32 V, $i_p$=19.0 µA, and $k_s$=1.1E$^{-3}$ cm/s). In this exemplary implementation, the reinforced exemplary T3 sensor exhibited more favorable electrochemical properties, as shown from the enhanced voltammetric behavior in FIG. 4A.

Exemplary implementations were performed for exemplary printed T3 sensors for environmental/security monitoring applications. For example, in order to demonstrate the ability to operate in vapor-phase environments, an exemplary CF-modified T3 sensor was applied towards the detection of increasing levels of 2,4-dinitrotoluene (DNT) vapors. As such, the exemplary tattoo-based sensor was applied to a porcine skin sample, which was subsequently inserted in a sealed 15 mL container along with 100 mg of DNT salt. The system was allowed to equilibrate for 30 min, after which a calibration (with respect to time) was performed. The exemplary calibration data showed a high degree of linearity along with rapid response time. Repeated measurements were conducted, with the exemplary resultant data demonstrating precise repeatability. For example, maximum 6.9% deviation in the current level at the reduction peak (−1.05 V vs. Ag/AgCl) was observed across six independent measurements. For example, it is noted that vapor-phase detection is traditionally not feasible using bare SPEs due to the lack of a supporting electrolytic medium. However, the exemplary T3 electrochemical sensors exhibit a noteworthy structural difference when compared with conventional SPEs. For example, a perspiration-saturated adhesive polymer layer can be employed as the structural backbone, which may behave analogous to common hydrogel layers. Thus, the exemplary implementations demonstrated that the exemplary tattoo-based device is well suited to serve as a vapor-phase environmental sensor.

Figure 5A:
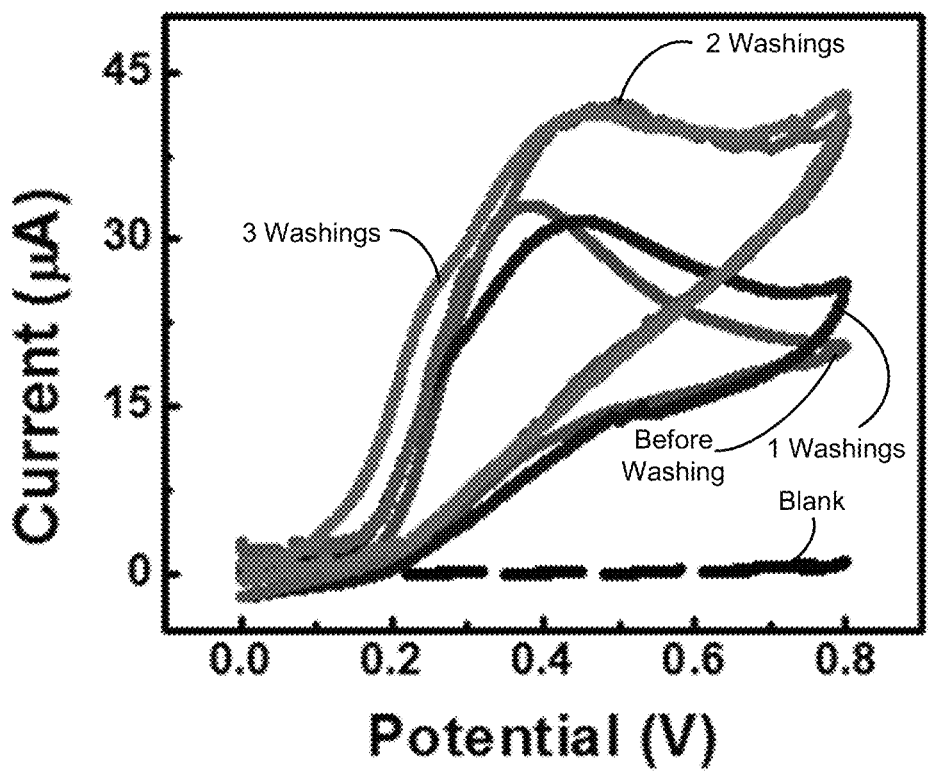
FIGS. 5A-5C show cyclic voltammogram data plots and images of exemplary electrochemical sensors.

The subjection of conventional SPEs on rigid and flexible substrates to repeated chemical and mechanical degradation is expected to have deleterious impact on their electrochemical behavior, thus precluding them from epidermal integration. Advantageously, for example, the disclosed T3 electrochemical sensors can rectify these challenges, e.g., through the inclusion of CFs in the ink matrix as well as through their strongly-adhesive (and flexible) backbone. Exemplary implementations were performed to evaluate the exemplary T3 sensors against chemical degradation, e.g. such as subjection to repetitive washing cycles (e.g., $t_{wash}$=5 s with hand soap) to emulate hand-washing or bathing. For example, the washing involved generating a thorough lather with hand soap under a continuous stream of tap water for 5 s and subsequently drying the skin sample with a towel. FIG. 5A shows an IV data plot showing the effect of repetitive washing cycles upon the CV waveform generated at the tattoo biosensor (on porcine skin) using 2.5 mM UA. As shown in FIG. 5A, although washing did impart relatively minor degradation in the waveform, e.g., shown from the well-defined peaks corresponding to the oxidation of UA. Additionally, for example, the peak current deviated from the baseline measurement (before washing) by no more than 15% at the conclusion of the implementations. Moreover, for example, an increase in the oxidation current following washing may reflect the exposure of a larger active electrode area. The peak potential, however, remained stable throughout the course of the implementations.

Figure 5B:
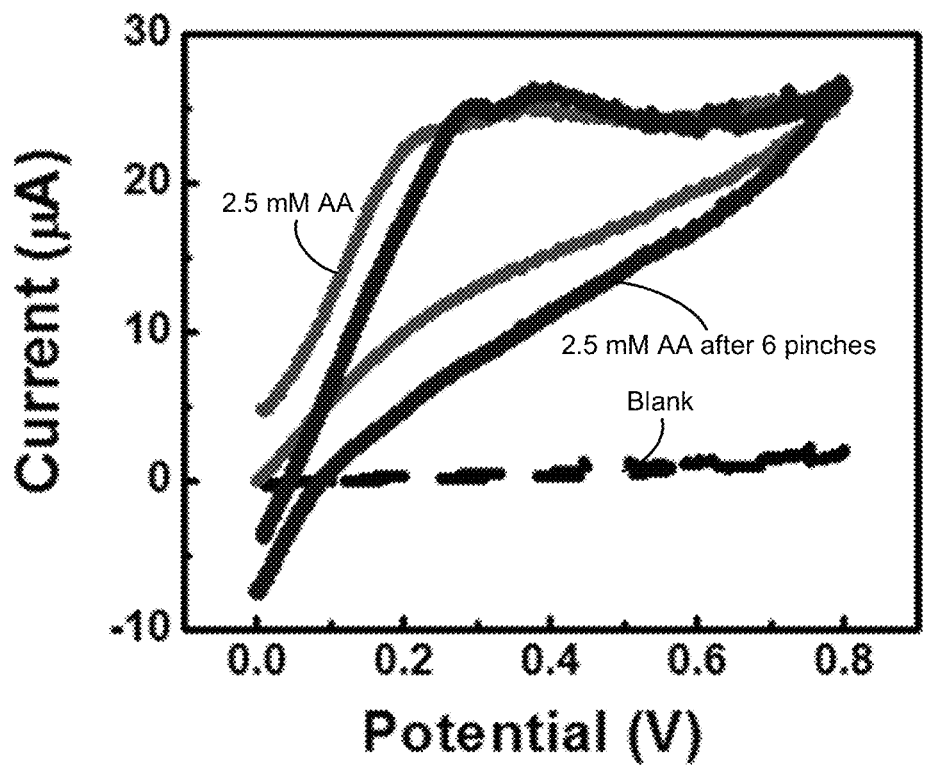

Exemplary implementations were performed to evaluate the effect of repetitive pinching of the tattoo patterned sensors. An exemplary CF-reinforced T3 sensor was applied to porcine skin and repetitively pinched for 2 s intervals, e.g., for six pinches. FIG. 5B shows an IV data plot displaying the response of the exemplary CF-reinforced T3 sensor to repetitive pinching operations employing 2.5 mM AA as a redox probe. The exemplary data indicate that repeated pinching of the sensor produced minimal degradation in the electrochemical performance. For example, both the peak current and peak potential remained stable throughout these pinching experiments, thereby demonstrating the capability of high-fidelity electroanalytical operations of the disclosed sensors under the severe demands imparted by epidermal wear.

Figure 5C:
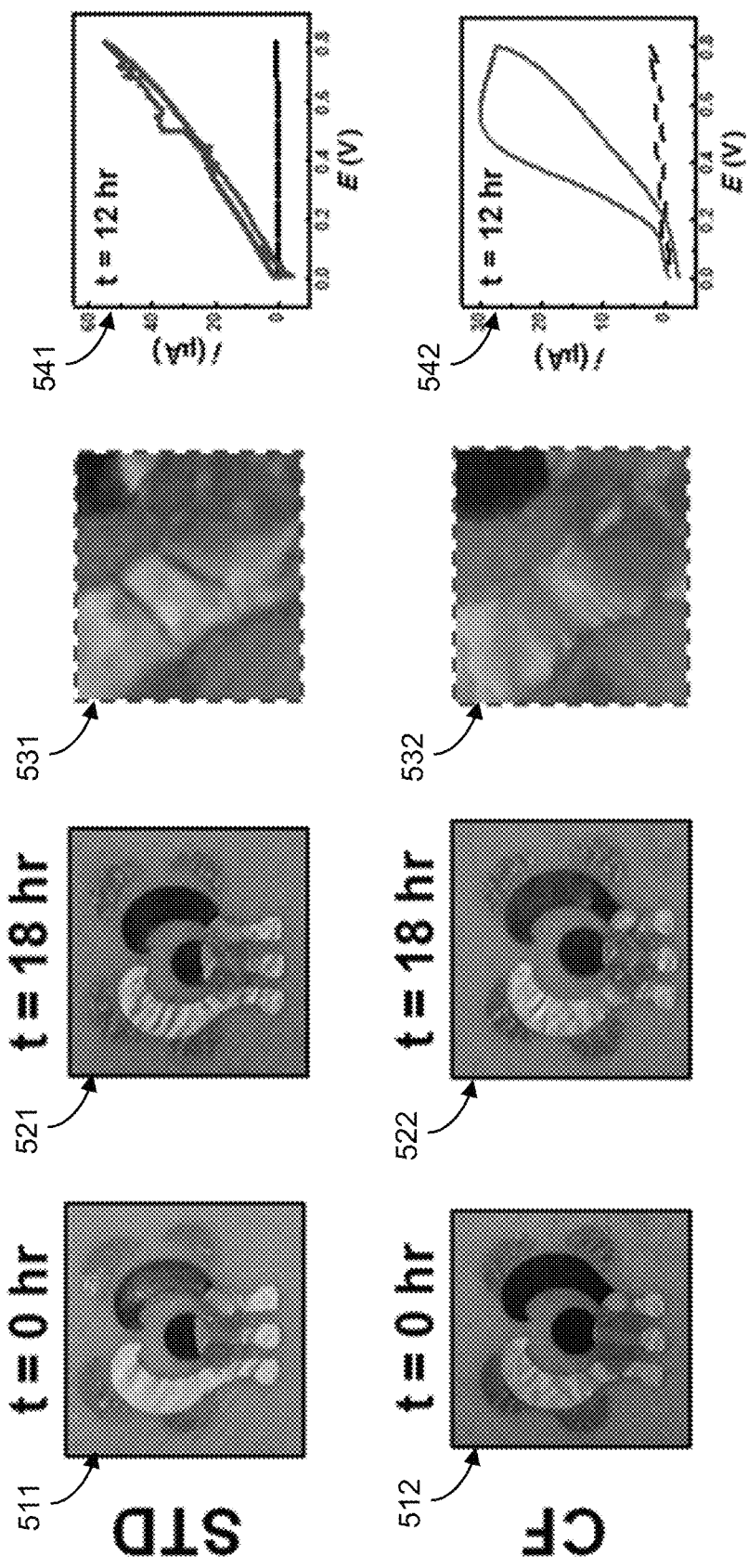

Exemplary implementations were performed with extended durations of routine wear of an exemplary T3 sensor. FIG. 5C shows images 511 and 512 captured immediately following the application of the T3 sensors on skin for an exemplary T3 sensor and an exemplary CF-reinforced T3 sensor, respectively, and images 521 and 522 captured after 18 hours of continuous epidermal wear of the exemplary T3 sensor and the exemplary CF-reinforced T3 sensor, respectively. A close inspection of the images 521 and 522 revealed some cracking (e.g., at the Ag/AgCl-insulator and carbon-insulator interfaces) for the exemplary T3 sensor without CFs, as shown in the image 531 of FIG. 5C, and substantially no cracking or degradation for the exemplary CF-reinforced T3 sensor, as shown in the image 532 of FIG. 5C. FIG. 5C also includes cyclic voltammogram data plots 541 and 542 for 0.5 mM UA at the exemplary T3 and CF-reinforced T3 sensors, respectively, following 12 hours of continuous wear of both sensors, e.g., with a scan rate of 100 mV/s. The response data recorded at the non-CF-reinforced sensor in the plot 541 exhibited substantial distortion, e.g., as compared to the well-defined anodic UA oxidation peak visible at the exemplary CF-reinforced sensor in the plot 541. A comparison with the voltammograms obtained from previous implementations with UA at unperturbed electrodes also corroborated that the exemplary CF-reinforced sensor is capable to yield high-fidelity electroanalytical performance over extended wear.

The disclosed technology includes techniques to the formation of biosensors and chemical sensors that exploit electrochemical detection methodologies such as amperometry, voltammetry, potentiometry, and electrochemical impedance spectroscopy. Thus, for example, exemplary techniques includes proper patterning of electrodes to form a complete electrochemical system, as well as the selection of an appropriate layering and ink formulation to facilitate the electrochemical response. The disclosed techniques can advance the field of non-invasive on-body continuous-monitoring biosensors.

For example, the majority of personal blood glucose monitors rely on disposable screen printed enzyme electrode test strips. These single-use electrode strips are mass produced by rapid and simple thick-film screen printing microfabrication techniques. Owing to its reliability and low cost, the diabetic monitoring industry has leveraged this fabrication concept for the past 30 years and has perfected the technology over this period such that analytically-precise results are now achievable, even when this fabrication methodology is migrated to the detection of other physiologically-relevant analytes such as metabolites, proteins, and DNA. The disclosed temporary transfer tattoo epidermal biosensing techniques enable the biosensor contingent to be transferred directly to the skin for the direct and non-invasive monitoring of the wearer's biochemical physiology and/or surrounding environment. For example, the exemplary biosensors can be transferred and include the ability to tolerate repeated bending and stretching operations typically associated with on-body wear, and its extended stability on the skin. For example, this paradigm can enable continuous monitoring of the wearer's biochemical physiology and/or surrounding environment, in direct contrast with state-of-the art invasive "single-shot" readings such as with blood glucose test strips for diabetics. In this manner, decreased overhead can be achieved, ultimately lowering the per-strip cost. Also for example, the biosensor pattern can be duplicated and arrayed as needed to parallelize the sensing operation, thereby yielding a substantially increased quantity of sensors per unit area.

In another aspect of the disclosed technology, techniques, systems, and devices are described for fabricating and implementing tattoo-based potentiometric ion-selective electrochemical biosensors and chemical sensors for epidermal and/or environmental monitoring on skin or a wearable item.

For example, the disclosed tattoo-based potentiometric ion-selective electrochemical biosensors and chemical sensors can include solid-contact ion-selective electrodes (ISEs) for non-invasive potentiometric monitoring of epidermal pH levels. The disclosed fabrication techniques of such devices includes the use of temporary transfer tattoo paper with screen printing techniques and solid-contact polymer ISE methods. The disclosed tattoo-based potentiometric sensors exhibit rapid and sensitive response to a wide range of pH changes with no carry-over effects. These tattoo ISE sensors are capable of enduring repetitive mechanical deformation, which is a key requirement of wearable and epidermal sensors. The flexible and conformal nature of the tattoo sensors enable them to be mounted on nearly any exposed skin surface for real-time pH monitoring of the human perspiration, as illustrated from exemplary response data acquired from exemplary implementations during strenuous physical activity.

Potentiometric ISEs have witnessed widespread use in various research, biomedical and industrial domains. Conventional ion-selective sensors include a membrane-based ion-selective electrode and a reference electrode, both of which require an internal solution to ensure a stable and sensitive response. Although these sensors have been widely used in various applications, their intrinsic design imposes inherent limitations upon specific in vivo and ex vivo applications, particularly, for example, the internal solution complicates the fabrication process and limits their miniaturization.

The disclosed technology includes highly flexible and conformal integrated potentiometric sensors, compatible with the non-planarity and irregularities of the human anatomy and capable of enduring prolonged mechanical strain, which can be successfully implemented in epidermal chemical monitoring, e.g., including pH measurements.

The disclosed wearable electrochemical sensing devices include a conformal geometry that is compliant with skin and can withstand repeated mechanical stress while minimizing intrusion in the wearer's routine. In some implementations, the disclosed wearable electrochemical sensing devices can be configured as textile-based sensors for in the field monitoring of the environment and on-body monitoring, in which the textile-based sensors conform with the wearer's anatomy while enabling unobtrusive sensing. Such wearable devices can provide detection of both physiological and environmental analytes. The design configurations of the disclosed technology enable continuous contact of detectable analytes with the sensor surface while worn a user's body (e.g., on skin or a wearable item).

Figure 6A:
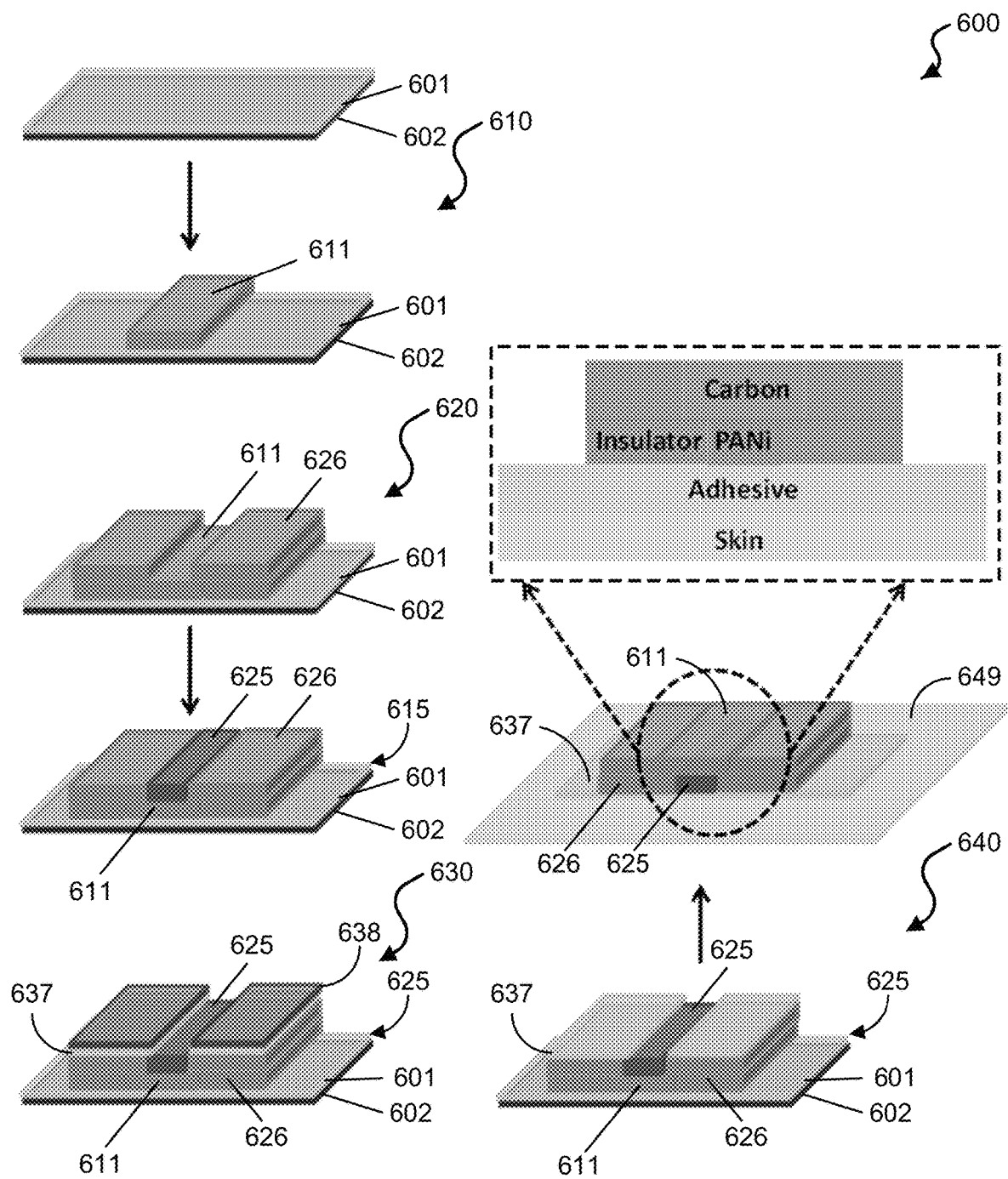
FIG. 6A shows a process diagram illustrating an exemplary fabrication protocol to produce epidermal electrochemical sensors of the disclosed technology.

In some implementations of the tattoo-based potentiometric devices, exemplary devices include polyaniline-based solid-contact ISEs and temporary transfer tattoo paper, and can be fabricated using hybrid screen printing techniques. FIG. 6A shows a process diagram illustrating a fabrication method 600 to produce epidermal electrochemical sensors with ion-selective electrodes. The method 600 includes a process 610 to form electrode structures 611, e.g., such as carbon-based material electrodes, by using thick-film screen printing on a release agent layer 601 coated over a base paper substrate 602. For example, the electrode structures 611 can be patterned on the release agent 601-coated paper substrate 602, in which the electrode pattern is configured in a particular design layout. The method 600 includes a process 620 to form electrically insulative material 626 and poly(aniline) (PANi) 625 to form a temporary transfer tattoo solid-contact ISE sensor 615. The method 600 includes a process 630 to form an adhesive sheet 637 with a protective coating 638 to the T3 ISE electrochemical sensor component 615 to form a T3 ISE electrochemical sensor device 625, which is capable of attaching to skin (or a wearable item) for one of sensing analytes in the external environment of the skin or fluids present on the skin. In some implementations of the method 600, a process 640 can include removing the protective sheet 638 from the adhesive sheet 637 of the T3 ISE electrochemical sensor device 625 to enable transfer of the T3 ISE electrochemical sensor device 625 on a receiving surface 649, e.g., including skin or a wearable item An inset illustrative schematic of the applied T3 ISE electrochemical sensor device 625 on the receiving surface 649 (e.g., skin) shows the layers of materials of the exemplary device.

Figure 6B:
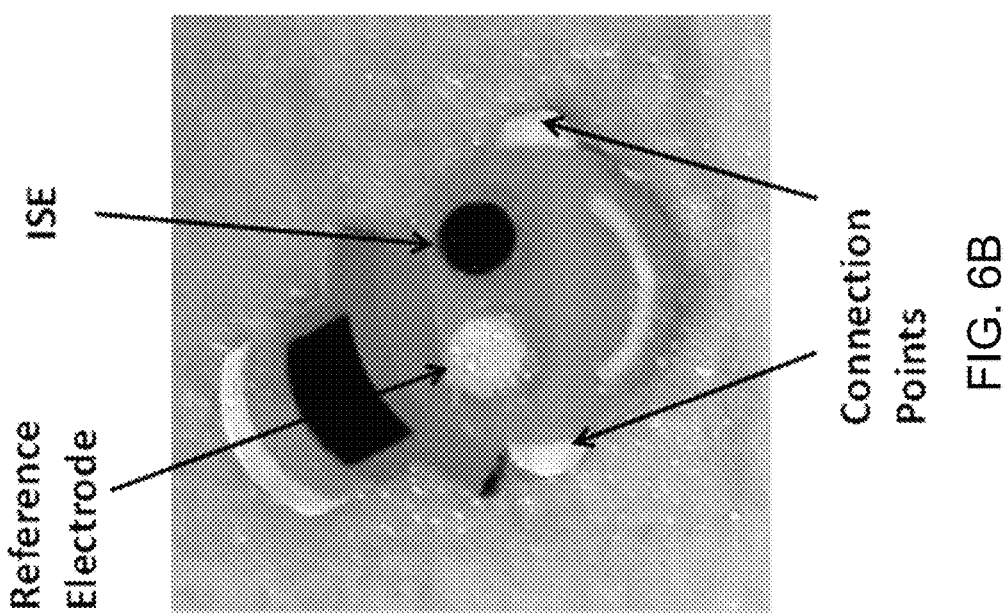
FIG. 6B shows an image of an exemplary ion-selective electrode (ISE) based tattoo sensor of the disclosed technology.

FIG. 6B shows an image of an exemplary ISE tattoo sensor including two electrodes, e.g., including an ISE and a reference electrode, and connection points that can interface with a voltmeter, for example, via electrically conductive conduits. For example, the disclosed fabrication methods allow development of the exemplary ISE tattoo sensors in a variety of designs, e.g. such as the 'smiley face' design of the exemplary ISE tattoo sensor shown in FIG. 6B. In this example, the sensor design includes one 'eye' of the smiley face acting as the pH-sensitive ISE while the other 'eye' functions as the reference electrode, e.g., thus concealing the complete sensor contingent in an artistic manner.

These exemplary 'smiley face' shaped-tattoo sensors can be readily fabricated using tattoo base paper, electrode inks, e.g., including carbon and/or Ag/AgCl, and insulator inks, in which the tattoo sensor fabrication employs a distinct stencil pattern for each layer. An adhesive sheet can later be applied to the electrode- and insulator-printed tattoo paper for subsequent transfer on various substrates. For example, poly (aniline) (PANi) exhibits pH-sensitive conductivity, e.g., demonstrated with the reversible emeraldine salt (ES)-emeraldine base (EB) transition (acid-base reaction), and can thus be used in the disclosed solid-state pH electrochemical sensors. Additionally, for example, PANi has minimal cytotoxicity and causes negligible skin irritation and sensitization. Thin films of PANi can be produced on the patterned electrodes or other structures of the disclosed devices via electropolymerization techniques with high reproducibility, and in doing so, for example, the fabrication of these exemplary PANi-based ISEs do not require surface pre-treatment. These characteristics along with the attractive performance make PANi well-suited for the disclosed biocompatible, epidermal tattoo-based potentiometric sensors. The resulting tattoo ISE sensor devices can withstand repeated bending and stretching operations, which are of substantial relevance to wearable epidermal sensors.

Exemplary implementations of the disclosed potentiometric ion-selective electrochemical sensor technology were performed, which included the described materials, procedures, and data.

The exemplary implementations described herein included the use of the following materials and equipment. For example, potassium phosphate monobasic ($KH_2PO_4$), potassium phosphate dibasic ($K_2HPO_4$), hydrochloric acid (HCl), Nafion® 117 solution, aniline and citric acid were obtained. Aniline was further purified by double distillation prior to use. Carbon fibers (8 µm diameter, 6.4 cm length, 93% purity) were obtained and their length was reduced to ~0.5 mm (e.g., by cutting with a sharp blade), followed by thorough cleaning in acetone. The exemplary implementations were conducted at room temperature, and solutions were prepared using ultra-pure deionized water (18.2 MΩ·cm). For example, electrochemical cleaning, deposition, and potentiometric analysis were performed using a CH Instrument (Austin, Tex.) model 630C electrochemical analyzer. A Mettler Toledo (Columbus, Ohio) S20 SevenEasy glass-electrode digital pH meter was employed for pH measurements, for example. A miniaturized multimeter (Sinometer MS8216 DMM) was used for on-body measurements in the exemplary implementations.

Exemplary ISE tattoo sensor devices were designed to conceal the electrodes in a 'smiley face'. The design included one eye functioning as the pH-sensitive ISE while the other eye functioning as the reference electrode. As exemplified in FIG. 6B, the two ears of the exemplary ISE tattoo sensor device were employed as connectors for attachment to a digital multimeter. For example, design of the exemplary smiley face sensor pattern was performed in AutoCAD (Autodesk, San Rafael, Calif.) and fabricated on 75 μm thick stainless steel and mesh stencils (Metal Etch Services, San Marcos, Calif.). For example, a unique stencil pattern was used for each electrode layer (e.g., including a carbon layer, an Ag/AgCl layer, and an insulator material). For example, the conductive Ag/AgCl ink (E2414), the carbon ink (E3449), and the insulator ink (E6165) were obtained, and an exemplary transparent dielectric ink (5036) was obtained. Carbon fiber segments were dispersed within the semi-conductive carbon ink matrix to increase the tensile strength of the electrode. Printing was accomplished via an MPM SPM semi-automatic screen printer (Speedline Technologies, Franklin, Mass.). Blank temporary transfer tattoo paper and the accompanying adhesive substrate were used without further derivation.

In some implementations of the method 600, a fabrication process can first involve the printing of the blue insulator ink, followed by the Ag/AgCl ink and the carbon ink, and finally, by another blue insulator layer. Following each routine, for example, the ink can be cured, e.g., such as at conditions including 90° C. for 15 min. Subsequently, for example, a 30 wt % KCl-doped transparent insulator can be screen printed only on the surface of the reference electrode and then cured, e.g., such as at conditions including 90° C. for 6 min. Finally, for example, a total of 6 μL of the 5% Nafion solution can be drop-casted on the Ag/AgCl reference electrode and left to dry, e.g., for an overnight duration. This exemplary fabrication process was implemented to produce an exemplary ISE tattoo sensor device used in subsequent implementations described.

In some implementations of the fabrication process, for example, prior to the electropolymerization of the aniline material, the working electrode was electrochemically cleaned by five cyclic voltammetric scans in 0.5 M HCl over the potential range of –0.3 V to 1.1 V (e.g., an external Ag/AgCl reference electrode and an external Pt wire auxiliary electrode were used in this processing step). Surface modification with PANi was performed in a 0.1 M aniline/1 M HCl solution by cyclic voltammetry from –0.2 V to 1.0 V (vs. Ag/AgCl) at 0.1 V/s. In such examples, electropolymerization was first performed for 12 cycles, then a fresh solution was dispensed on the surface, followed by additional 13 cycles. A total of 25 cycles were thus executed for the complete polymerization of the working electrode surface. During the exemplary cleaning and polymerization steps, in this example, the screen printed Ag/AgCl electrode was protected from the electrolyte solution to avoid its damage by highly acidic solutions and aniline. After air-drying the exemplary PANi film, the adhesive sheet was applied to the tattoo. For proper contact between the two electrodes and analyte solution, this adhesive sheet was excised to remove a rectangular-shaped region around the two electrodes (e.g., the two eyes). The as-prepared ISE tattoos were then ready for transfer and evaluation.

Exemplary implementations of the fabricated ISE tattoo sensor devices were examined in vitro by applying them onto hard plastic substrates prior to on-body epidermal studies. In some exemplary implementations, the tattoo ISE sensors were analyzed within the pH range of human sweat (e.g., pH 3-7, with a mean around pH 5) using standard McIlvaine's buffers. For example, since human perspiration can exhibit continuous fluctuations of pH, a practical pH sensor must encompass a rapid and near-instantaneous response to pH modulations over this range.

Figure 7A:
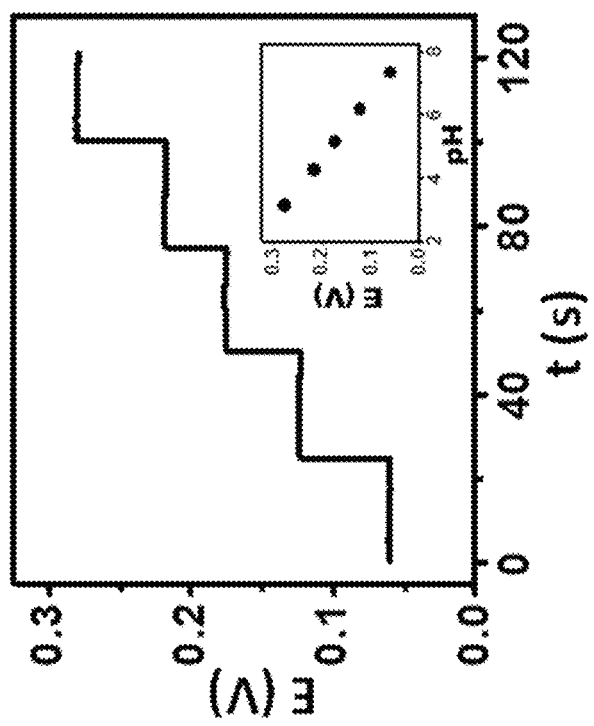
FIG. 7A shows a data plot of the potential-time response of an exemplary ISE tattoo sensor for decreasing pH levels.

FIG. 7A shows a data plot of the potential-time response of an exemplary ISE tattoo sensor for decreasing pH levels and an inset plot of electrical potential versus pH, e.g., using the standard McIlvaine's buffers. The data plot of FIG. 7A displays a characteristic potential-time recording at the exemplary tattoo-based potentiometric sensor for decreasing pH levels between 7 to 3 (in one-unit decrements). This real-time recording illustrates that the disclosed ISE tattoo sensors exhibit a nearly instantaneous response to varying pH solutions, e.g., yielding 80% of their steady-state signal within the first 10 sec while a completely stabilized signal was observed within 25 sec. The resulting calibration plot (shown in the inset of FIG. 7A) displays a sub-Nernstian behavior, e.g., with a mean slope ($s_x$) of 50.1 mV/pH and a relative standard deviation (RSD) of 3.72% (n=4). The pH sensitivity (slope) and conductivity of PANi depend on orientation of the crystalline and amorphous phases of PANi. The observed sub-Nernstian response of the PANi tattoo sensors can be attributed to inferior orientation of these phases. As discussed later, mild mechanical deformations to the ISE tattoo sensor devices caused reorientation of the conducting and amorphous phases and improved the pH-sensitivity to a near-Nernst response. Batch-to-batch variations between the tattoos also exhibited a low RSD of 4.63 (n=4), hence indicating the capability of the described fabrication techniques to produce reproducible devices.

It has been observed that the pH of human perspiration fluctuates according to the respiration rate. As such, the exemplary ISE tattoo sensor devices must also exhibit minimal carry-over in order to monitor such dynamically-fluctuating pH environments. To investigate this parameter, the ISE tattoos were subjected to operation in varying pH solutions and consecutive measurements recorded without reconditioning or rinsing of the tattoo surface.

Figure 7B:
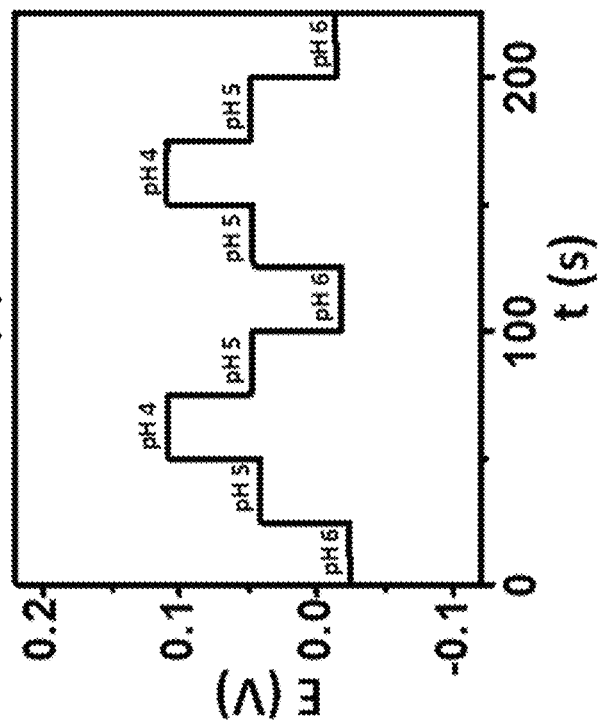
FIG. 7B shows a data plot of the potential-time response of an exemplary ISE tattoo sensor for large pH fluctuations.

FIG. 7B shows a data plot of the potential-time response of the exemplary ISE tattoo sensors, which demonstrates the reproducibility of the sensors in response to large pH fluctuations. The data plot of FIG. 7B demonstrates the dynamic response of the exemplary tattoo ISE sensor devices to alternate and multiple exposures to solutions of different pH. The exemplary device responded rapidly and favorably to these dynamic pH changes, regaining rapidly the same potentiometric signal for a given solution pH during this continuous operation. The negligible carry-over of the exemplary tattoo-ISE response reflects the fact that the emeraldine salt (ES)-emeraldine base (EB) transition of PANi is fast and reversible. Thus, the tattoo sensors have the capability to perform effectively under continuously-varying pH milieu, viz., in situ pH measurement of human perspiration with low early-over.

A distinctive feature of wearable sensors is their ability to endure prolonged mechanical strain, which is a key requirement of wearable and epidermal sensors. This is especially true in the sports, athletics, fitness and military domains. Exemplary implementations of the fabricated ISE tattoo sensor devices were performed to examine the influence of relevant mechanical stress upon the sensor performance prior to their integration with the epidermis.

For example, the influence of mechanical strain permutations, including repeated bending and stretching, upon the potentiometric response were examined. In some examples, the exemplary ISE tattoo sensor devices were subjected to a total of 50 bending and 40 stretching applications. For these exemplary implementations, the tattoos were transferred onto GORE-TEX as its viscoelastic behaviour mimics that of skin. In the bending implementations, the tattoo was bent to 180° and maintained at that position for 5 sec prior to release. The response of the tattoo was measured subsequent to 10 bending iterations from pH 7 to 3. The effect of stretching upon the electrochemical performance of the tattoos was analyzed. In the stretching implementations, the exemplary ISE tattoo sensor devices were stretched an additional 10% in lateral extent and maintained at that position for 5 sec followed by release and investigation of the response. In cases of stretching deformation, the response was measured at an interval of 5 consecutive stretching operations.

Figure 8A:
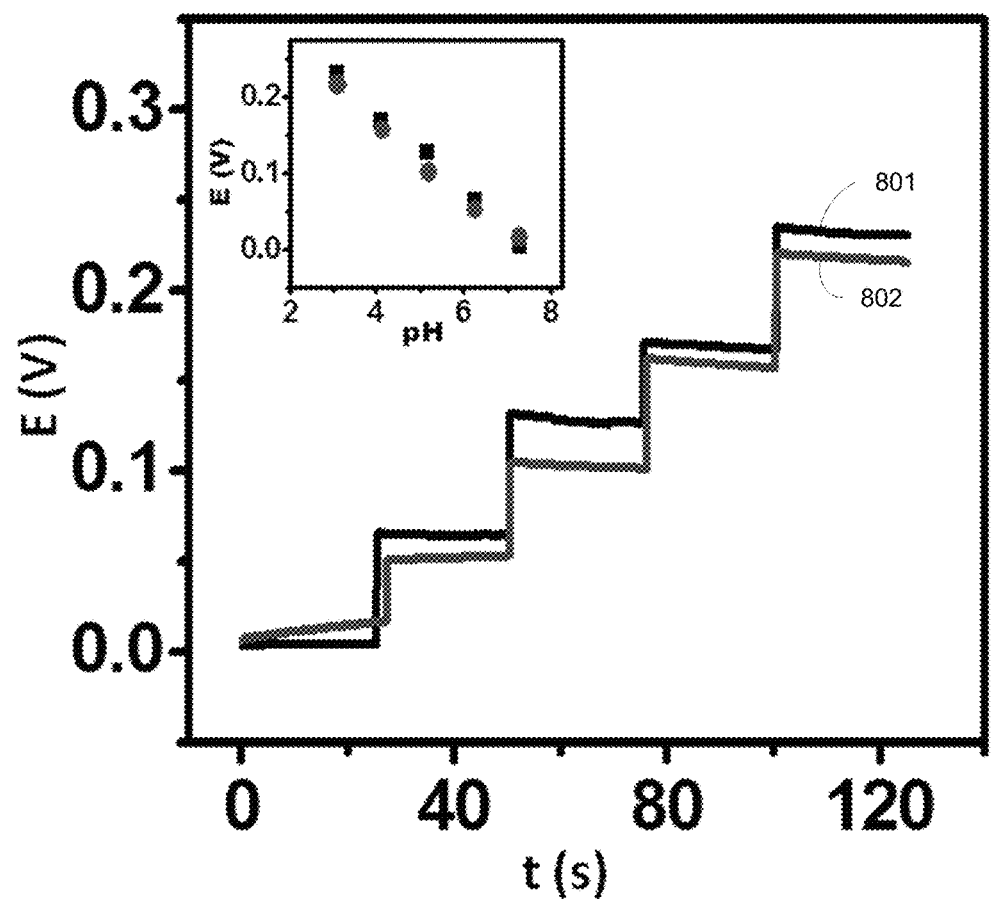
FIGS. 8A and 8B show a data plot and images representing the influence of repeated bending of an exemplary tattoo ISE device.
Figure 8B:
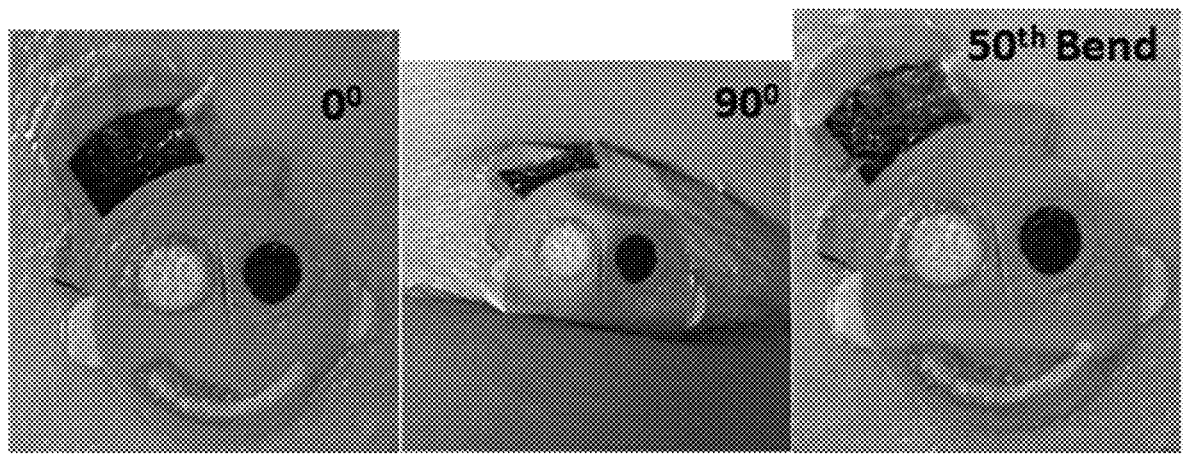

FIGS. 8A and 8B show a data plot and images representing the influence of repeated mechanical strain (e.g., bending) upon the response of an exemplary tattoo ISE device. The data plot in FIG. 8A shows the pH-responsive behavior of the exemplary ISE tattoo sensor over the 3-7 pH range prior to stretching (black waveform 801 and black squares in the inset plot) and following the $50^{th}$ bending on GORE-TEX (red waveform 802 and red dots in the inset plot), e.g., one unit pH decrement per addition. The images of FIG. 8B show the exemplary tattoo ISE sensor device applied to the cubital fossa at 0° bending, 90° bending, and after the $50^{th}$ bending.

Figure 9A:
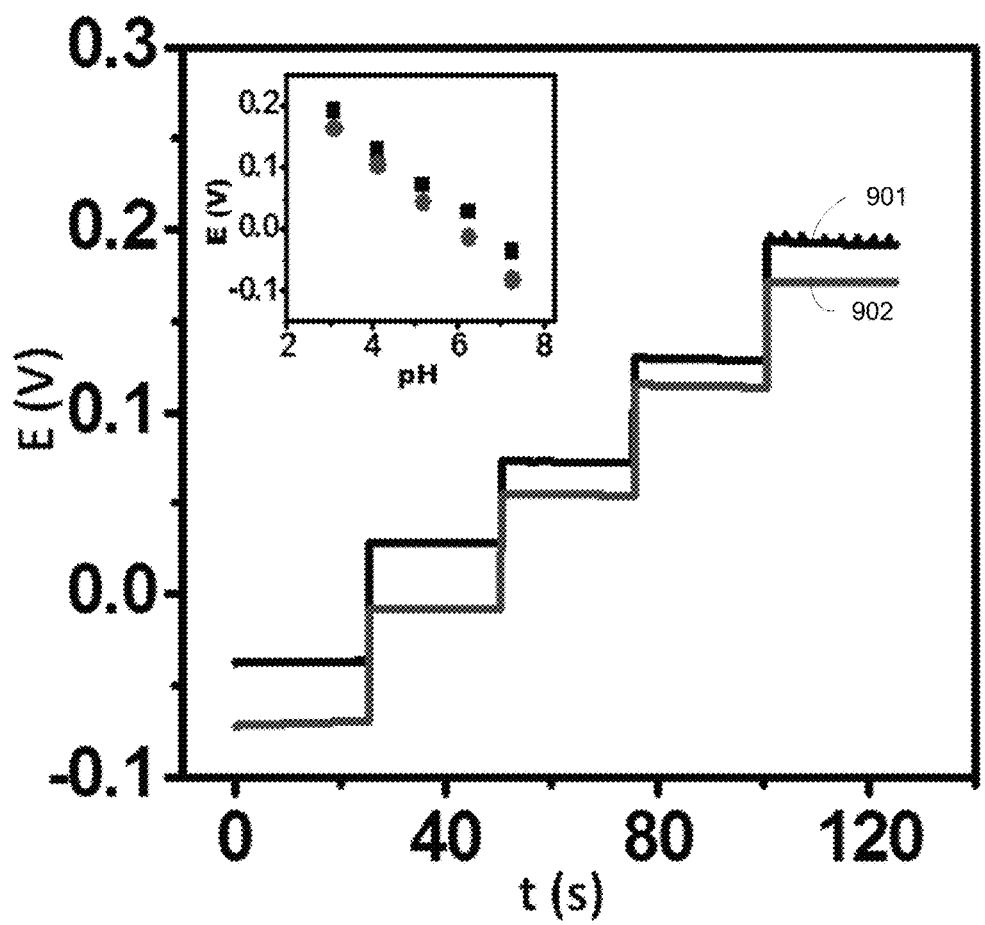
FIGS. 9A and 9B show a data plot and images representing the influence of repeated stretching of an exemplary tattoo ISE device.
Figure 9B:
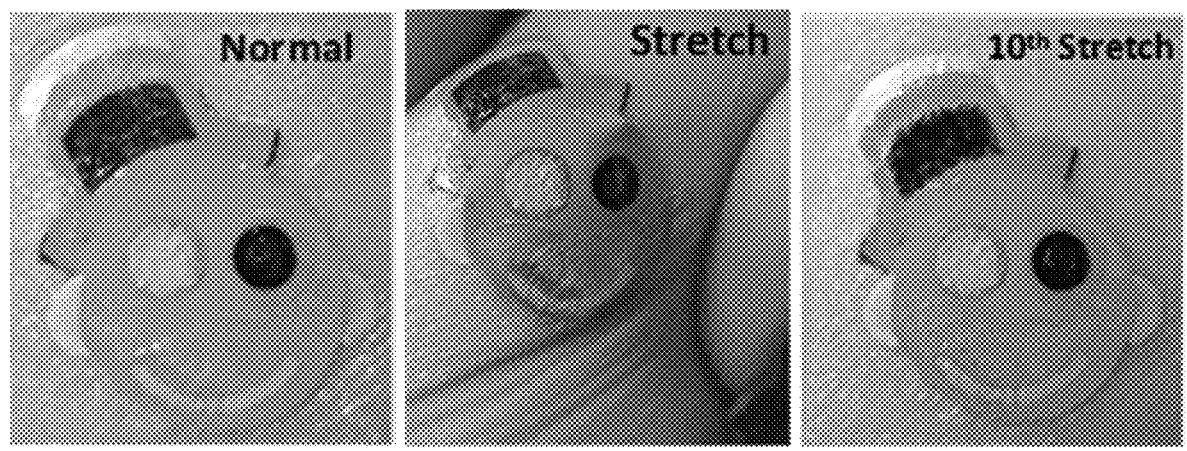

FIGS. 9A and 9B show a data plot and images representing the influence of repeated mechanical strain (e.g., stretching) upon the response of an exemplary tattoo ISE device. The data plot in FIG. 9A shows the pH-responsive behavior of the exemplary ISE tattoo sensor over the 3-7 pH range prior to stretching (black waveform 901 and black squares in the inset plot) and following the $40^{th}$ bending on GORE-TEX (red waveform 902 and red dots in the inset plot), e.g., one unit pH decrement per addition. The images of FIG. 9B show the exemplary tattoo ISE sensor device applied to the forearm at normal, after the $1^{st}$ stretch, and after the $10^{th}$ stretch.

It is noted, for example, the deformation created during these exemplary implementations of the exemplary tattoo ISE sensor device utilized yielded a beneficial effect upon the response of the sensor. Specifically, for example, in the absence of applied deformation, the exemplary tattoo ISE sensor device yielded a sub-Nernstian response (e.g., 52.8 mV/pH), e.g., as observed with plastic substrates. The response of the exemplary tattoo ISE sensor device improved to 59.6 mV/pH within the first 10 bending iterations (as shown in the data plot of FIG. 8A). Thereafter, the response stabilized to yield a final slope of 57.5 mV/pH following the $50^{th}$ bending iteration. The RSD for the entire exemplary implementation was 5.71%. A similar trend was observed for the stretching implementations, e.g., where an initial slope of 53.0 mV/pH increased to 58.2 mV/pH following the $10^{th}$ stretching iteration and finally stabilized at 57.54 mV/pH after the $40^{th}$ stretch (as shown in the data plot of FIG. 9A). A 4.72% RSD was obtained in this exemplary case. The sensitivity enhancement observed may be attributed to uncoiling and reorientation of the crystal and amorphous phases of PANi and the subsequent improvement in its conductivity owing to mechanical deformation.

Visual analysis of the exemplary tattoo ISE sensors under bending and stretching were performed on the human skin. For the bending studies, for example, the exemplary tattoo ISE sensor device was applied to the cubital fossa and the arm was bent completely until the fingers touched the scapula acromion, thus simulating the extreme deformation expected under heavy epidermal wear (as shown in the images of FIG. 8B). In the stretching scenario, for example, the exemplary tattoo ISE sensor device was applied to the forearm and then stretched repeatedly to the maximum extent (as shown in the images of FIG. 9B). These images reveal that the potentiometric sensors are quite resilient and that their structural integrity does not easily degrade. Accordingly, the exemplary tattoo ISE sensor device are well-suited for applications involving continuous motion of the substrate, e.g., as normally experienced by the human body.

There are growing demands for ion-selective sensors in the medical, sports, athletics, and fitness fields where point-of-care devices for the monitoring of physiological conditions are required. Electrolytes (e.g., such as Na, Cl, K, and/or Mg) and pH levels of perspiration can readily yield information regarding the metabolic state of an individual as well as their respiration dynamics during a fitness routine. Thus, continuous pH analysis of human perspiration is of great importance in the areas of clinical diagnostics and sports medicine.

Exemplary implementations of the exemplary tattoo ISE sensor devices were performed to demonstrate such continuous, real-time physiological monitoring under various conditions. Exemplary tattoo ISE sensor devices were applied to different locations throughout the body (e.g., the neck, wrist and lower back) of an active, consenting volunteer (sex: male; age: 27; weight: 70 kg; height: 186 cm) while the multimeter readout unit was attached to the body using a commercially-available arm-band. For example, the multimeter leads were attached firmly to the connection points (e.g., the designed 'ears') of the exemplary tattoo ISE sensors using transparent tape. The elasticity of the tattoo substrate allows the exemplary potentiometric sensor to attach firmly to these different body locations. In these exemplary implementations, for example, the neck, wrist, and lower back areas were selected in order to vary operational conditions experienced by these sensors, as mechanical stress and local pH are expected to vary among these locations.

For example, the ISE application process and the subsequent mating of the sensor with the readout instrument required less than 5 min and was readily performed by the subject. During the experiment the subject used a stationary cycle in a gymnasium for a total of 40 min followed by a 10 min gradual cool down. The subject ingested no fluid (dehydrated state) during the entire exercise. Heart rate and cadence were maintained around 165 and 130 RPM, respectively. pH sensing of the subject's perspiration was performed by the exemplary ISE tattoo sensor devices and the data were collected at regular intervals using the miniaturized multimeter. To confirm that the tattoos yielded accurate readings, the regional pH was verified using a conventional pH meter and glass electrode.

Figure 10A:
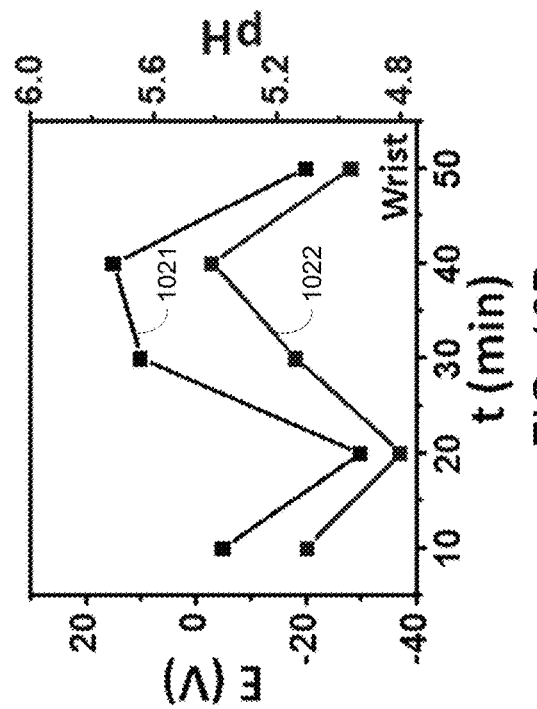
FIGS. 10A-10C show data plots of the potential-time response of exemplary ISE tattoo sensors applied to a subject's neck, wrist and back to detect pH changes from perspiration.

FIG. 10A shows a data plot of the real-time voltage-time response of an exemplary ISE tattoo sensor applied to a subject's neck to detect pH changes (shown as waveform 1011), e.g., as compared to that of a conventional pH meter (with response shown as waveform 1012).

Figure 10B:

FIG. 10B shows a data plot of the real-time voltage-time response of an exemplary ISE tattoo sensor applied to a subject's wrist to detect pH changes (shown as waveform 1021), e.g., as compared to that of a conventional pH meter (with response shown as waveform 1022).

Figure 10C:
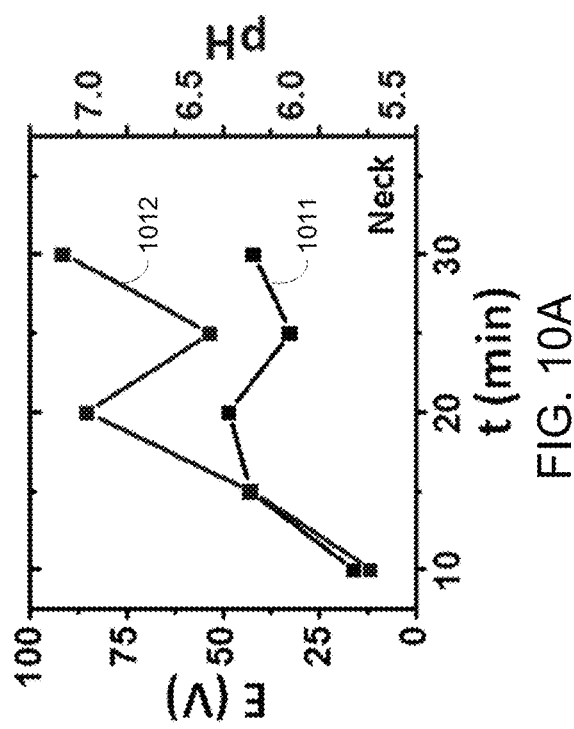

FIG. 10C shows a data plot of the real-time voltage-time response of an exemplary ISE tattoo sensor applied to a subject's lower back to detect pH changes (shown as waveform 1031), e.g., as compared to that of a conventional pH meter (with response shown as waveform 1032).

Figure 10D:
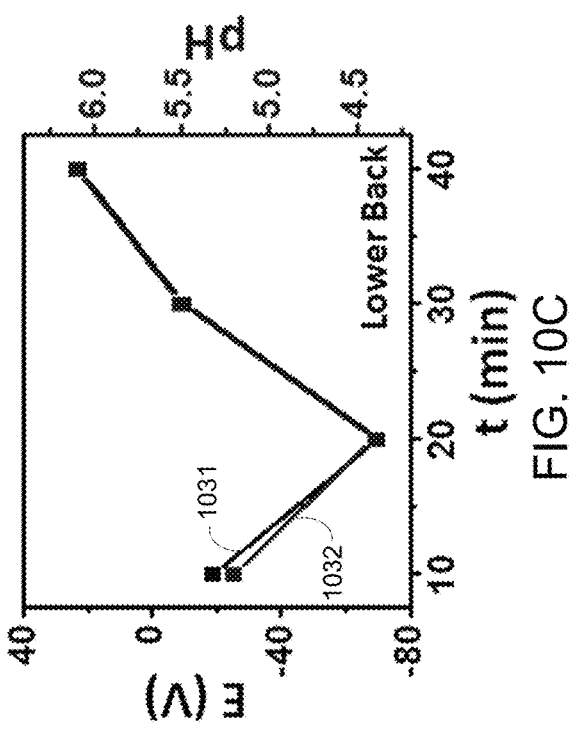
FIG. 10D shows an image of an exemplary ISE tattoo sensor device attached to a user's wrist for the epidermal measurements of pH in human perspiration.

FIG. 10D shows an image showing the exemplary device used in these exemplary implementations (e.g., the tattoo ISE sensor interfaced with a digital multimeter) attached to the subject's wrist for the epidermal measurements of pH in human perspiration.

Although an athlete initially perspires at a low rate, this is soon followed by heavier perspiration as physical activity continues. Thus, an important requirement for such tattoo sensors is their ability to yield precise readings during a wide range of sweat flow rates. It was observed that during the first 10 min of exercise, the exemplary ISE tattoo sensor devices provided no response as the amount of perspiration generated was not sufficient to record a consistent open circuit potential. This was also true for the pH glass electrode. However, at the 10 min mark, sweat excretion became sufficient for the tattoo sensors to yield a stable reading. Initially, the pH measured at the three positions (e.g., the neck, wrist, and lower back) by the tattoo ISE sensors were almost the same (e.g., ~pH 5.3), as shown in FIG. 10A-10C.

In this exemplary implementation, the real-time sweat pH data obtained from the exemplary ISE tattoo sensor devices can be explained based on varying sweat rate at the respective body parts. The exemplary subject perspired most profusely in the vicinity of the neck, followed by the lower back and the wrists. As the sweat excretion rate increases, the relative concentration of lactate and pyruvate decreases due to dilution, and the pH concomitantly increases. The data plots of FIGS. 10A-10C illustrate that the exemplary ISE tattoo sensor devices performed favorably with a mean slope of ~54 mV/pH, and their potentiometric response at the different body locations followed closely the pH values recorded with the glass electrode.

During the entire course of the exemplary implementation, it was observed that the exemplary ISE tattoo sensor devices performed well during both moderate and profuse perspiration. However, owing to the combination of excessive sweating and the highly curvilinear morphology of the skin on the neck, the neck-based tattoo ISE sensor functioned reliably for about 30 min. It is also noted that the exemplary ISE tattoo sensor devices functioned satisfactorily even when minor cracks were observed (as long as connection to the multimeter was maintained). This can be attributed to the fact that the potentiometric response is independent of electrode area, e.g., which is in contrast to area-dependent voltammetric and amperometric type measurements.

In another aspect of the disclosed technology, techniques, systems, and devices are described for fabricating and implementing temporary transfer tattoo-based electrochemical biosensors for non-invasive monitoring of lactate in perspiration, e.g., in which the sensors are applied to skin or a wearable item.

Lactate is a key stress biomarker and has garnered substantial interest in the athletics field. Muscular fatigue is a major hindrance in an athlete's performance and thus extensive efforts are taken to improve one's stamina. This is especially true in intensive and endurance-based sports such as the triathlon, cycling, boxing etc. Lactate is widely recognized as an important biomarker of muscular exertion and fatigue and has been extensively utilized by coaches, exercise physiologists, and sports physicians to monitor an athlete's performance. When an individual engages in intense physical activity, the body makes the transition from aerobic to anaerobic respiration in order to satisfy the energy demands of the musculature. During this phase, the body consumes stored glycogen from the muscles to generate energy; an unwanted effect of this process is the production of lactate, which is associated with a burning sensation in the muscles. This process is known as "glycolysis" or "lactate acidosis". During glycolysis, the lactate levels in perspiration increases, as well. There exists a correlation between perspiration lactate and blood lactate, and therefore, perspiration can be used as the sample for the analysis of muscular exertion and fatigue in persons without the need for finger sticks or venipuncture.

The disclosed technology includes fabrication methods to produce temporary transfer tattoo electrochemical sensing devices for non-invasive enzymatic detection and quantification of lactate in human perspiration. Implementation of the disclosed T3 sensors can provide crucial insight into an athlete's metabolic response to controlled physical activity by offering critical insight into the temporal dynamics of lactate concentration in the perspiration. Currently, the gold-standard for lactate monitoring in the fitness, athletics, and sports domains is the use of blood lactate sensors, which are enzyme-functionalized electrochemical strips requiring fingerstick blood samples, akin to blood glucose readings. The present blood lactate sensors show high sensitivity and selectivity towards lactate and are successful in detecting it within 5-15 seconds. However, a major drawback inherent to these sensors is their invasiveness and sample collection methodology. Furthermore, to obtain a detailed lactate profile, the blood is usually collected at a coarse interval of few minutes while the athlete engages in rigorous training, which invariably hinders performance. A non-invasive lactate sensor offering higher temporal resolution is thus highly desired.

The disclosed techniques for real-time non-invasive lactate sensing in human perspiration use the described printed electrochemical temporary transfer tattoo biosensors. These exemplary enzymatic T3 electrochemical biosensors are capable of adhering to the epidermis and demonstrate resiliency against continuous mechanical deformations common to epidermal wear. The biosensors can be implemented for real-time, on-body analysis for the detection and quantification of lactate in perspiration, e.g., during fitness and activity to provide useful insight into a user's health and athletic performance, in which the sensed data can be used for enhancing the athletic performance of the user.

Figure 11A:
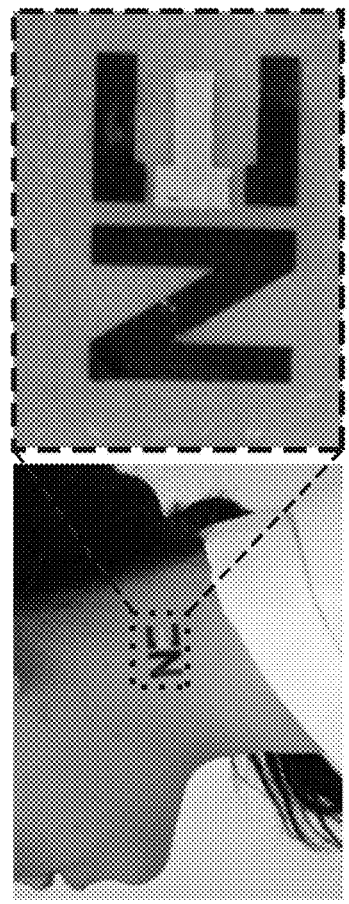
FIG. 11A shows a schematic illustration of an exemplary epidermal electrochemical sensor of the disclosed technology.

In some implementations, an exemplary enzymatic T3 electrochemical sensor device includes a working electrode, a counter electrode, and a reference electrode configured on a flexible electrically insulative material structured to adhere to the skin (or a wearable item) of a user. FIG. 11A shows a schematic illustration of an exemplary enzymatic T3 electrochemical sensor device including three electrodes (e.g., the working electrode, counter electrode, and reference electrode) configured in the design 'tattoo' design "NE" for electrochemical detection of L-Lactic acid.

Figure 11C:
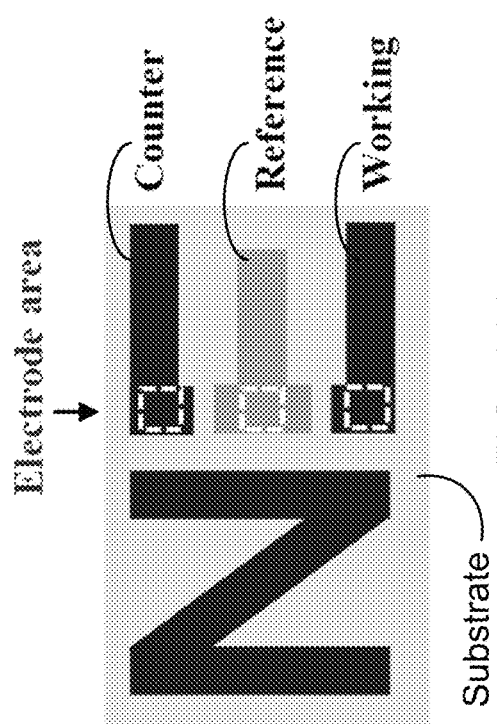
FIG. 11C shows an image of the exemplary epidermal electrochemical sensor of FIG. 11A implemented on a user's skin.
Figure 11B:
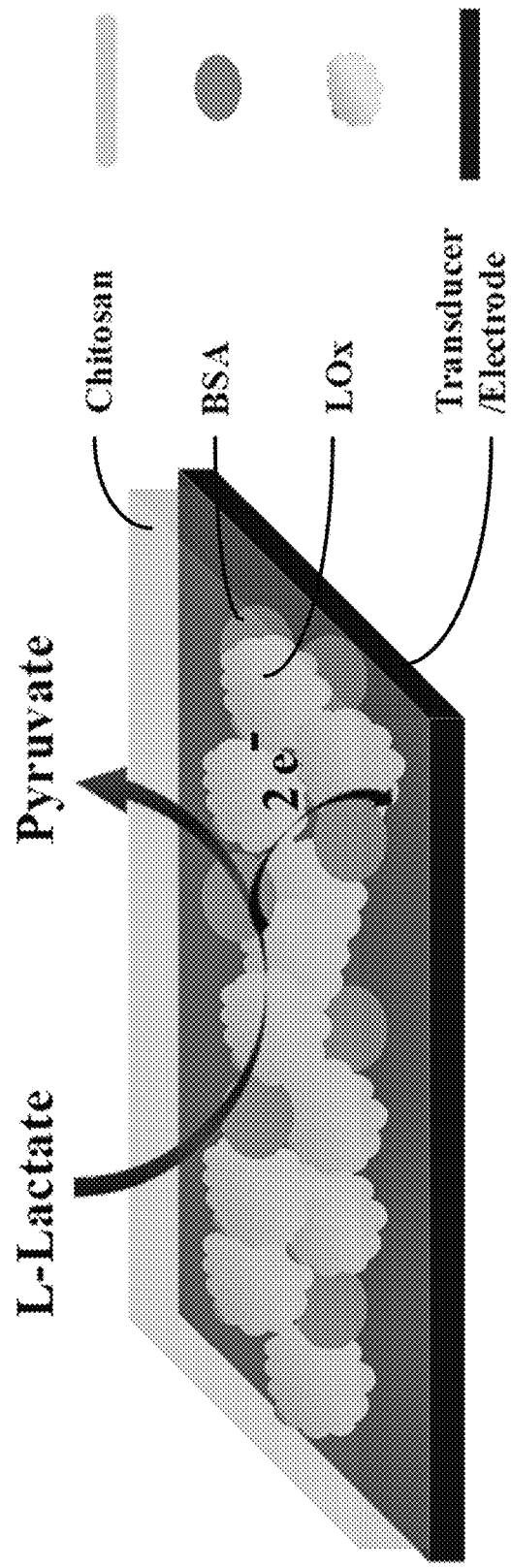
FIG. 11B shows an illustrative schematic of the functionality working electrode of the exemplary sensor of FIG. 11A.

The working electrode of the exemplary T3 sensor can be functionalized with monolayers, ligands, enzyme catalysts and/or electroactive redox mediators, among other molecules or substances to enhance the detectability of the target enzyme. For example, in the exemplary T3 sensor of FIG. 11A, the working electrode is functionalized with tetrathiafulvalene (TTF), an electroactive redox mediator, and multi-walled carbon nanotubes in order to tether the active site of lactate oxidase, e.g., an enzyme catalyst, to form an electrochemical transducer layer on the electrode surface of the working electrode. Also in this example, a layer of chitosan is deposited onto the enzyme-electrode to impede the efflux of the biocatalytic backbone from the electrode to the aqueous environment. FIG. 11B shows a schematic illustrating an exemplary modified working electrode including the transducer layer coated by biocompatible polymer (e.g., chitosan). Under this scheme, lactate diffuses through the chitosan membrane and is oxidized by LOx to pyruvate, releasing two electrons in the process, which give rise to an electrical current that can be measured between the working and counter electrodes.

For example, during bouts of physical exertion, the human body performs complex motions that cause the skin to undergo extreme mechanical deformations. Hence, wearable devices must survive such harsh conditions without compromising their performance. The disclosed T3 electrochemical biosensors possess the capability to withstand repeated iterations of mechanical deformation. Additionally, the disclosed T3 electrochemical biosensors possess the specificity to detect the target analyte or analytes desired, e.g., from human perspiration. FIG. 11C shows an image of the exemplary enzymatic T3 sensor device transferred on human skin.

Exemplary implementations were performed using the disclosed enzymatic T3 electrochemical sensor devices applied to skin of human subjects for in-situ sweat lactate profile recordings and analysis. A comparison of the profiles with previously reported data substantiate that the lactate epidermal biosensor platform performs desirably under conditions typical of use, e.g., demonstrating their utility as a non-invasive technique to assess lactate levels in order to assess and affect physical performance.

The exemplary implementations of the disclosed enzymatic T3 electrochemical sensor technology included the described materials, procedures, and data.

The exemplary implementations described herein included the use of the following materials and equipment. For example, tetrathiafulvalene (TTF), glutaraldehyde solution (8%), chitosan, acetic acid, bovine serum albumin (BSA), L-lactic acid, sodium phosphate monobasic ($NaH_2PO_4$), sodium phosphate dibasic ($Na_2HPO_4$), D(+)-glucose, L(+)-ascorbic acid, uric acid and creatinine were obtained and utilized in the exemplary implementations. Additionally, L-Lactate oxidase (LOx) and carboxy-functionalized multi-walled carbon nanotubes (MWNTs) were also acquired and used. Exemplary reagents were used without further purification. Carbon fibers (CFs) (e.g., 8 μm diameter, 6.4 mm length, 93% purity) were obtained and further processing was performed to reduce their length to approximately 2 mm, for example, and the CFs were cleaned with acetone. Electrochemical characterization was performed at room temperature leveraging a CH Instruments (Austin, Tex.) model 1232A electrochemical analyzer.

Exemplary enzymatic T3 electrochemical sensor devices were designed in the shape of "NE" (e.g., acronym for "NanoEngineering"). An exemplary fabrication process, e.g., similar to that described in FIG. 6A, was employed. Briefly, for example, the fabrication of the exemplary "NE"-designed enzymatic T3 sensors included dispersing chopped carbon fibers within both semi-conductive carbon (E3449) and conductive silver ink (E2414), e.g., to a concentration of 1.5% and 1.2%, respectively, to increase the tensile strength of the electrodes. Corresponding stencil patterns were designed and used for printing each layer on tattoo base paper, following the sequence of carbon, silver and insulator, using an MPM-SPM semi-automatic screen printer (Speedline Technologies, Franklin, Mass.). As shown in FIG. 11A, the 'E' portion of the exemplary device includes a reference electrode (e.g., fabricated from the exemplary silver ink), and a counter electrode and a working electrodes (e.g., fabricated from the exemplary carbon ink). A transparent insulator was screen printed on top to confine the electrode areas. Following every screen printing step, the printed tattoo paper was cured at 90° C. for 15 min in a convection oven.

Upon the fabrication of the exemplary NE"-designed enzymatic T3 sensor device, the working electrode was further functionalized. For these exemplary implementations, MWNTs were first suspended in ethanol (e.g., 5 mg/mL), and sonicated for several hours until uniform suspension was achieved. The suspension was then mixed with 0.1 M TTF ethanol/acetone (e.g., 9:1 (v/v)) solution in a volume ratio of 2:1 and sonicated for 1 h. For example, 3 μL of MWNTs/TTF suspension was subsequently cast onto the open area of the working electrode. After the electrode completely dried, 3 μL of LOx solution (e.g., 40 mg mL$^{-1}$ with 10 mg mL$^{-1}$ BSA) was cast on the electrode and dried under ambient condition, and later covered with 2 μL of 1 wt % chitosan solution. The electrodes were then cross-linked with glutaraldehyde vapor overnight at 4° C.

The transfer process of the exemplary NE"-designed enzymatic T3 sensor device on a host surface (e.g., including human skin) was similar to the previously described process, for example, as in FIG. 6A, with minor modifications. For example, in these exemplary implementations, a void was maintained around electrode areas to facilitate the flow of perspiration among electrodes for the on-body tests. For the exemplary in vitro implementations, the exemplary NE"-designed enzymatic T3 sensor were applied to the host surface such that the bio-functionalized side faced upwards, while during the exemplary on-body implementations, the bio-functionalized side faced downwards (in direct contact with human skin).

The exemplary implementations included evaluating the electrochemical performances of the exemplary lactate T3 sensor in vitro by transferring it onto a rigid plastic substrate and/or onto a flexible GORE-TEX textile for mechanical integrity studies. These analyses were performed using 0.1 M phosphate buffer, pH 7.0. For example, the operation potential for the exemplary lactate T3 sensor was determined in vitro by applying linear sweep voltammetry with a scan rate of 1 mV/s from −0.2 to 0.2V using 8 mM L-lactate. The amperometric responses were recorded at a constant potential of 0.05 V for 60 s after 1 min incubation. In the exemplary stability implementations, for example, amperometric response to 8 mM L-lactate was conducted every 30 min for an 8 h-period. In between the exemplary implementations, the tattoo was kept at room temperature. For exemplary interference assessments, potential interferents with average concentration existing in human sweat were examined.

The exemplary implementations included evaluating the electrochemical performances of the exemplary lactate T3 sensor in on-body epidermal L-lactate sensing applications. For example, the exemplary implementations included healthy subjects asked to wear a tattoo lactate sensor on their deltoid in order to assess real-time lactate generation. The sensor was connected to the CHI analyzer using fine stainless steel wires, and the real-time lactate profile was recorded using amperometry (time interval: 5 s, potential: +0.05V). Subjects were asked to mount a stationary cycle, begin cycling at a steady, slow cadence for 10 min. Following this 'warm-up' period, subjects were instructed to cycle with an increasing resistance every 3 min until maximum he/she can reach. This process ensured that the anaerobic respiration threshold was attained, hence augmenting the excretion of lactate in the perspiration. Later subjects were asked to gradually reduce their cadence during a 10 min 'cool-down' period. The exemplary subjects ingested no fluid during the duration of the fitness routine. During the workout, blood lactate concentrations were measured using a commercial lactate sensor. The correlation between sweat and blood lactate concentration were analyzed.

As shown in FIGS. 11A and 11B, the exemplary lactate T3 electrochemical sensors included a functionalized working electrode forming a MWNTs/TTF/LOx/Chitosan matrix. For example, during high body activity, e.g., caused during sports, fat nutrition, stress, infections and/or organ malfunction, the usual aerobic metabolism is incapable of satiating the energy needs of the human body. In such times, the anaerobic process (glycolysis or lactate acidosis) is initiated wherein the stored glycogen is consumed to produce energy and lactate by muscle cells. The sweat lactate concentration is a function of glycolysis and sweat rate and changes continuously with time. Moreover, the lactate concentration of the human sweat depends on a person's metabolism and can vary between 3 mM to 50 mM. However, in most cases the sweat lactate concentration fluctuates within 3-25 mM. Thus a wide linear detection range coupled with fast response time is mandatory for an ideal sweat lactate sensor.

For example, in the case of lactate, typical lactate sensors are often based on two types of enzymes, lactate dehydrogenase and lactate oxidase. However, one must recognize that for LDH, $NAD^+$ must be employed as the cofactor, which represents a noteworthy challenge given that this molecule must be immobilized on the electrode to prevent it from leaching into the solution while being able to diffuse, with relative ease, to the enzyme's active site. The detection of lactate from LOx is usually at a high potential (>+0.65V). At such high potentials, other electroactive metabolites become active and lead to false data.

In the disclosed technology, for example, mediators, e.g., such as TTF, are used in the exemplary T3 electrochemical biosensors to achieve electrocatalytic conversion of L-lactate by LOx at lower potential, e.g., thus avoiding interference by other electroactive species. To further improve the efficiency of the exemplary lactate T3 sensors, MWNTs are dispersed together with mediator to serve as the electron transducer on the working electrode. Furthermore, given the aim of epidermal usage of the tattoo sensor, the tattoo was coated with a biocompatible chitosan layer that functions as physical barrier and limits the efflux of the catalytic backbone from the tattoo and onto the underlying skin. This exemplary functionalization scheme of the working electrode of the exemplary lactate T3 electrochemical sensor is shown in FIG. 11B.

Exemplary implementations of the exemplary lactate T3 electrochemical sensor devices were performed in in vitro applications. For example, linear sweep voltammetry was applied first in the presence and absence of L-lactate in buffer. In this example, the exemplary lactate T3 sensor showed a peak value around +0.05 V, e.g., indicating that the MWNTs/TTF/LOx/Chit exhibits selective catalytic ability towards the oxidation of L-lactate. The potential of +0.05 V was applied for all the following amperometric detections. The exemplary lactate T3 sensors were then implemented, for example, to identify the detection range and the response time. In this exemplary implementation, the LOx functionalized T3 devices were exposed to varying concentrations of lactate prepared using, for example, 0.1M sodium phosphate buffer (e.g., pH 7.0).

Figure 12A:
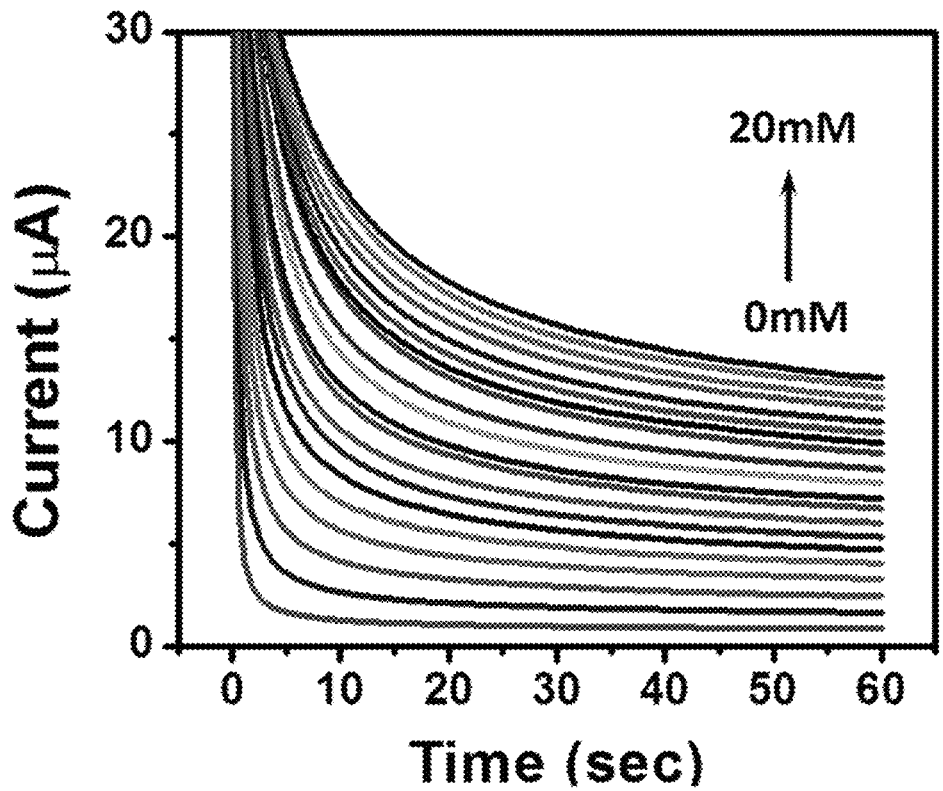
FIGS. 12A and 12B show amperometric data plots of the responses for concentrations of L-Lactate using an exemplary lactate T3 electrochemical sensor device.
Figure 12B:
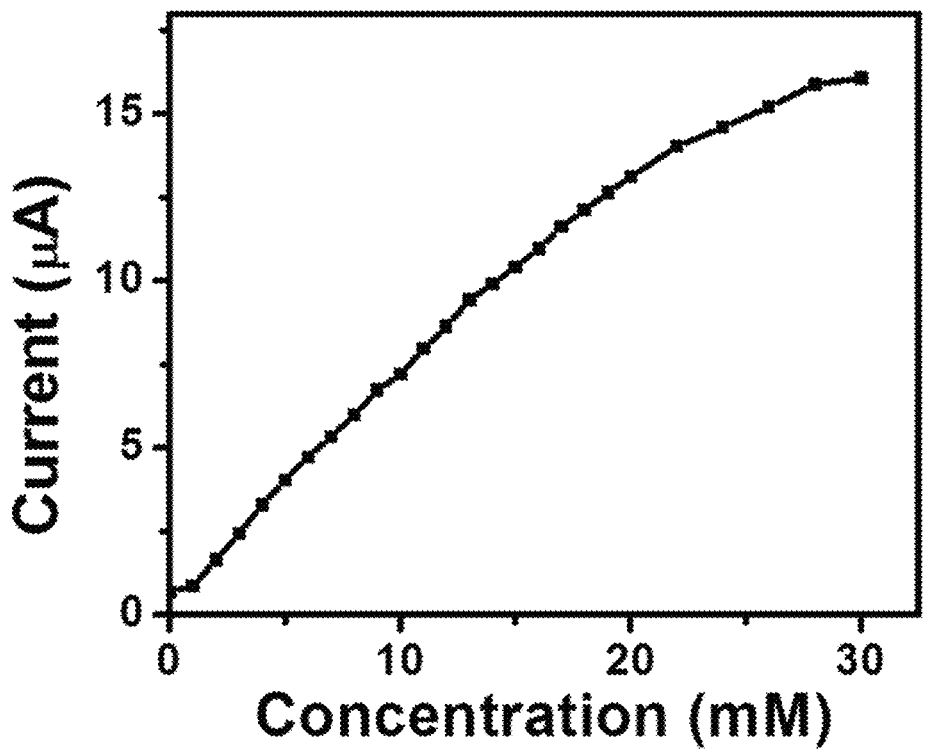

FIG. 12A shows an amperometric data plot of the responses for different concentrations of L-Lactate using the exemplary lactate T3 electrochemical sensor device, e.g., with 1 mM increment, $E_{applied}$=+0.05V. FIG. 12B shows the exemplary corresponding calibration plot of L-Lactate. As shown in FIG. 12A, the exemplary lactate T3 electrochemical sensors exhibited linear detection from 1 mM to 20 mM beyond which the signal gradually saturates with 644.2 nA/mM sensitivity and correlation (e.g., current (µA)=0.644 [L-lactate](mM)+0.689) between current and lactate concentration. For example, the large detection range and high sensitivity may be attributed to the high surface area provided by the MWNTs which can augment the enzyme loading capacity of the tattoos and the fast electron transfer between enzyme and transducer.

Figure 13A:
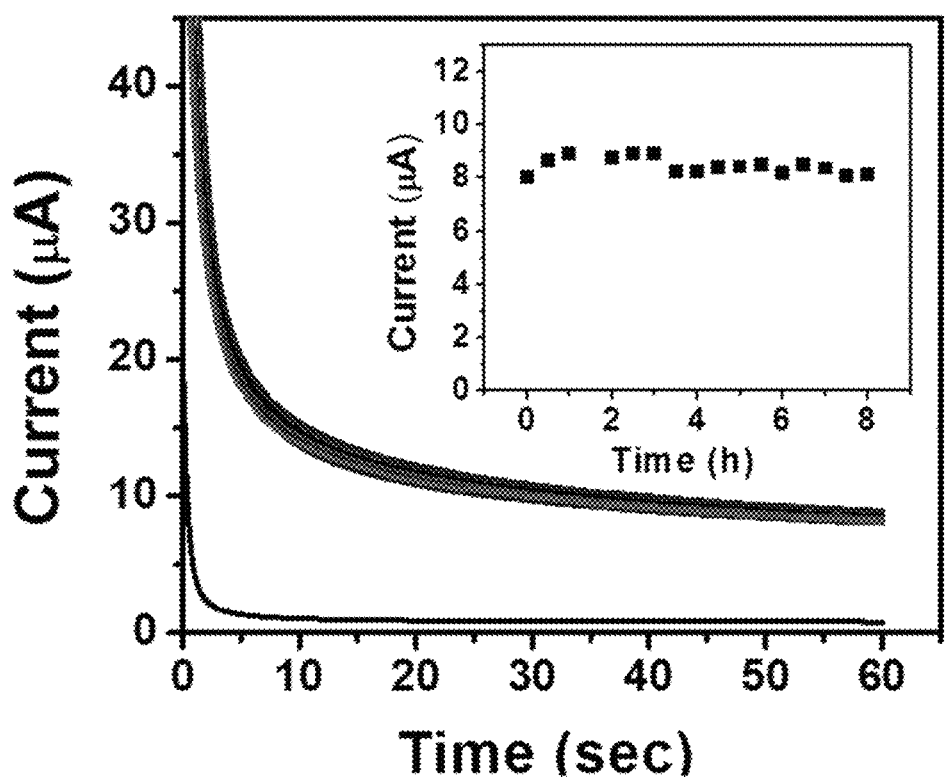
FIGS. 13A and 13B show data plots of the stability of an exemplary lactate T3 electrochemical sensor.

For example, a person can apply an exemplary lactate T3 sensor of the disclosed technology to the epidermis and continuously monitor the health status. For such uses, the lactate T3 sensors can provide stable reproducible signals at room temperature during long periods of operations. The stability of the lactate T3 sensors may depend on the stability of the enzyme. To evaluate this, a time dependent analysis of an exemplary lactate T3 sensor device was performed in which the response of the tattoo was recorded. FIG. 13A shows a data plot showing the stability of an exemplary lactate T3 electrochemical sensor. The inset plot shows the corresponding current-time data of the amperometric responses. The data plot of FIG. 13A shows that the exemplary sensor provided reproducible results (e.g., RSD=3.6%), which underscores its applicability for long term epidermal use.

Figure 13B:
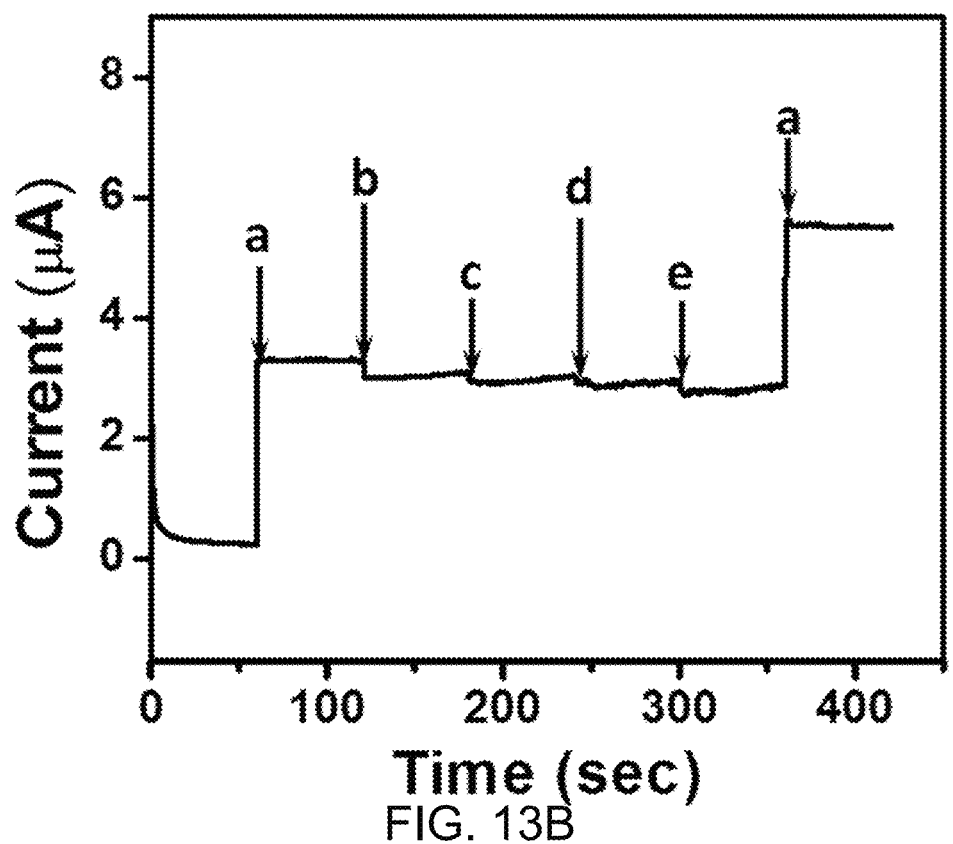

In addition, for example, the human sweat includes several metabolites and electrolytes. Out of these, creatinine, ascorbic acid, glucose and uric acid can affect the response of the exemplary enzymatic T3 sensors. An exemplary lactate T3 sensor device was implemented in presence of these exemplary interferents at physiological concentrations. FIG. 13B shows a data plot of an interference implementation with (a) 4 mM L-lactate, (b) 84 µM creatinine, (c) 10 µM ascorbic acid, (d) 0.17 mM glucose and (e) 59 µM uric acid. As shown in the data plot of FIG. 13B, the exemplary interferents exhibited minimal effect on the response due to lactate with signal deviation not more than 6% for each of the interferents.

For example, the human epidermis regularly experiences deformations due to bodily movements. Such epidermal deformations are a major cause of concern for wearable devices in which the devices undergo disfigurations similar to the skin. This can be true for epidermal electronics since these go directly on the human skin. As the human body moves, the skin can undergo bending, stretching and twisting stress. Mechanical strain can lead to increased surface area of printed wearable devices. The amperometric response is a function of the electrode area. Varying electrode area affects the sensor signal and can lead to undesired results.

Figure 14A:
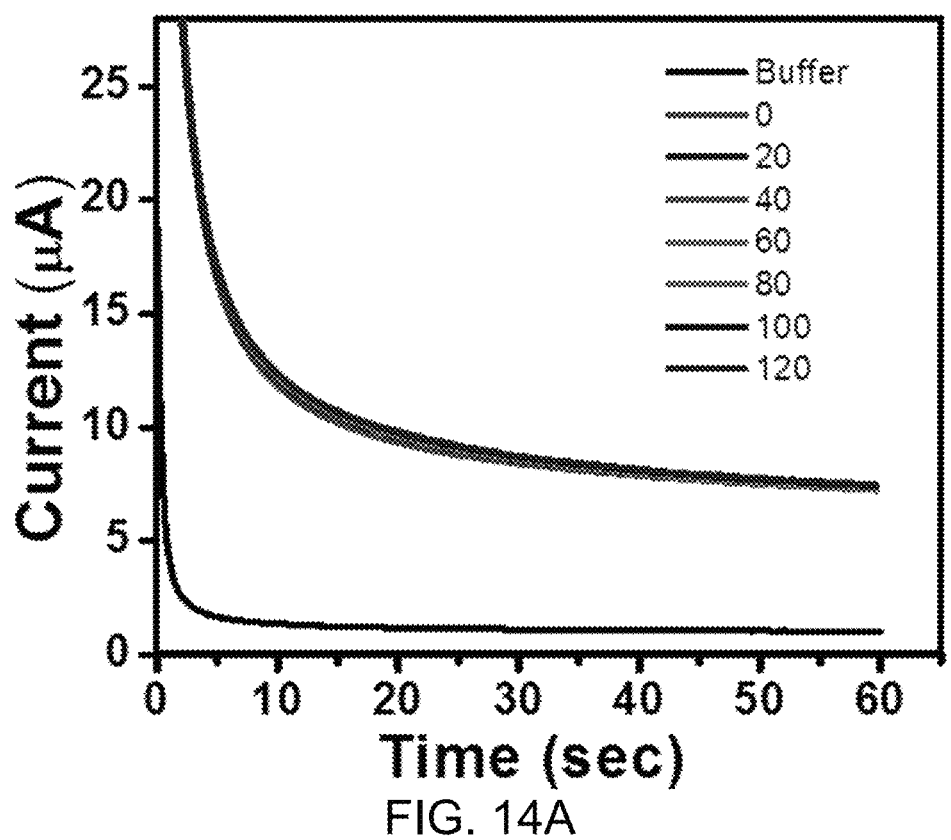
FIGS. 14A-14D show data plots of the electrochemical responses of an exemplary lactate T3 sensor.
Figure 14B:
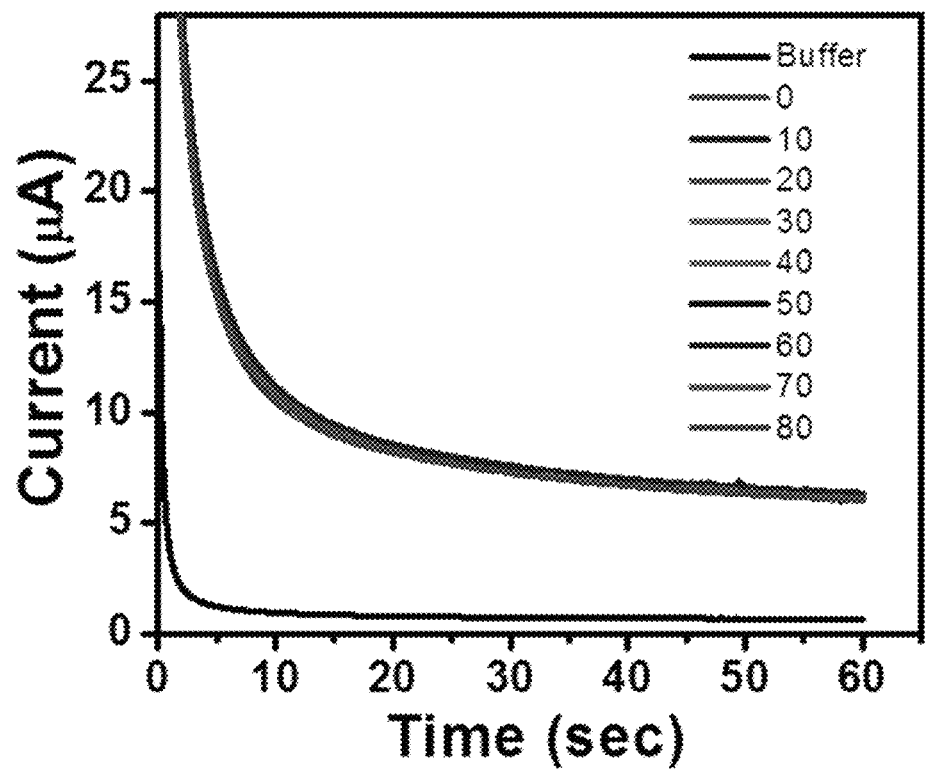
Figure 14C:
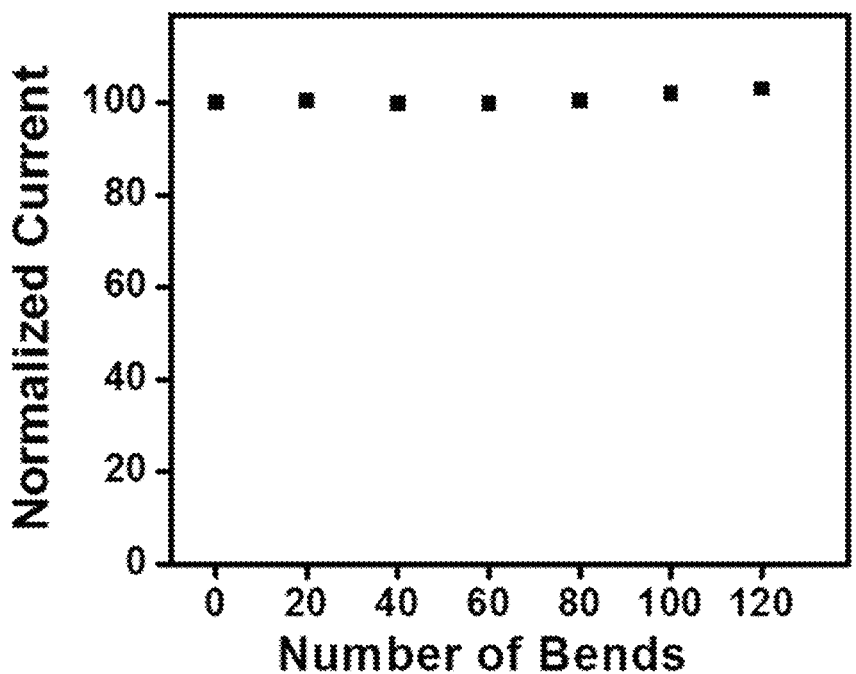
Figure 14D:
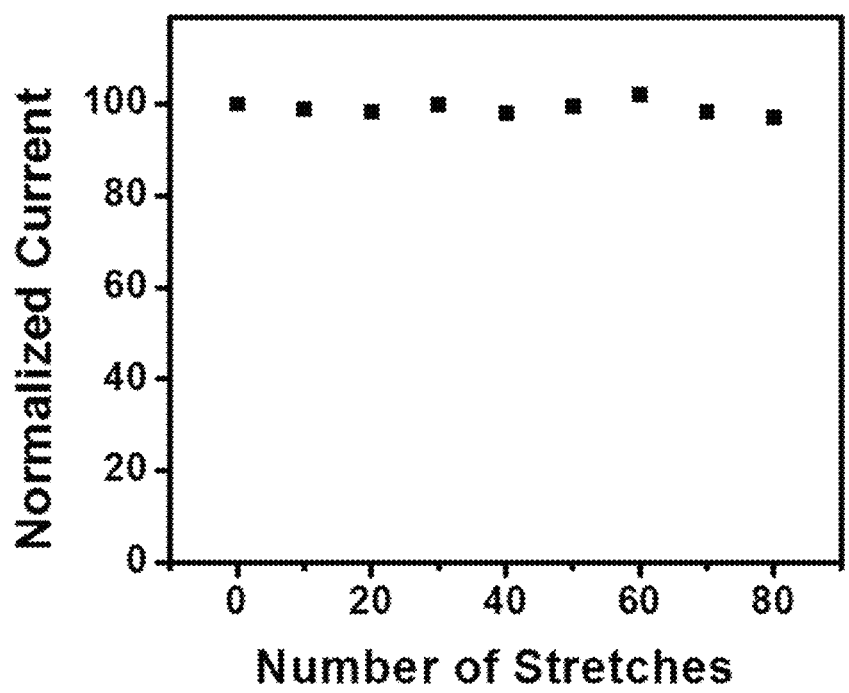

Exemplary implementations were performed to evaluate the mechanical resiliency of the exemplary lactate T3 electrochemical sensor devices. The robustness of the exemplary T3 sensor was implemented by applying it to GORE-TEX and bending it for 120 times by 90° while the sensor response was recorded after every 20 bending iterations. This was followed by stretching the same tattoo by 10% for a total of 80 times with data recorded every 10 stretching iterations. Each bending/stretching cycle included bending/stretching for 5 s followed by relaxation of another 5 s. FIGS. 14A-14D show data plots of the electrochemical responses of an exemplary lactate T3 sensor transferred on a flexible GORE-TEX textile undergoing repeated bending (FIG. 14A) and stretching (FIG. 14C), with their normalized current plots (FIGS. 14B and 14D, respectively). As demonstrated by the data in the data plots of FIGS. 14A-14D, the response of the exemplary lactate T3 sensor in each mechanical stress implementation remained substantially stable with an exemplary R.S.D. of 1.24% and 1.50% during bending and stretching, respectively. For example, the minimal deviation of the exemplary sensor response even after subjecting it to large number of stress cycles may be attributed to two reasons, e.g., (i) the carbon fiber dispersed in the carbon and Ag/AgCl inks and the MWNTs drop casted on the printed T3 sensor may enhance the resiliency of the tattoos towards mechanical deformations while providing electrical connectivity and (ii) the transparent insulator covering majority of the exemplary T3 sensor surface area may further help in avoiding crack developments within the device. Therefore, the disclosed enzymatic T3 sensors are a capable of performing desirably under various strains and thus serve as a compelling epidermal sensing platform.

Figure 15:
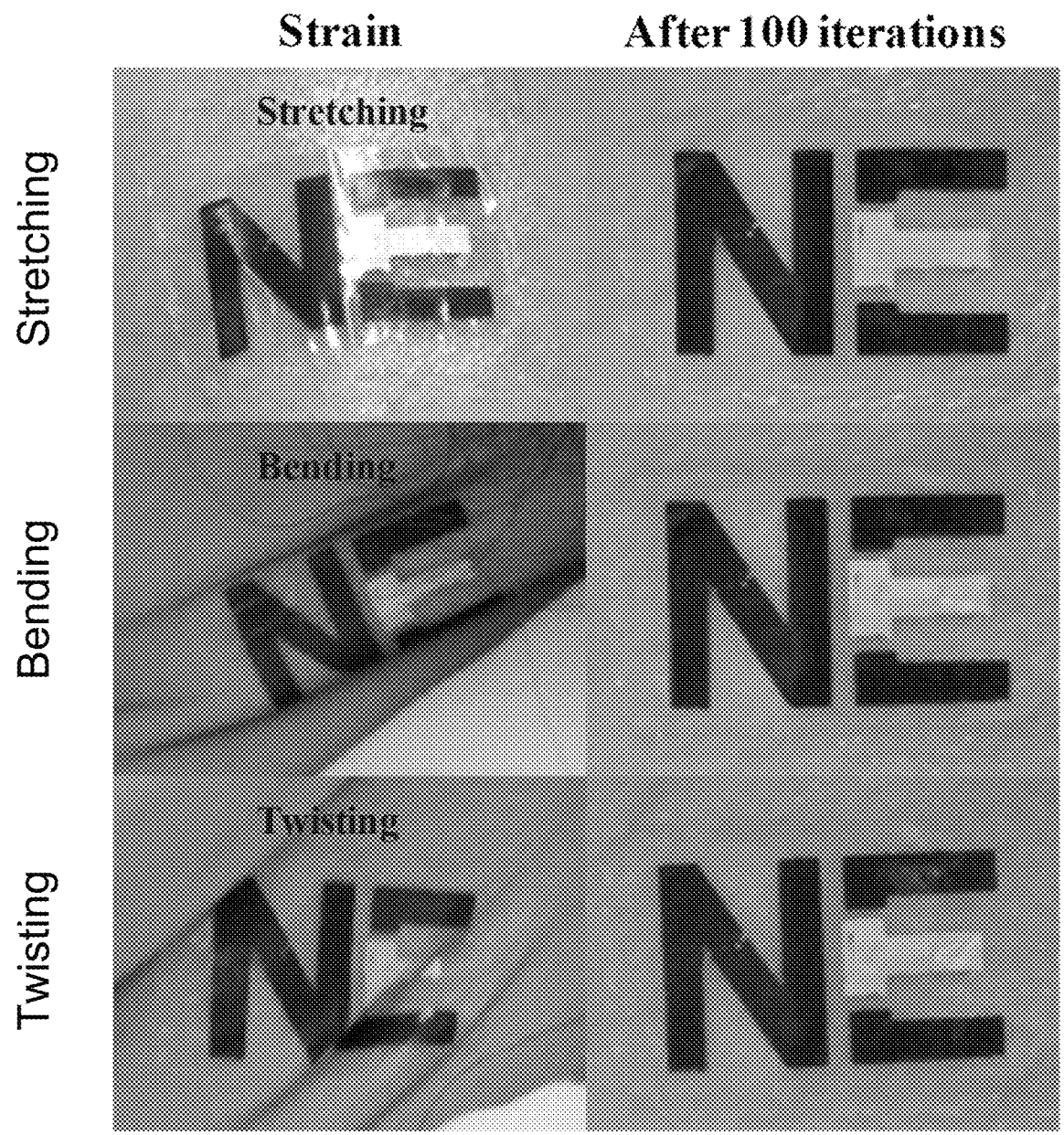
FIG. 15 shows images of the exemplary epidermal electrochemical sensor of FIG. 11A implemented under various strain conditions.

FIG. 15 shows images of exemplary lactate T3 sensors on human skin on the neck under mechanical strain including stretching (top row), bending (middle row), and twisting (bottom row) endured by a bare 'NE' tattoo during and subsequent to 100 stretching, bending, and twisting iterations (shown in the right column of images). The exemplary images demonstrate that the T3 sensors are quite resilient to such flexions.

The disclosed epidermal lactate T3 sensors can be implemented for real-time, online monitoring of the lactate concentration during human exercise. Examples of screen-printed temploarary transfer tattoo lactate sensors were modified with LOx for the oxidation of sweat lactate and MWNTs/TTF to enhance transduction, which were used in various in vitro and on-body implementations. In the exemplary in vitro implementatoins, the exemplary enzymatic T3 sensors exhibited a wide linear range up to 20 mM with a high sensitivity of 644.2 nA/mM. The exemplary enzymatic T3 sensors also showed specific selectivity toward lactate, e.g., demonstrated in exemplary implementations that included adding several interfering metabolites common in sweat. In addition, for example, the electrochemical performance of the exemplary enzymatic T3 sensors was shown to be consistent with bending and stretching the tattoos transferred on GORE-TEX and human skin located at the neck. Exemplary results showed that the exemplary enzymatic T3 sensors can provide real-time sweat lactate concentration patterns.

In another aspect of the disclosed technology, the disclosed epidermal electrochemical sensors can be included with epidermal biofuel cells to form an on-body, wearable complete self-powering monitoring system.

Examples of the epidermal printed biofuel cells including methods, systems, and devices are described in the PCT Patent Application document, entitled "PRINTED BIOFUEL CELLS", filed Nov. 30, 2012, which is incorporated by reference in its entirety as part of the disclosure in this patent document.

Exemplary implementations of the printed biofuel cells and methods to fabricate them are described in this patent document.

The disclosed technology includes wearable epidermal biofuel cell devices to provide continuous power generation while worn on a human or other user. In some implementations, the exemplary wearable biofuel cell device can be applied to the wearer's epidermis as a temporary-transfer tattoo and is able to scavenge an ample supply of the biofuel L-lactic acid found in the wearer's perspiration in order to generate power. In this exemplary device, the electrodes of the wearable epidermal biofuel cell can be functionalized with lactate oxidase and platinum black within the anode and cathode, respectively, to achieve the power generating operation. Exemplary implementations of the exemplary wearable epidermal biofuel cell were performed to demonstrate the application of various forms of mechanical deformation relevant to practical epidermal applications, which resulted in minimal effects on the performance of the device. For example, an exemplary implementation of the epidermal tattoo biofuel cell device during a controlled fitness routine revealed a maximum power density of 68 $\mu W\ cm^{-2}$ was obtained, hence realizing power production from human perspiration. The epidermal bioenergy paradigm thus holds noteworthy potential for use in the fitness, sport, athletics, performance, and generalized healthcare monitoring domains.

As the cost of personal health monitoring continues to rise, the fitness and healthcare industries have become increasingly reliant on wearable sensors to quantify various physiological metrics in a non-intrusive, user-friendly, and cost-effective fashion to reduce such costs. For example, for epidermal biosensing applications, durability, light-weight, and intimate skin conformance are core requirements of such sensor devices to assess vital signs, e.g., such as heart rate, respiration rate, oxygenation of the blood, skin temperature, bodily motion, brain activity, and blood pressure, as well as chemical sensors capable of monitoring various physiological analytes on the wearer's epidermis as well as chemical agents in their local vicinity. For example, these conformal electronic and diagnostic technologies have advanced considerably to the point of integration of disparate systems on a single skin-adhesive substrate. However, further progress in this arena has been hindered by the lack of wearable and conformal power sources, especially those able to harness the mechanical or chemical energy produced by the wearer's body. While flexible and thin battery technologies have been developed, toxicity, longevity, device weight, and overall poor operational performance have precluded their use in transdermal applications, as well as the rigorous mechanical deformation encountered during bouts of physical activity remains to be addressed with respect to these devices. Additionally, piezoelectric energy harvesting materials have also been plagued by the low efficiencies associated with the electromechanical interconversion process in crystalline media lacking inversion symmetry. The disclosed wearable epidermal biofuel cell technology can be implemented to circumvent these challenges with conventional power sources and provide continuous extraction of biochemical fuels from the wearer's epidermis, which can further enable the development of epidermal electronics that can be utilized in the field.

Exemplary implementations of exemplary wearable epidermal biofuel cell devices were performed that demonstrated the ability to generate useful levels of power from the perspiration of live subjects in a non-invasive and continuous fashion through the use of temporary-transfer tattoos. In some implementations, this was accomplished via the selective oxidation of lactate present in the wearer's perspiration through the inclusion of the enzyme lactate oxidase in the anode matrix in conjunction with the water-insoluble electrochemical mediator tetrathiafulvalene (TTF). For example, lactic acid is the most abundant molecular constituent of the perspiration and is also a widely-recognized indicator of exercise intensity, muscular exertion, fatigue, and aerobic/anaerobic respiration. Charting lactate levels in real-time can thus yield timely information regarding an individual's metabolic response to a fitness routine, hence enabling the individual, trainer, coach, and/or healthcare provider to quantify performance levels. Advantageously, an individual's fitness levels and aerobic capacity can indirectly be inferred by the amount of current (and hence power density) produced by the device.

The disclosed tattoo biofuel cell devices address the requirements imparted by epidermal wear, e.g., including, but not limited to, the ability of the device to maintain its structural and electrochemical resiliency against repeated (and often severe) mechanical deformation such as sheer stress and strain. For example, the exemplary tattoo biofuel cell devices can include dispersed carbon fibers within the ink used to print the anode and cathode electrodes, multi-walled carbon nanotubes incorporated in the electrode contingents to facilitate electron transfer, as well as the immobilization of the catalyst (e.g., lactate oxidase) entrapped in a biocompatible chitosan membrane, which synergisticly results in the fabrication of biofuel cells that are largely impervious to mechanical strain, stress, and degradation associated with epidermal wear. For example, operation of the exemplary tattoo biofuel cell devices can produce a redox current from the direct oxidation of lactate within the perspiration via biocatalysis at the anode (and concomitant catalytic reduction of oxygen at the cathode) to generate electrical energy at a load. As such, the disclosed tattoo biofuel cell devices can be implemented in a number of practical applications to satisfy the energy requirements of epidermal, transdermal, and percutaneous devices.

Exemplary materials and methods to implement the disclosed embodiment of the technology are presented. The following chemicals and reagents were used in the described implementations, which included tetrathiafulvalene (TTF), glutaraldehyde solution (8%), chitosan, Pt black, bovine serum albumin (BSA), lactic acid, glucose, potassium phosphate monobasic ($KH_2PO4$), potassium phosphate dibasic ($K_2HPO_4$), hydrochloric acid (HCl), ammonium hydroxide ($NH_4OH$), sodium chloride (NaCl), potassium chloride (KCl), calcium chloride ($CaCl_2$), magnesium chloride ($MgCl_2$), and sodium bicarbonate ($NaHCO_3$). Lactate oxidase (LOx) and carboxy-functionalized multi-walled carbon nanotubes (MWNTs-COOH) were obtained for use in the exemplary implementations. Exemplary reagents were used without further purification. Carbon fibers (e.g., 8 μm diameter, 6.4 mm length, 93% purity) were obtained and further processed to reduce their length to approximately 2 mm.

The fabrication of the exemplary tattoo biofuel cells used in the described implementations included the following processes and procedures, which were utilized in exemplary demonstrations and implementations of the disclosed embodiment under exemplary conditions disclosed herein. Design of the temporary transfer tattoo pattern was accomplished in AutoCAD (Autodesk, San Rafael, Calif.) and fabricated on 75 μm-thick stainless steel through-hole and mesh stencils (Metal Etch Services, San Marcos, Calif.). Unique stencil patterns were used for each layer printed. Chopped carbon fibers were dispersed within a conductive carbon (E3449) ink to increase the tensile strength of the electrode. Printing was performed using an MPM-SPM semi-automatic screen printer (Speedline Technologies, Franklin, Mass.). Blank temporary transfer tattoo paper and the accompanying adhesive substrate was used.

Figure 16:
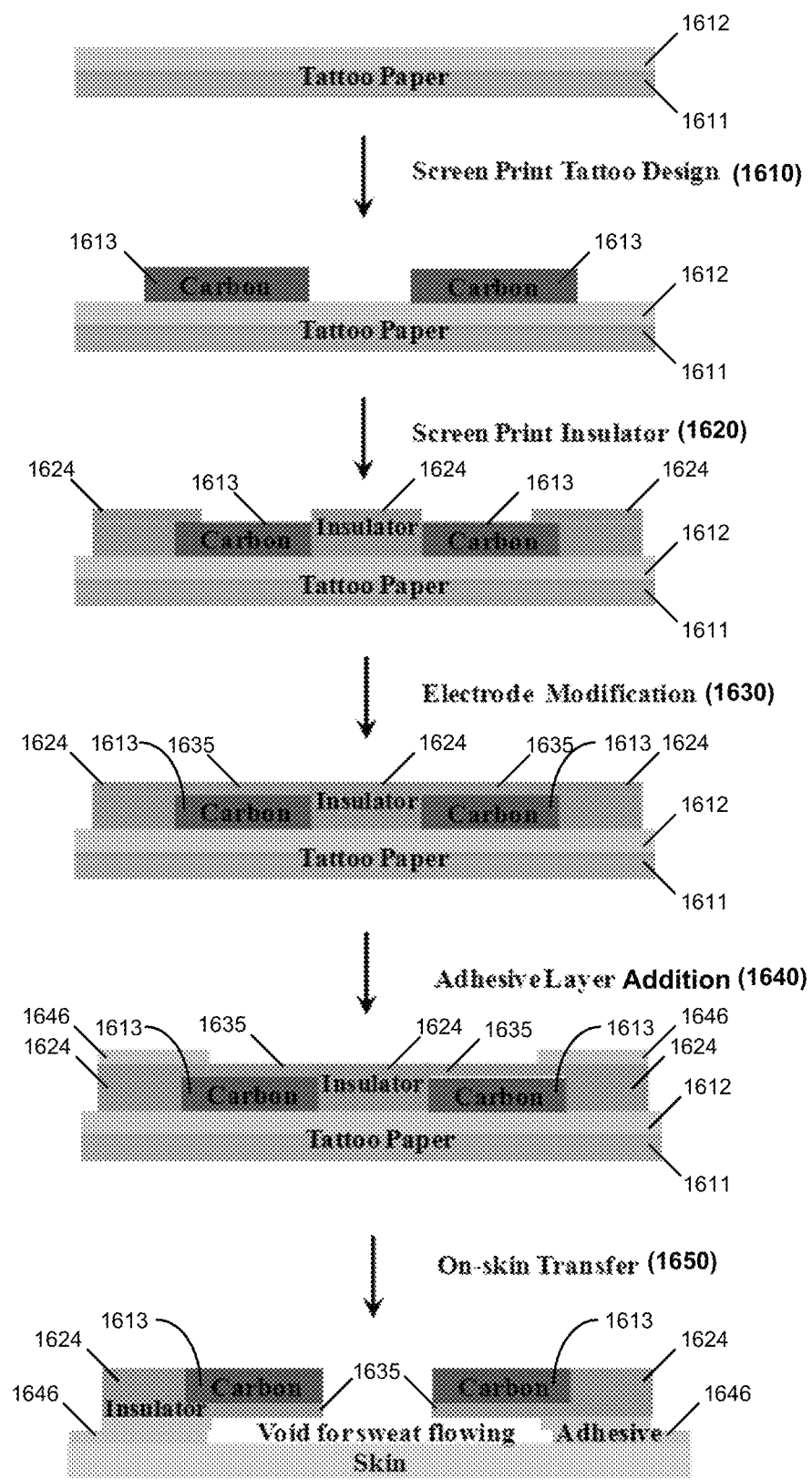
FIG. 16 shows a schematic illustration of an exemplary tattoo biofuel cell fabrication process.

FIG. 16 shows a schematic illustration of an exemplary method to fabricate tattoo biofuel cells using screen printing techniques. The fabrication method includes a process 1610 to deposit electrodes 1613 on a tattoo paper substrate comprising a release agent 1612 coated on a base paper 1611. For example, the release agent 1612 can include hydrophobic material that releases upon exposure moisture, e.g., such as polydimethylsiloxane (PDMS), a cellulosic-based material, a silicone material, among others. For example, the electrodes 1613 can formed by screen printing, roll-to-roll printing, aerosol deposition, inkjet printing, or other printing techniques to fabricate a printed anode and cathode of the tattoo biofuel cell device. The electrodes 1613 can be formed of a carbon-based ink material or other electrically conductive material, which can include a catalyst, e.g., including, but not limited to, an enzyme biocatalyst or noble metal catalyst, dispersed within the ink. Implementation of the process 1610 to deposit the electrodes 1613 can also include the formation of interconnects, contact pads, or other electrical components of the tattoo biofuel cell device. The process 1610 can include a curing procedure to thermally or UV cure the electrodes 1613 on the tattoo paper substrate material. In some implementations, the process 1610 can include the deposition and curing of an underlayer of an electrically conductive material, which can include the interconnects, contact pads, or other electrical components of the tattoo biofuel cell device. The fabrication method includes a process 1620 to deposit a layer of a transparent insulator material 1624 on the tattoo paper substrate exposing the electrodes 1613. The fabrication method includes a process 1630 to modify the electrodes 1613 with a biochemical modifier 1635. In some implementations, the process 1630 can include attaching the catalyst as the biochemical modifier 1635 to the anode and/or cathode by coating the catalyst as a layer on the surface of the anode and/or cathode electrode; by entrapping the catalyst in an electropolymerized conducting polymer formed on the surface of the anode and/or cathode electrode; by entrapping the catalyst using a selectively permeable scaffold-like structure, e.g., such as an electro-permeable membrane, formed on the surface of the anode and/or cathode electrode; by covalently bonding the catalyst to the surface of the anode and/or cathode electrode; or by electrostatically anchoring the catalyst to the surface of the anode and/or cathode electrode. In some implementations, the process 1630 can include attaching an electroactive mediator as the biochemical modifier 1635, in addition to or alternatively to the catalyst, to the anode and/or cathode electrode using any of the described techniques. The fabrication method includes a process 1640 to deposit an adhesive layer of an adhesive material 1646 over at least a portion of the transparent insulator material 1624 on the tattoo paper substrate, e.g., still exposing the electrodes 1613, to produce the tattoo biofuel cell device ready for implementation and wearable on a user's body. For example, subsequent to the fabrication method, the tattoo biofuel cell device can be attached to a user in an on-skin transfer process 1650, in which the adhesive layer is directly attached to the skin and the tattoo paper substrate is peeled off of the device by removing the release agent 1612 (e.g., which also removes the base paper 1611). For example, in some implementations, the fabricated tattoo biofuel cell device can include a void region to permit sweat or other substance including the biofuel to flow.

The two electrode constituents of the tattoo biofuel cell were designed in the shape of 'UC' (acronym for the University of California). As shown in FIG. 16, the entire contingent was printed on the tattoo base paper using carbon fiber-reinforced (1.5% wt.) carbon ink via the thick-film screen printing fabrication process utilizing the stencil set. This was followed by the screen printing of a transparent insulator (Dupont 5036, Wilmington, Del.) on top of the carbon electrodes. The stencil employed for the transparent insulator ink was designed to insulate all but the active areas of the two electrodes. Following every screen printing step, the printed tattoo paper was cured at 90° C. for 15 min in a convection oven.

Following the fabrication of the tattoo BFC, the anode ('U') was modified with LOx while the electrode 'C' was functionalized with Pt black to serve as the cathode. With respect to the bioanode modification, a suspension of carbon nanotubes in ethanol (5 mg/mL) was sonicated for several hours, and then mixed with 0.1 M TTF ethanol/acetone solution in a 2.0:1.6 volume ratio. The suspension was subsequently cast onto the open area of the anode. After the electrodes completely desiccated, 5 μL LOx solution (40 mg/mL with 10 mg/mL BSA) was cast on the electrode, and then covered with 2 μL of 1 wt % chitosan solution. The electrodes were then cross-linked with glutaraldehyde vapor and stored at 4° C. overnight. To modify the tattoo BFC cathode, an aqueous solution of 10 mg/mL Pt black was sonicated and 10 μL of the suspension was cast on the electrode. Following complete desiccation, 1 μL Nafion solution (5 wt %) was cast on the electrode to act as a protective layer.

As illustrated in FIG. 16, in order to transfer the tattoos to a substrate, a transparent adhesive sheet was first applied to the tattoo paper, which ensured that the tattoo adhered satisfactorily to the body/substrate. A rectangular region was excised from the adhesive sheet such that the active anode and cathode areas remained unobstructed to enable the facile diffusion of lactate and oxygen to the respective electrode contingents. In order to apply the adhesive layer to the substrate, one of the transparent protective sheets from the adhesive sheet was removed and the adhesive layer was first mated with plain tattoo base paper. Later, the second transparent protective sheet mated with the adhesive sheet was removed to expose the adhesive layer. A void was also left between the anode and cathode contingents to facilitate the flow of perspiration between these two components. Next, the tattoo contingent was applied to the substrate, the base paper was dabbed with water to dissolve the release agent, and the wet base paper was gently removed to expose the adhesive layer on the substrate. The tattoo BFC was finally placed on the adhesive sheet already located on the substrate and removed by dabbing it with water and gently peeling the base paper from the substrate.

In one exemplary embodiment of the disclosed tattoo biofuel cell device, an epidermal biofuel cell device includes a substrate formed of a flexible electrically insulative material structured to adhere to the skin of a user, an anode formed on the substrate of an electrically conductive material, the anode including a catalyst to facilitate the conversion of a fuel substance in a biological fluid to a first product in an oxidative process that releases electrons captured at the anode, thereby extracting energy from the fuel substance, a cathode configured on the substrate adjacent to the anode and separated from the anode by a spacing region, the cathode formed of a material that is electrically conductive and capable of reducing an oxygenated substance in the biological fluid to a second product in a chemical reduction process in which the second product gains electrons, and an anode electrode interface component and a cathode electrode interface component formed on the substrate and electrically coupled to the anode and the cathode, respectively, via electrical interconnects, in which the extracted energy is addressable as electrical energy at the anode electrode interface component and the cathode electrode interface component.

Exemplary implementations of the exemplary tattoo biofuel cell device were performed to perfect the device with regards to the electrochemical performance in vitro. For example, the tattoo biofuel cells were first evaluated by transferring the pattern onto a rigid plastic substrate or onto a flexible GORE-TEX textile for mechanical integrity studies. For example, 0.2 M McIlvaine buffer (pH 5.5) was utilized to emulate the average pH value of human perspiration. With respect to in vitro stability evaluation, artificial perspiration was prepared with the following electrolytes, metabolites, and small molecules, e.g., including $Na_2SO_4$, $NaHCO_3$, $KCl$, $MgCl_2$, $NaH_2PO_4$, $CaCl_2$, acetic acid, lactic acid, pyruvic acid, glucose, uric acid, urea, creatinine and ascorbic acid. The pH of the artificial perspiration stock solution was adjusted to 5.3 by 5 M $NH_4OH$. The exemplary solutions were prepared with ultra-pure water (18.2 MΩ·cm). Electrochemical characterization was performed at room temperature leveraging a CH Instruments (Austin, Tex.) model 1232A potentiostat.

Healthy volunteer subjects participated in the exemplary power generation experiments. Each volunteer was instructed to wear a temporary transfer tattoo BFC on their upper bicep in order to assess real-time power generation. The BFC was connected to an external 100 kΩ load resistor ($R_L$) in order to achieve maximum power transfer. This value was selected to most closely match the internal series resistance ($R_s$) such that the maximum power transfer condition was satisfied ($R_s=R_L$). Electrical current was recorded every 5 s using a Keithley (Cleveland, Ohio) 6514 system electrometer interfaced with a computer system including at least a processor and a memory unit including a control program (e.g., instructions in Matlab) to continuously process acquired current readings via the GPIB interface and interpolated the concomitant power generated per unit area ($P_{DENSITY}=I^2R_L/A_E$, $A_E=0.06$ cm$^2$). In order to filter extraneous noise, a 10-point moving average was iterated at each data point. For example, the subjects were instructed to mount a stationary cycle and a heart rate (HR) monitor was employed to track the subjects' HR. Subjects were instructed to begin cycling at a steady, slow cadence for 3 min. Following this 'warm-up' period, subjects were instructed to cycle at an increasing pace until 80% of their maximum heart rate was achieved in order to ensure that the anaerobic respiration threshold was attained, hence augmenting the excretion of lactic acid in the perspiration. Immediately following the subjects' transition to the anaerobic regime, the subjects were instructed to maintain their current cadence for 15 min in order to observe the temporal evolution of the lactate level. Following the 15 min intense exercise activity, subjects were instructed to gradually reduce their cadence during a 3 min 'cool-down' period. The volunteers ingested no fluid (dehydrated state) prior to and during the duration of the fitness routine.

Figure 17:
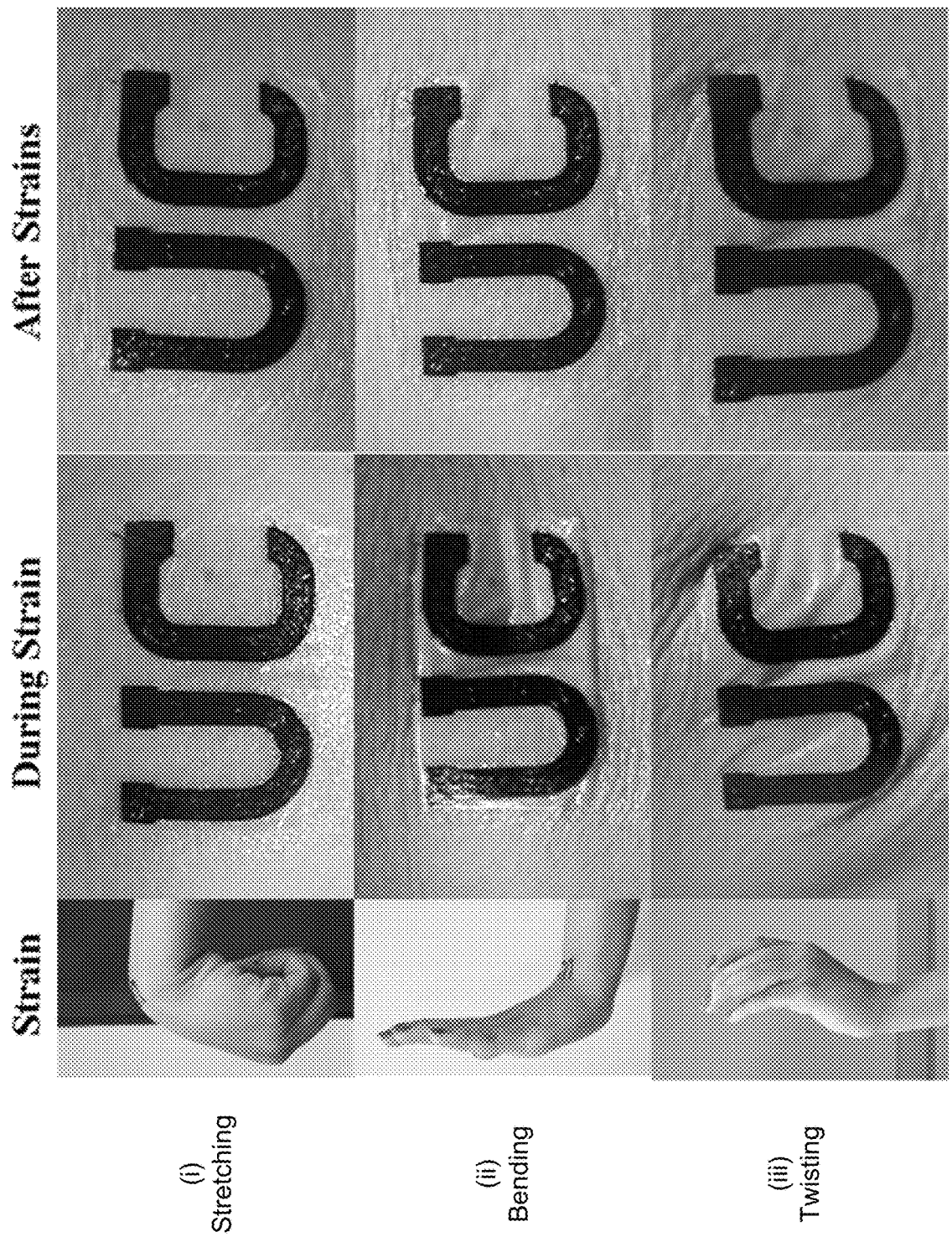
FIG. 17 shows images of mechanical strain implementations on a human wrist of an exemplary tattoo biofuel cell device during and after stretching, bending, and twisting.

Exemplary implementations of exemplary wearable epidermal biofuel cell devices were performed that demonstrated resiliency against mechanical stress caused by continuous body movements. For example, the longevity of such epidermal-mounted devices depend greatly on their ability to adhere well to the human skin without developing fractures that damage the devices. The most common body movements involve flexions, which typically comprise of bending, stretching, and/or twisting of the epidermal layer. Accordingly, such devices must encompass an intrinsic flexible and stretchable nature in addition to being able to adhere well to the epidermis. The disclosed tattoo biofuel cell devices include dispersion of carbon fibers within the inks employed to print these devices, which provide a conductive, interleaved backbone that aids in maintaining the electrical conductivity under various biomechanical stressors. Similarly, the use of an adhesive layer firmly attaches the tattoo biofuel cells to the skin. Visual analysis of the tattoo biofuel cell device on the dorsal region of a human wrist under repeating bending, stretching, and twisting dorsiflexion movements was performed for a total of 50 iterations. FIG. 17 shows images of the epidermal tattoo biofuel cells during mechanical stress caused by continuous body movements including (i) stretching, (ii) bending, and (iii) twisting. The left column of image in FIG. 17 provides the side view of dorsal movements; the middle column provides images of the top view of the biofuel cell tattoos during the various deformations; and the right column provides images of the top view of the biofuel cell tattoos at the end of each movement. The images demonstrate that the tattoo biofuel cell devices are quite resilient to flexions that emulate epidermal wear, e.g., as a consequence of the overlying insulator layer, which serves to maintain the structural integrity of the printed carbon layer. Accordingly, the epidermal biofuel cell devices can perform desirably under various strains and thus can serve as a compelling platform for various epidermal applications.

To date, the majority of lactate biofuel cells have been based on the lactate dehydrogenase enzyme. However, in these existing devices, $NAD^+$ must be employed as the cofactor, which represents a noteworthy challenge given that this molecule must be immobilized on the electrode to prevent it from leeching into the matrix while being able to diffuse, with relative ease, to the enzyme's active site.

The disclosed technology includes an exemplary lactate-based biofuel cell utilizing the lactate oxidase (LOx) enzyme for non-invasive power generation from human perspiration, e.g., by selectively catalyzing the oxidation of lactate in the perspiration as the biofuel for epidermal power generation. In some implementations the electrodes of the exemplary tattoo biofuel cell device are functionalized to achieve efficient bioelectrocatalytic conversion, e.g., in which the 'U' of the tattoo (anode) was functionalized with MWNTs/TTF/LOx, hence serving as the bioanode to catalyze the oxidation of lactate to pyruvate in the presence of oxygen (cofactor). The cathode 'C' made use of a drop-casted Pt black layer, protected with a Nafion proton-exchange membrane.

An image of the exemplary functionalized device is shown in FIG. 18A. The bioanode of the exemplary tattoo biofuel cell device was functionalized with the mediator TTF and MWNTs. This bioanode was then covered with a layer of chitosan, e.g., a naturally-derived biopolymer well-known for its biocompatibility. For example, chitosan not only serves to protect the modified enzyme electrode, but it also functions as a physical barrier to limit the efflux of the biocatalytic backbone from the tattoo and onto the underlying substrate.

FIG. 18B shows a data plot of polarization curves of the exemplary functionalized MWNTs/TTF/LOx bioanode in the absence of presence of 14 mM lactic acid in 0.2 M McIlvaine buffer solution, pH 5.5, respectively. The electrocatalytic activity of the MWNTs/TTF/LOx bioanode was determined in vitro with an external Ag/AgCl (1 M KCl) electrode and a Pt wire counter electrode. Polarization curves were recorded by applying linear sweep voltammetry with a scan rate of 1 mV/s in McIlvaine buffer pH 5.5 with 14 mM lactic acid, and normalized by the surface area of the electrode as a function of potential. As shown in FIG. 18B, the TTF-mediated oxidation of lactic acid initiates from around −0.1 V with a peak potential of 0.14 V (vs. Ag/AgCl), indicating that the MWNTs/TTF/LOx exhibits selective catalytic ability towards the oxidation of lactic acid, and hence serves as a suitable bioelectrocatalytic cascade for the bioanode constituent of the BFC. For example, TTF can be used a selective mediator to aid in electron transfer between the LOx active site and the electrode surface. Other mediators, e.g., including, but not limited to, derivatives of ferrocene and Meldola's blue, can also be used as the selective mediator of the bioanode. It is noted that although able to mediate the electro-oxidation of lactic acid, these other small-molecule mediators are water-soluble, and the oxidation current obtained may be decayed as a consequence of the leaching of the mediator. Compared with these mediators, TTF encompasses several noteworthy advantages, namely lower oxidation potential and more stable performance. Also, the incorporation of MWNTs further shifted the lactic acid oxidation onset potential more negatively and further enhanced the oxidation current, which may be due to the electron donor-acceptor interaction between TTF and negatively charged MWNTs, resulting in facilitated electron transfer to the electrode. Therefore, the MWNTs/TTF/LOx cascade is well-suited to serve as the bioanode, and, together with a Pt black cathode, a complete lactic acid biofuel cell can be assembled on the exemplary temporary transfer tattoo substrate.

FIG. 18C shows a data plot of power density achieved from the exemplary tattoo biofuel cell device with different lactic acid concentrations. As shown in the figure, the exemplary tattoo biofuel cell device approached 25 µW $cm^{-2}$ with 8 mM lactic acid (dissolved in buffer), and increased to 34 and 44 µW $cm^{-2}$ with further increased lactic acid concentrations of 14 mM and 20 mM, respectively. A small signal was observed during control experiments (no lactic acid added).

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. An epidermal electrochemical sensor device for detecting lactate in sweat, comprising:
   a substrate being a flexible and adhesive sheet including one or more electrically insulative materials that is structured to adhere to skin or a wearable item of a user of the device, the substrate having a first adhesive side and a second adhesive side opposite the first adhesive side;

an electrochemical sensor operable to facilitate a redox reaction to produce an electrical signal, comprising:

a first electrode disposed on the substrate and configured as a working electrode, the first electrode comprising a semi-conductive ink containing carbon microfibers, a second electrode disposed on the substrate and configured as a counter electrode, a third electrode disposed on the substrate and configured as a reference electrode, the third electrode comprising a conductive ink, a sensing layer disposed on an outer surface of the first electrode and comprising an electroactive redox mediator and multi-walled carbon nanotubes, wherein the sensing layer is configured to tether an active site of an enzyme catalyst comprising lactate oxidase, and a polymer layer disposed on the sensing layer and configured to protect the sensing layer and impede an efflux of constituents of the sensing layer from the first electrode; and a plurality of electrode interface components each electrically coupled to a respective one of the first electrode, the second electrode, and the third electrode via an electrically conductive conduit, wherein, when attached to the skin or the wearable item and electrically coupled via the plurality of electrode interface components to one or more electrical circuits, the epidermal electrochemical sensor device is operable to detect lactate in the user's sweat that contacts the device, wherein the epidermal electrochemical sensor device is able to undergo strain including 120 bends and 80 stretches while maintaining a substantially stable response, and wherein the first electrode, the second electrode, and the third electrode are disposed on the first adhesive side of the substrate, and wherein the substrate is structured to adhere to the skin or the wearable item of the user on either of the first adhesive side or the second adhesive side of the substrate.

2. The device of claim 1, wherein the polymer layer includes chitosan and the electroactive redox mediator includes tetrathiafulvalene.

3. The device of claim 1, wherein the device is configured to attach to the skin or the wearable item by the first adhesive side of the substrate and position the first electrode, the second electrode, and the third electrode to make contact with the skin.

4. The device of claim 1, wherein the device further comprises:

a paper sheet that is attachable to the second adhesive side of the substrate and configured to be peeled off of the substrate, wherein the device is configured to attach to the skin or the wearable item by the second adhesive side of the substrate after removal of the paper sheet.

5. The device of claim 1, wherein the one or more electrically insulative materials of the substrate includes a silicone.

6. The device of claim 1, wherein the substrate includes one or both of polyvinyl alcohol (PVA) and polydimethylsiloxane (PDMS).

7. The device of claim 1, wherein the one or more electrical circuits is configured to apply excitation waveforms and transduce the electrical signal produced by the device upon excitation.

8. The device of claim 7, wherein the one or more electrical circuits includes a potentiostat to obtain amperometric or voltammetric measurements or a galvanostat to obtain potentiometric measurements.

9. The device of claim 1, wherein the second electrode includes multi-walled carbon nanotubes.

10. The device of claim 1, wherein the second electrode includes an electrically conductive material that includes an electrically conductive ink, and wherein the electrically conductive ink includes at least one of gold, platinum, nickel, silver, or silver chloride.

11. The device of claim 10, wherein the second electrode further includes carbon fiber segments dispersed within the conductive ink.

12. The device of claim 1, wherein the second electrode includes an electrically semi-conductive material.

13. The device of claim 12, wherein the electrically semi-conductive material includes a semi-conductive ink including at least one of amorphous carbon, carbon black, or graphite.

* * * * *